United States Patent
Langkilde

(10) Patent No.: US 12,213,988 B2
(45) Date of Patent: *Feb. 4, 2025

(54) METHODS OF TREATING CHRONIC KIDNEY DISEASE WITH DAPAGLIFLOZIN

(71) Applicant: ASTRAZENECA AB, Södertälje (SE)

(72) Inventor: Anna Maria Langkilde, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/347,230

(22) Filed: Jun. 14, 2021

(65) Prior Publication Data

US 2022/0023321 A1    Jan. 27, 2022

Related U.S. Application Data

(63) Continuation of application No. 17/219,992, filed on Apr. 1, 2021.

(60) Provisional application No. 63/057,139, filed on Jul. 27, 2020, provisional application No. 63/070,869, filed on Aug. 27, 2020, provisional application No. 63/082,524, filed on Sep. 24, 2020, provisional application No. 63/093,961, filed on Oct. 20, 2020, provisional application No. 63/119,711, filed on Dec. 1, 2020, provisional application No. 63/152,445, filed on Feb. 23, 2021, provisional application No. 63/161,629, filed on Mar. 16, 2021.

(51) Int. Cl.
| | |
|---|---|
| A61K 31/7004 | (2006.01) |
| A61K 9/00 | (2006.01) |
| A61K 31/351 | (2006.01) |
| A61K 31/401 | (2006.01) |
| A61K 31/41 | (2006.01) |
| A61K 31/4178 | (2006.01) |
| A61K 45/06 | (2006.01) |
| A61P 13/12 | (2006.01) |

(52) U.S. Cl.
CPC ........ *A61K 31/7004* (2013.01); *A61K 9/0053* (2013.01); *A61K 31/351* (2013.01); *A61K 31/401* (2013.01); *A61K 31/41* (2013.01); *A61K 31/4178* (2013.01); *A61K 45/06* (2013.01); *A61P 13/12* (2018.01)

(58) Field of Classification Search
CPC .. A61K 31/7004; A61K 9/0053; A61K 45/06; A61P 13/12
USPC ......................................................... 514/23
See application file for complete search history.

(56) References Cited

U.S. PATENT DOCUMENTS

2012/0071403 A1   3/2012   Strumph et al.
2014/0323417 A1   10/2014  Blatter et al.

FOREIGN PATENT DOCUMENTS

| CN | 109922813 A | 6/2019 |
| KR | 10-2017-0069943 | 7/2019 |
| WO | WO 2018087132 A1 | 5/2018 |

OTHER PUBLICATIONS

Hiddo Lambers Heerspink (NIH, U.S. National Library of Medicine; ClinicalTrials.gov, Jun. 19, 2017).*
Momoniat et al. (Cleveland Clinic Journal of Medicine vol. 86 • No. 9 Sep. 2019, 601-607).*
Schmieder et al. (J Nephrol. Sep.-Oct. 2011;24(5):569-80) (abstract sent).*
Bamberg et al. (PLOS ONE, Feb. 23, 2018, 1-22).*
Cassis et al. (JCI Insight. 2018;3(15):e98720, 1-10).*
Cravedi et al. (Br J Clin Pharmacol / 76:4 / 516-523).*
Levey et al. (Kidney International, vol. 67 (2005), pp. 2089-2100).*
Jafar et al. (Kidney International, vol. 60 (2001), pp. 1131-1140).*
Eck, Cochrane Database of Systematic Reviews 2014, Issue 8, Art. No. CD009096. (Year: 2014).*
AstraZeneca, ClinicalTrials.gov ID NCT03036150, Version 27: Jan. 18, 2019 update posted Jan. 23, 2019, accessed online at https://clinicaltrials.gov/study/NCT03036150 on Jul. 17, 2023, 65 pages. (Year: 2019).*
McMurray, N Engl J Med 2019; 381: 1995-2008. (Year: 2019).*
Kohan, Kidney International (2014) 85, 962-971. (Year: 2014).*
International Search Report for PCT/EP2021/058727 dated Apr. 1, 2021.
Yamout, H., et al. (2014). "Efficacy and Safety of Canagliflozin in Patients with Type 2 Diabetes and Stage 3 Nephropathy." Am J Nephrol 2014;40:64-74.
Yale, J.-F, et al., (2014). "Efficacy and safety of canagliflozin over 52 weeks in patients with type 2 diabetes mellitus and chronic kidney disease." Diabetes, Obesity and Metabolism 16: 1016-1027, 2014.
Ketteler. M., et al. (2018). "Chronisches Nierenversagen—Update 2018." Dtsch Med Wochenschr 2018; 143: 169-173.
Kelly, M., et al. (2019). "Efficacy and renal outcomes of SGLT2 inhibitors in patients with type 2 diabetes and chronic kidney disease." Postgrad Med. 2019;131(1):31-42.
Sugiyama, S., et al. (2019). "Renoprotective Effects of Additional SGLT2 inhibitor Therapy in Patients With Type 2 Diabetes Mellitus and Chronic Kidney Disease Stages 3b-4: A Real World Report From a Japanese Specialized Diabetes Care Center." J Clin Med Res. 2019;11(4):267-274.
Toyama, T., et al. (2019). "Effect of SGLT2 inhibitors on cardiovascular, renal and safety outcomes in patients with type 2 diabetes mellitus and chronic kidney disease: A systematic review and meta-analysis." Diabetes, Obesity and Metabolism 2019;21:1237-1250.
Allegretti, A., et al. (2019). "Safety and Effectiveness of Bexagliflozin in Patients With Type 2 Diabetes Mellitus and Stage 3a/3b CKD." Am J Kidney Dis. 74(3): 328-337.

(Continued)

*Primary Examiner* — Layla D Berry

(74) *Attorney, Agent, or Firm* — Finnegan, Henderson, Farabow, Garrett & Dunner, LLP

(57) ABSTRACT

The present disclosure is directed to methods of treating patients with chronic kidney disease (CKD), with and without Type 2 diabetes, with an SGLT2 inhibitor, such as dapagliflozin.

24 Claims, 25 Drawing Sheets

(56) References Cited

OTHER PUBLICATIONS

Wanner, C., et al. (2016). " Empagliflozin and Progression of Kidney Disease in Type 2 Diabetes." *NEnglJMed* 375(4): 323-334.
Neal, B., et al. (2017). "Canagliflozin and Cardiovascular and Renal Events in Type 2 Diabetes." *NEnglJMed* 377(7):644-657.
Takashima, H., et al. (2018). "Renoprotective Effects of Canagliflozin, a Sodium Glucose Cotransporter 2 Inhibitor, in Type 2 Diabetes Patients with Chronic Kidney Disease: A Randomized Open-Label Prospective Trial." *DiabVascDisRes*15(5): 469-472.
Perkovic, V., et al. (2019). "Canagliflozin and Renal Outcomes in Type 2 Diabetes and Nephropathy." *NEnglJMed* 380(24): 2295-2306.
Pollock, C., et al. (2019). "Albuminuria-lowering effect of Dapagliflozin Alone and in Combination with Saxagliptin and Effect of Dapagliflozin and Saxagliptin on Glycaemic Control in Patients with Type 2 Diabetes and Chronic Kidney Disease (Delight): a Randomised, Double-Blind, Placebo-Controlled Trial." *LancetDiabetesEndocrinol* 7(6): 429-441.
Wiviott, S. D., et al. (2019). "Dapagliflozin and Cardiovascular Outcomes in Type 2 Diabetes." *NEnglJMed* 380(4): 347-357.
Cannon, C. P., et al. (2020). "Cardiovascular Outcomes with Ertugliflozin in Type 2 Diabetes." *NEnglJMed* 383(15): 1425-1435.
Cherney, D. Z. I., et al. (2020). "Effects of the SGLT2 Inhibitor Dapagliflozin on Proteinuria in Non-Diabetic Patients with Chronic Kidney Disease (Diamond): A Randomised, Double-Blind, Crossover Trial." *LancetDiabetesEndocrinol* 8(7): 582-593.
Heerspink, H. J. L., et al. (2020). "Rationale and Protocol of the Dapagliflozin And Prevention of Adverse Outcomes in Chronic Kidney Disease (DAPA-CKD) Randomized Controlled Trial." *Nephrol DialTransplant* 35(2): 274-282.
Heerspink, H. J. L., et al. (2020). "Dapagliflozin in Patients with Chronic Kidney Disease." *NEnglJMed* 383(15): 1436-1446.
Sternlicht, H. K., et al. (2020) "Reductions in Albuminuria with SGLT2 Inhibitors: a Marker for Improved Renal Outcomes in Patients Without Diabetes?" *Lancet Diabetes Endocrinol.* 8(7): 553-555.
Wheeler, D.C. et al., (2021) "Effects of Dapagliflozin on Major Adverse Kidney and Cardiovascular Events in Patients with Diabetic and Non-Diabetic Chronic Kidney Disease: a Prespecified Analysis from the DAPA-CKD Trial." *Lancet Diabetes Endocrinol.* 9(1): 22-31.
McMurray, J.J.V., et al. (2021) "Effect of Dapagliflozin on Clinical Outcomes in Patients with Chronic Kidney Disease, With and Without Cardiovascular Disease" *Circulation* 143:443-448.
Cherney, David Z. I., et al. (2020). "Effect of SGLT2 inhibitor dapagliflozin on proteinuria in non-diabetic patients with chronic kidney disease (Diamond): a randomized, double-blind, crossover trial," *Lancet Diabetes Endocrinal* 2020: 8: 582-93.
Michael F. Carroll "Proteinuria in Adults: A Diagnostic Approach." American Family Physician, vol. 62, No. 6, pp. 1333-1340 (Sep. 15, 2000).
Gounden V, Bhatt H, Jialal I. Renal Function Tests. In: StatPearls. StatPearls Publishing, Treasure Island (FL); 2022. PMID: 29939598.
Kashif, MD, Waqar et al., "Proteinuria: How to evaluate an important finding," Cleveland Clinic Journal of Medicine, vol. 70, No. 6, Jun. 2003, pp. 535-547.
National Kidney Foundation, "Estimated Glomerular Filtration Rate (eGFR)," available on https://www.kidney.org/atoz/content/grf, pp. 1-4.
Package Insert of Farxiga® (May 2023).
Ali S et al., Primary and secondary prevention of cardiovascular disease in patients with chronic kidney disease, Curr Atheroscler Rep, 2019, 21:32 (9 pages).

Idzerda N M.A. et al., Prediction of the effect of dapagliflozin on kidney and heart failure outcomes based on short-term changes in multiple risk markers, Nephrol Dial Transplant, 2020, 35:1570-1576.
Levey A.S., Nondiabetic kidney disease, N Engl J Med, 2002, 347(19):1505-1511.
New J et al., A case of acute renal failure and rhabdomyolysis associated with concomitant use of ticgrelor, rosuvastatin, and losartan, JSM Intern Med, 2017, 2(1):1004 (3 pages).
Susman E, HF benefit of dapagliflozin affirmed in non-diabetics-fewer CB events for heart failure with reduced ejection fraction, MedPage Today, Nov. 16, 2019 (3 pages).
Verma S and Bhatt D.L., More Credence for SLGT2 inhibition, Circulation, 2019, 140:1448-1450.
Bamberg K. et al., Preclinical pharmacology of AZD9977: A novel mineralocorticoid receptor modulator separating organ protection from effects on electrolyte excretion, PLoS One, 2018, 13(2):e0193380 (22 pages).
Dekkers CJ et al., Sodium-glucose cotransporter 2 inhibitors: extending to non-diabetic kidney disease? Nephrol Dial Transplant, 2020, 35 (Suppl 1): i33-i42.
Erlandsson F et al. Clinical safety, tolerability, pharmacokinetics and effects on urinary electrolyte excretion of AZD9977, a novel, selective mineralocorticoid receptor modulator, Br J Clin Pharmacol., 2018;84(7):1486-1493.
"Farxiga phase III Dapa CKD trial will be stopped early after overwhelmingly efficacy in patients with chronic kidney disease," Businesswire, Mar. 30, 2020, URL: https://www.businesswire.com/news/home/20200330005322/en/FARXIGA-Phase-III-DAPA-CKD-Trial-Will-Be-Stopped-Early-After-Overwhelming-Efficacy-in-Patients-With-Chronic-Kidney-Disease (4 pages).
Fioretto P et al., Efficacy and Safety of Dapagliflozin in Patients with Type 2 Diabetes and Moderate Renal Impairment (Chronic Kidney Disease Stage 3A): The Derive Study, Diabetes Obes Metab, 2018, 20:2532-2540.
Glasscock RJ, Dapagliflozin effect on chronic kidney disease in type 2 diabetes: analysis of the declare timi 58 randomized trial, American College of Cardiology, 2019, pp. 1-4.
Heerspink H, Effects of Dapagliflozin in Non-diabetic Patients With Proteinuria (Diamond), published on Sep. 27, 2019, https://www.clinicaltrials.gov/ct2/show/NCT03190694, pp. 1-8.
Heerspink HL, A Study to Assess the Renoprotective Effects of the SGLT2 Inhibitor Dapagliflozin in Non-Diabetic Patients With Proteinuria: a Randomized Double Blind 6-Weeks Cross-Over Trial, ClinicalTrials.gov, NCT03190694, Jun. 16, 2017 (v1) version (13 pages).
Herrington WG et al., The potential for improving cardio-renal outcomes by sodium-glucose co-transporter-2 inhibition in people with chronic kidney disease: a rationale for the EMPA-Kidney study, Clinical Kidney Journal, 2018, 749-761.
Whittaker A et al., Safety, Tolerability, and Pharmacokinetics of the Mineralocorticoid Receptor Modulator AZD9977 in Healthy Men: A Phase I Multiple Ascending Dose Study, Clin Transl Sci, 2019, vol. 13, No. 2, pp. 275-283.
Zou H et al., SGLT2 inhibitors: a novel choice for the combination therapy in diabetic kidney disease, Cardiovasc Diabetol, 2017, 16(1):65 (11 pages).
Lahnwong C. et al., Acuate dapagliflozin administration exerts cardioprotective effects in rats with cardia ischemia/reperfusion injury, *Cardiovasc Diabetol*, 2020, 19(91) (13 pages).
Sjostrom CD et al., Dapagliflozin lowers blood pressure in hypertensive and non-hypertensive patients with type 2 diabetes, *Diab Vasc Dis Res*, 2015, 12(5):352-358.

* cited by examiner

|  | Number (%) of patients | | |
| --- | --- | --- | --- |
|  | Dapa 10 mg | Placebo | Total |
| Patients randomised | 2152 | 2152 | 4304 |
| Patients who discontinued IP | 274 (12.7) | 309 (14.4) | 583 (13.5) |
| Patient Decision | 142 (6.6) | 160 (7.4) | 302 (7.0) |
| Adverse Events | 118 (5.5) | 123 (5.7) | 241 (5.6) |
| Subjects who discontinued study | 10 (0.5) | 5 (0.2) | 15 (0.3) |
| Withdrew consent | 8 (0.4) | 3 (0.1) | 11 (0.3) |
| Lost to follow-up | 2 (0.1) | 2 (0.1) | 4 (0.1) |
| Vital status at end of study |  |  |  |
| Dead | 107 (5.0) | 159 (7.4) | 266 (6.2) |
| Alive | 2043 (94.9) | 1990 (92.5) | 4033 (93.7) |
| Unknown | 2 (0.1) | 3 (0.1) | 5 (0.1) |

Fig. 2

| | | Dapa 10 mg (N=2152) | Placebo (N=2152) | Total (N=4304) |
|---|---|---|---|---|
| Age (years) | Mean | 61.8 | 61.9 | 61.8 |
| Sex n (%) | Female | 709 (32.9) | 716 (33.3) | 1425 (33.1) |
| Race n (%) | White | 1124 (52.2) | 1166 (54.2) | 2290 (53.2) |
| | Black or African American | 104 (4.8) | 87 (4.0) | 191 (4.4) |
| | Asian | 749 (34.8) | 718 (33.4) | 1467 (34.1) |
| | Hawaiian or other Pacific Islander | 1 (0.0) | 1 (0.0) | 2 (0.0) |
| | American Indian or Alaska Native | 62 (2.9) | 74 (3.4) | 136 (3.2) |
| | Other | 112 (5.2) | 106 (4.9) | 218 (5.1) |

Fig. 3

| Category / Metric | | Dapa 10 mg (N=2152) | Placebo (N=2152) | Total (N=4304) |
|---|---|---|---|---|
| Diabetes Status n (%) | T2DM | 1455 (67.6) | 1451 (67.4) | 2906 (67.5) |
| | No diabetes | 697 (32.4) | 701 (32.6) | 1398 (32.5) |
| eGFR (mL/min/1.73 m$^2$) | Mean | 43.2 | 43.0 | 43.1 |
| UACR (mg/g) | Median | 964.8 | 933.8 | 949.3 |
| Most likely aetiology of CKD n (%) | Diabetic Nephropathy | 1271 (59.1) | 1239 (57.6) | 2510 (58.3) |
| | Ischemic / Hypertension | 324 (15.1) | 363 (16.9) | 687 (16.0) |
| | Chronic Glomerulonephritis | 343 (15.9) | 352 (16.4) | 695 (16.1) |
| | IgA nephropathy | 137 (6.4) | 133 (6.2) | 270 (6.3) |

Fig. 4

|  | Number (%) of patients | | |
|---|---|---|---|
|  | Dapa 10 mg (N=2152) | Placebo (N=2152) | Total (N=4304) |
| ACE-I or ARB | 2094 (97.3) | 2080 (96.7) | 4174 (97.0) |
| ACE-I | 673 (31.3) | 681 (31.6) | 1354 (31.5) |
| ARB | 1444 (67.1) | 1426 (66.3) | 2870 (66.7) |
| Antithrombotic agents | 1022 (47.5) | 1020 (47.4) | 2042 (47.4) |
| Lipid lowering agents | 1495 (69.5) | 1493 (69.4) | 2988 (69.4) |
| Diuretics | 928 (43.1) | 954 (44.3) | 1882 (43.7) |

Fig. 5

| Variable | Dapa 10 mg (N=2152) Subjects with events n (%) | Event rate | Placebo (N=2152) Subjects with events n (%) | Event rate | Hazard ratio | 95% CI | p-value |
|---|---|---|---|---|---|---|---|
| Composite of ≥50% eGFR decline, ESRD, and renal or CV death | 197 ( 9.2) | 4.6 | 312 (14.5) | 7.5 | 0.61 | (0.51, 0.72) | <0.0001 |
| ≥50% decline in eGFR | 112 ( 5.2) | 2.6 | 201 ( 9.3) | 4.8 | 0.53 | (0.42, 0.67) | <0.0001 |
| ESRD | 109 ( 5.1) | 2.5 | 161 ( 7.5) | 3.8 | 0.64 | (0.50, 0.82) | 0.0004 |
| eGFR <15ml/min/1.73 m² | 84 ( 3.9) | 1.9 | 120 ( 5.6) | 2.8 | 0.67 | (0.51, 0.88) | 0.0043 |
| Chronic dialysis | 68 ( 3.2) | 1.5 | 99 ( 4.6) | 2.3 | 0.66 | (0.48, 0.90) | 0.0080 |
| Receiving renal transplant | 3 ( 0.1) | 0.1 | 8 ( 0.4) | 0.2 | | | |
| Renal death | 2 (<0.1) | 0.0 | 6 ( 0.3) | 0.1 | | | |
| CV death | 65 ( 3.0) | 1.4 | 80 ( 3.7) | 1.7 | 0.81 | (0.58, 1.12) | 0.2029 |

Fig. 6

| Variable | Type of endpoint | Dapa 10 mg (N=2152) Subjects with event n (%) | Placebo (N=2152) Subjects with event n (%) | Hazard ratio | 95% CI | p-value |
|---|---|---|---|---|---|---|
| Composite of >50% eGFR decline, ESRD and renal or CV death | Primary | 197 ( 9.2) | 312 (14.5) | 0.61 | (0.51, 0.72) | <0.0001 |
| Composite of >50% eGFR decline, ESRD and renal death | Secondary | 142 ( 6.6) | 243 (11.3) | 0.56 | (0.45, 0.68) | <0.0001 |
| Composite of CV death and hospitalization for HF | Secondary | 100 ( 4.6) | 138 ( 6.4) | 0.71 | (0.55, 0.92) | 0.0089 |
| Death from any cause | Secondary | 101 ( 4.7) | 146 ( 6.8) | 0.69 | (0.53, 0.88) | 0.0032 |

Fig. 10

| Variable | Dapa 10 mg (N=2373) | | Placebo (N=2152) | | Hazard ratio | 95% CI | p-value |
|---|---|---|---|---|---|---|---|
| | Subjects with events n (%) | Event rate | Subjects with events n (%) | Event rate | | | |
| Composite of CV death and hospitalization for HF | 100 ( 4.6) | 2.2 | 138 ( 6.4) | 3.0 | 0.71 | (0.55, 0.92) | 0.0089 |
| Hospitalization for HF | 37 ( 1.7) | 0.8 | 71 ( 3.3) | 1.6 | 0.51 | (0.34, 0.76) | 0.0087 |
| CV death | 65 ( 3.0) | 1.4 | 80 ( 3.7) | 1.7 | 0.81 | (0.58, 1.12) | 0.2029 |

Fig. 11

| | | Patients with events | | |
|---|---|---|---|---|
| | | Dapa | PBO | |
| Renal Composite | All Patients | 197 | 312 | 0.61 (0.51, 0.72) |
| | T2DM | 152 | 229 | 0.64 (0.52, 0.79) |
| | No DM | 45 | 83 | 0.50 (0.35, 0.72) |
| Renal Composite excl. CV death | All Patients | 142 | 243 | 0.56 (0.45, 0.68) |
| | T2DM | 103 | 173 | 0.57 (0.45, 0.73) |
| | No DM | 39 | 70 | 0.51 (0.34, 0.75) |
| CV Death and Hospitalisation for HF | All Patients | 100 | 138 | 0.71 (0.55, 0.92) |
| | T2DM | 85 | 119 | 0.70 (0.53, 0.92) |
| | No DM | 15 | 19 | 0.79 (0.40, 1.55) |
| Death, All Causes | All Patients | 101 | 146 | 0.69 (0.53, 0.88) |
| | T2DM | 84 | 113 | 0.74 (0.56, 0.98) |
| | No DM | 17 | 33 | 0.52 (0.29, 0.93) |

Fig. 13

|  | Dapagliflozin (N=2152) | Placebo (N=2152) | HR/RR* (95%CI) | P-value |
|---|---|---|---|---|
| Pre-specified exploratory endpoint | | | | |
| Time to 1st heart failure hospitalization | 37 (1.7%) | 71 (3.3%) | 0.51 (0.34, 0.76) | 0.0007 |
| Post hoc exploratory endpoint** | | | | |
| 1 heart failure hospitalization | 30 | 55 | 0.45* (0.24, 0.87) | |
| 2 heart failure hospitalizations | 5 | 12 | | |
| ≥3 heart failure hospitalizations | 2 | 4 | | |

Fig. 16

METHODS OF TREATING CHRONIC KIDNEY DISEASE WITH DAPAGLIFLOZIN

CROSS-REFERENCE TO RELATED APPLICATIONS

This application is a continuation application of and claims the benefit of priority to U.S. patent application Ser. No. 17/219,992, filed on Apr. 1, 2021, which claims priority from U.S. Provisional Patent Application Nos. 63/057,139 (filed Jul. 27, 2020), 63/070,869 (filed Aug. 27, 2020), 63/082,524 (filed Sep. 24, 2020), 63/093,961 (filed Oct. 20, 2020), 63/119,711 (filed Dec. 1, 2020), 63/152,445 (filed Feb. 23, 2021), and 63/161,629 (filed Mar. 16, 2021), which are hereby incorporated by reference in their entirety.

SUMMARY

Chronic kidney disease (CKD) affects approximately 10% of the adult population worldwide. (Eckardt, K-U et al., Lancet 382(9887):158-169, 2013.) The most common causes of CKD are diabetes, hypertension, and chronic glomerulonephritis. Current treatment for CKD includes the administration of angiotensin-converting enzyme inhibitors (ACE-Is) and angiotensin II-receptor blockers (ARBs), lipid and blood pressure control, as well as tight glucose control in patients with diabetes.

Sodium-glucose co-transporter 2 (SGLT2) is a sodium-dependent renal protein that is responsible for reabsorbing glucose back into the blood. SGLT2 inhibitors are a class of glucose lowering agents used to lower blood glucose in patients with type 2 diabetes (T2D) by inhibiting renal GLT2 proteins. SGLT2 inhibitors thus improve glycemic control with a low risk of hypoglycemia, independent of insulin secretion, providing a reduction in blood pressure, body weight, and levels of uric acid. (Inzucchi et al., Diabetes & Vascular Dis Res. 12(2):90-100, 2015.) SGLT2 inhibitors decrease glucose reabsorption in the kidneys, thereby increasing urinary glucose excretion. (Id.)

The present disclosure is directed to compounds, compositions, and methods for treating chronic kidney disease (CKD) in patients with and without type 2 diabetes (T2D) using sodium glucose co-transporter type 2 (SGLT2) inhibitors, e.g., dapagliflozin.

In some embodiments, the SGLT2 inhibitor, e.g., dapagliflozin, is administered with standard of care CKD agents (such as, e.g., ACE-Is and/or ARBs) in the same or a different composition, at the same or different time.

In some embodiments, the SGLT2 inhibitor, e.g., dapagliflozin, is administered with at least one other therapeutic agent (such as, e.g., an antidiabetic agent) in the same or a different composition, at the same or different time.

In the following description, certain details are set forth in order to provide a thorough understanding of various embodiments. However, one skilled in the art will understand that the disclosed embodiments may be practiced without these details. These and other embodiments will become apparent upon reference to the following detailed description and attached drawings.

BRIEF DESCRIPTION OF THE DRAWINGS

FIG. 2 is a summary table of the final overall enrollment details of DAPA CKD Phase 3 clinical trial.

FIG. 3 is a summary table of the final enrollment details of DAPA CKD Phase 3 clinical trial by demographic group.

FIG. 4 is a summary table of the final enrollment details of DAPA CKD Phase 3 clinical trial by disease status at baseline.

FIG. 5 is a summary table of the final enrollment details of DAPA CKD Phase 3 clinical trial by concomitant medication at baseline.

FIG. 6 is a summary of the effects of dapagliflozin on ≥50% sustained eGFR decline, ESRD, and renal or cardiovascular ("CV") death from the DAPA CKD Phase 3 clinical trial. This table shows the primary composite endpoint, which was a composite of ≥50% sustained eGFR decline, ESRD, and renal or CV death, and each of its components (a=adjudicated).

FIG. 10 summarizes the primary and secondary endpoints from the DAPA CKD phase 3 clinical trial including the secondary endpoint depicting dapagliflozin as superior in reducing events of the renal composite without CV death, dapagliflozin as superior in reducing hospitalisation for HF and CV death, and dapagliflozin as superior in reducing overall death from any cause (as compared to placebo group or patients receiving at least one standard of care CKD agent alone).

FIG. 11 summarizes from the DAPA CKD phase 3 clinical trial the secondary endpoint of dapagliflozin as superior in reducing hospitalisation for HF and CV death and each of its components (as compared to placebo group or patients receiving at least one standard of care CKD agent alone).

FIG. 13 depicts the effect of dapagliflozin on the prespecified primary and secondary composite outcomes in patients with and without diabetes.

FIG. 16 summarizes the DAPA CKD phase 3 clinical trial exploratory endpoints showing that dapagliflozin is superior in reducing time to first, second, or third hospitalisation for HF (as compared to placebo group or patients receiving at least one standard of care CKD agent alone) (* Rate ratio for analysis of recurrent events **Number of patients with 1, 2 or 3 or more HF hospitalizations).

DETAILED DESCRIPTION

Figure 1:
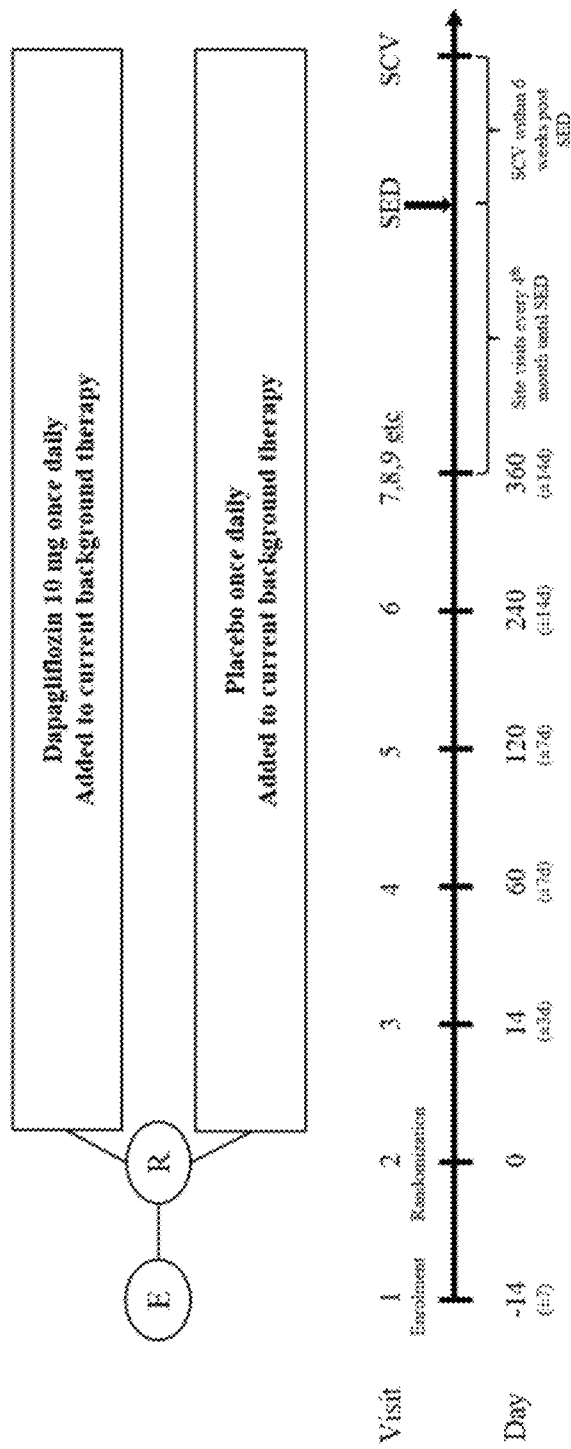
FIG. 1 is a schematic diagram outlining the study procedures, where SED=Study End Date, E=Enrollment, SCV=Study closure visit, and R=Randomization.
Figure 7:
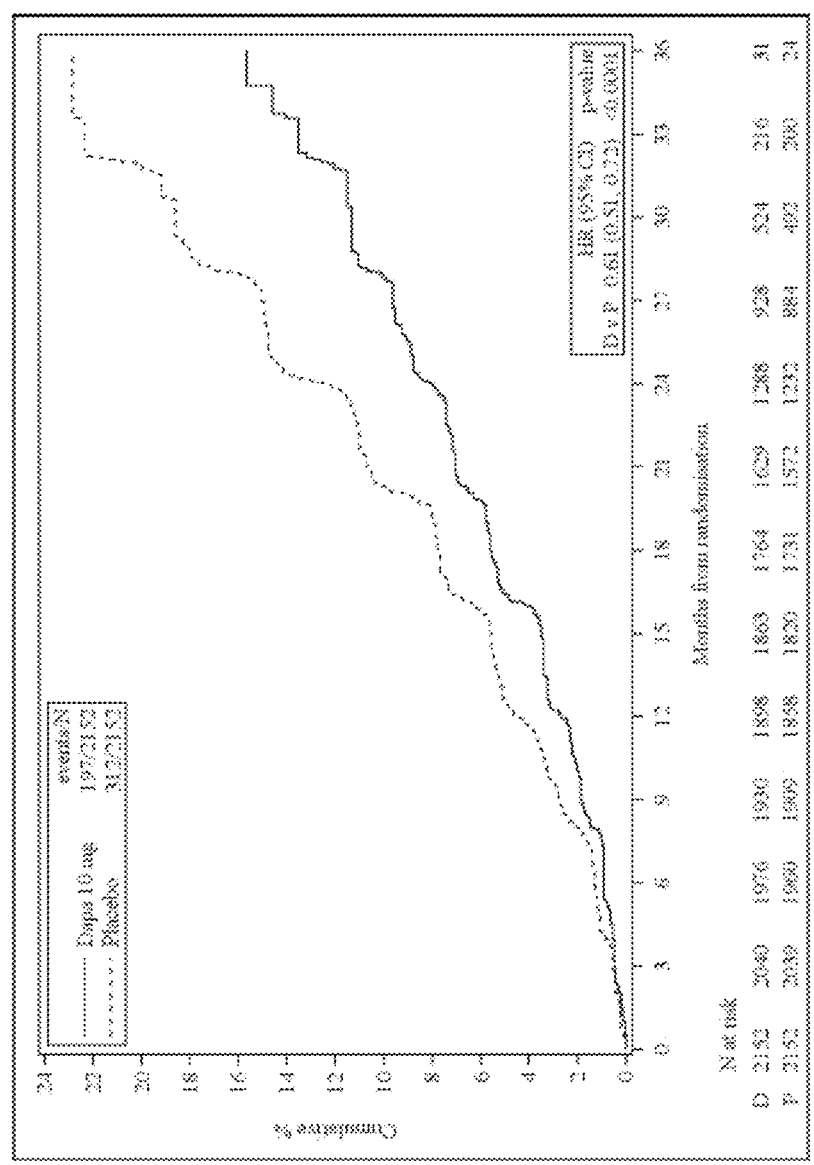
FIG. 7 is a graph depicting the incidence of the primary endpoint of ≥50% sustained eGFR decline, ESRD, and renal or CV death estimated with the use of the Kaplan-Meier method and hazard ratios and 95% confidence intervals were estimated with the use of Cox regression models.

The present disclosure is directed to methods of treating patients with chronic kidney disease, including those with or without Type 2 diabetes (T2D), and/or at least one disease, disorder, or condition associated with CKD, by administering to a patient in need thereof an effective amount of an SGLT2 inhibitor, e.g., dapagliflozin. The present disclosure also provides for methods of treating patients with CKD associated with ischemia, hypertension, chronic glomerulonephritis, or IgA nephropathy.

In some embodiments, the present disclosure includes methods of treating CKD in a patient without Type 2 diabetes (T2D), comprising administering to the patient an SGLT2 inhibitor in an amount effective for treating the patient's CKD. In some embodiments, the methods disclosed herein treat CKD associated with ischemia or hypertension. In some embodiments, the methods disclosed herein treat CKD associated with chronic glomerulonephritis. In some embodiments, the methods disclosed herein treat CKD associated with IgA nephropathy (also known as Berger's disease). In other embodiments, the present disclosure includes methods of treating CKD in a patient with T2D, comprising administering to the patient an SGLT2 inhibitor in an amount effective for treating the patient's CKD.

Also disclosed are methods of preventing or delaying the progression of CKD, cardiovascular (CV) death, or renal death in a patient in need thereof comprising administering to the patient an effective amount of an SGLT2 inhibitor. In some embodiments, the present disclosure includes methods of preventing or delaying the progression of CKD, CV death, or renal death in a patient without T2D, comprising administering to the patient an SGLT2 inhibitor in an amount effective for preventing or delaying the progression of CKD, CV death, or renal death in the patient. In some embodiments, the present disclosure includes methods of preventing or delaying the progression of CKD, CV death, or renal death associated with ischemia, hypertension, chronic glomerulonephritis, or IgA nephropathy in a patient without T2D, comprising administering to the patient an SGLT2 inhibitor in an amount effective for preventing or delaying the progression of CKD, CV death, or renal death in the patient. In other embodiments, the present disclosure includes methods of preventing or delaying the progression of CKD, CV death, or renal death in a patient with T2D, comprising administering to the patient an SGLT2 inhibitor in an amount effective for preventing or delaying the progression of CKD, CV death, or renal death in the patient.

Also disclosed are methods of reducing the incidence of a composite endpoint of ≥50% sustained decline in eGFR, reaching end-stage renal disease (ESRD), CV death, or renal death in a patient with CKD, comprising administering to the patient an effective amount of an SGLT2 inhibitor. In some embodiments, the present disclosure includes methods of reducing the incidence of a composite endpoint of ≥50% sustained decline in eGFR, reaching ESRD, CV death, or renal death in a patient with CKD and without T2D, comprising administering to the patient an effective amount of an SGLT2 inhibitor. In other embodiments, the present disclosure includes methods of reducing the incidence of a composite endpoint of ≥50% sustained decline in eGFR, reaching ESRD, CV death, or renal death in a patient with CKD and T2D, comprising administering to the patient an effective amount of an SGLT2 inhibitor. In some embodiments, the method reduces the incidence of an individual endpoint of ≥50% sustained decline in eGFR in a patient with CKD. In some embodiments, the method reduces the incidence of an individual endpoint of reaching end-stage renal disease (ESRD) in a patient with CKD. In some embodiments, the method reduces the incidence of an individual endpoint of CV death in a patient with CKD. In some embodiments, the method reduces the incidence of an individual endpoint of renal death in a patient with CKD. In some embodiments described above, the incidence of the endpoint in the treatment group (i.e., at least one patient treated with an effective amount of an SGLT2 inhibitor) is reduced relative to placebo. In some embodiments described above, the incidence of the endpoint in the treatment group is reduced relative to an administration regimen where the patient receives at least one standard of care CKD agent alone (i.e., without being treated with an effective amount of an SGLT2 inhibitor).

In some embodiments, the disclosure provides methods of reducing the incidence of a composite endpoint of ≥50% sustained decline in eGFR, reaching end-stage renal disease (ESRD), or renal death in a patient with CKD, comprising administering to the patient an effective amount of an SGLT2 inhibitor. In some embodiments, the present disclosure includes methods of reducing the incidence of a composite endpoint of ≥50% sustained decline in eGFR, reaching ESRD, or renal death in a patient with CKD and without T2D, comprising administering to the patient an effective amount of an SGLT2 inhibitor. In other embodiments, the present disclosure includes methods of reducing the incidence of a composite endpoint of ≥50% sustained decline in eGFR, reaching ESRD, or renal death in a patient with CKD and T2D, comprising administering to the patient an effective amount of an SGLT2 inhibitor. In some embodiments described above, the incidence of the composite endpoint of ≥50% sustained decline in eGFR, reaching end-stage renal disease (ESRD), or renal death in a patient with CKD in the treatment group (i.e., at least one patient treated with an effective amount of an SGLT2 inhibitor) is reduced relative to placebo. In some embodiments described above, the incidence of the composite endpoint of ≥50% sustained decline in eGFR, reaching end-stage renal disease (ESRD), or renal death in a patient with CKD in the treatment group is reduced relative to an administration regimen where the patient receives at least one standard of care CKD agent alone (i.e., without being treated with an effective amount of an SGLT2 inhibitor).

In some embodiments, the disclosure provides methods of reducing the incidence of a composite endpoint of CV death or hospitalization for heart failure (HF) in a patient with CKD, comprising administering to the patient an effective amount of an SGLT2 inhibitor. In some embodiments, the present disclosure includes methods of reducing the incidence of a composite endpoint of CV death or hospitalization for heart failure in a patient with CKD and without T2D, comprising administering to the patient an effective amount of an SGLT2 inhibitor. In other embodiments, the present disclosure includes methods of reducing the incidence of a composite endpoint of CV death or hospitalization for heart failure in a patient with CKD and T2D, comprising administering to the patient an effective amount of an SGLT2 inhibitor. In some embodiments, the method reduces the incidence of hospitalization due to heart failure in a patient with CKD. In some embodiments described above, the incidence of the composite endpoint of CV death or hospitalization for heart failure in the treatment group (i.e., at least one patient treated with an effective amount of an SGLT2 inhibitor) is reduced relative to placebo. In some embodiments described above, the incidence of the composite endpoint of CV death or hospitalization for heart failure in the treatment group is reduced relative to an administration regimen where the patient receives at least one standard of care CKD agent alone (i.e., without being treated with an effective amount of an SGLT2 inhibitor).

Disclosed herein are methods of reducing the incidence of mortality in a patient with CKD, comprising administering to the patient an effective amount of an SGLT2 inhibitor. In some embodiments, the present disclosure includes methods of reducing the incidence of mortality in a patient with CKD and without T2D, comprising administering to the patient an effective amount of an SGLT2 inhibitor. In other embodiments, the present disclosure includes methods of reducing the incidence of mortality in a patient with CKD and T2D, comprising administering to the patient an effective amount of an SGLT2 inhibitor. In some embodiments described above, the incidence of mortality in the treatment group (i.e., at least one patient treated with an effective amount of an SGLT2 inhibitor) is reduced relative to placebo. In some embodiments described above, the incidence of mortality in the treatment group is reduced relative to an administration regimen where the patient receives at least one standard of care CKD agent alone (i.e., without being treated with an effective amount of an SGLT2 inhibitor).

In some embodiments, the method decreases levels of glycated haemoglobin (HbA1c) in CKD patients with T2D from baseline.

In some embodiments, the method reduces the incidence of new diagnosis of T2D in CKD patients without diabetes.

In some embodiments, a patient is identified as having CKD when the patient has eGFR ≥25 and ≤75 mL/min/1.73 m$^2$. In some embodiments, the patient has CKD and albuminuria. In some embodiments, a patient is identified as having albuminuria when the patient has UACR ≥200 and ≤5000 mg/g.

In some embodiments, the method decreases intra-glomerular pressure, hypertension, proteinuria, and/or fluid/sodium overload in patients with CKD. In some embodiments, the method reduces systolic BP of the patient from baseline. In some embodiments, the method reduces systolic BP of the patient from baseline to a greater extent compared to placebo (or as compared to patients receiving at least one standard of care CKD agent alone). In some embodiments, the systolic BP of the patient is measured at day 30 (±7), 120 (±7), 240 (±7), 360 (±7), 480 (±14), and/or 600 (±14).

In some embodiments, the method reduces the number of events of doubling of serum creatinine compared to placebo in patients with CKD (or as compared to patients receiving at least one standard of care CKD agent alone).

In some embodiments, the method reduces the incidence of hyperkalaemia in patients with CKD, wherein the level of serum potassium is >6.0 mmol/L. In some embodiments, the method reduces the incidence of hyperkalaemia in patients with CKD, wherein the serum potassium levels are >5.5 mmol/L. In some embodiments, the method reduces the incidence of hypokalaemia in patients with CKD, wherein the serum potassium levels are <3.5 mmol/L. In some embodiments, the method reduces the incidence of hypokalaemia in patients with CKD, wherein the serum potassium levels are <3.0 mmol/L.

In some embodiments, the method reduces body weight of the patient from baseline. In some embodiments, the method reduces body weight of the patient from baseline to a greater extent compared to placebo (or as compared to patients receiving at least one standard of care CKD agent alone). In some embodiments, the body weight of the patient is measured at day 30 (±7), 120 (±7), 240 (±7), 360 (±7), 480 (±14), and/or 600 (±14).

In some embodiments, the method lowers albuminuria levels in the patient from baseline. In some embodiments, the method lowers albuminuria levels in the patient from baseline to a greater extent compared to placebo (or as compared to patients receiving at least one standard of care CKD agent alone). In some embodiments, the albuminuria levels of the patient is measured at day 30 (±7), 120 (±7), 240 (±7), 360 (±7), 480 (±14), and/or 600 (±14).

In some embodiments, the method reduces the incidence of sustained reduction in kidney function compared to placebo in patients with CKD (or as compared to patients receiving at least one standard of care CKD agent alone). In some embodiments, the method does not reduce eGFR of the patient from baseline. In some embodiments, the method reduces eGFR from baseline to a lesser extent compared to placebo (or as compared to patients receiving at least one standard of care CKD agent alone). In some embodiments, the method reduces the incidence of ≥30% decline in eGFR from baseline compared with placebo in patients with CKD (or as compared to patients receiving at least one standard of care CKD agent alone). In some embodiments, the method reduces the incidence of ≥40% decline in eGFR from baseline compared to placebo in patients with CKD (or as compared to patients receiving at least one standard of care CKD agent alone). In some embodiments, the eGFR of the patient is measured at day 30 (±7), 120 (±7), 240 (±7), 360 (±7), 480 (±14), and/or 600 (±14).

In some embodiments, the method reduces the time to first occurrence of CV death in a patient compared to placebo (or as compared to patients receiving at least one standard of care CKD agent alone). In some embodiments, the time to first occurrence of CV death is measured at day 30 (±7), 120 (±7), 240 (±7), 360 (±7), 480 (±14), and/or 600 (±14).

In some embodiments, the method reduces the time to first occurrence of renal death in a patient compared to placebo (or as compared to patients receiving at least one standard of care CKD agent alone). In some embodiments, the time to first occurrence of renal death is measured at day 30 (±7), 120 (±7), 240 (±7), 360 (±7), 480 (±14), and/or 600 (±14).

In some embodiments, the method reduces the time to first occurrence of hospitalization of a patient for heart failure compared to placebo (or as compared to patients receiving at least one standard of care CKD agent alone). In some embodiments, the time to first occurrence of hospitalization for heart failure is measured at day 30 (±7), 120 (±7), 240 (±7), 360 (±7), 480 (±14), and/or 600 (±14).

In some embodiments, the method reduces the total number of hospitalizations of a patient for heart failure and/or CV death compared to placebo (or as compared to patients receiving at least one standard of care CKD agent alone).

In some embodiments, the method reduces the incidence of the CKD patient reaching CKD 4 (eGFR <30 mL/min/1.73 m$^2$) compared to a placebo (or as compared to patients receiving at least one standard of care CKD agent alone).

In some embodiments, the method reduces the incidence of fatal myocardial infarction in patients with CKD compared to placebo (or as compared to patients receiving at least one standard of care CKD agent alone). In some embodiments, the method reduces the incidence of non-fatal myocardial infarction in patients with CKD compared to placebo (or as compared to patients receiving at least one standard of care CKD agent alone).

In some embodiments, the method reduces the incidence of ischemic stroke in patients with CKD compared to placebo (or as compared to patients receiving at least one standard of care CKD agent alone). In some embodiments, the method reduces the incidence of haemorrhagic stroke in patients with CKD compared to placebo (or as compared to patients receiving at least one standard of care CKD agent alone). In some embodiments, the method reduces the incidence of fatal stroke in patients with CKD compared to placebo (or as compared to patients receiving at least one standard of care CKD agent alone). In some embodiments, the method reduces the incidence of non-fatal stroke in patients with CKD compared to placebo (or as compared to patients receiving at least one standard of care CKD agent alone).

In some embodiments, the method reduces the proportion of patients with worsened NYHA class from baseline compared to placebo (or as compared to patients receiving at least one standard of care CKD agent alone). In some embodiments, the method maintains or improves a patient's NYHA class from baseline compared to placebo (or as compared to patients receiving at least one standard of care CKD agent alone). In some embodiments, the NYHA class of the patient is measured at day 30 (±7), 120 (±7), 240 (±7), 360 (±7), 480 (±14), and/or 600 (±14).

In some embodiments, the method improves the health status of a patient assessed by EQ-5D-5L questionnaire compared to placebo (or as compared to patients receiving at least one standard of care CKD agent alone). In some embodiments, the health status of the patient assessed by the EQ-5D-5L questionnaire is measured at day 30 (±7), 120 (±7), 240 (±7), 360 (±7), 480 (±14), and/or 600 (±14).

In some embodiments, the method improves the health status of a patient assessed by KDQOL 36 questionnaire compared to placebo (or as compared to patients receiving at least one standard of care CKD agent alone). In some embodiments, the health status of the patient assessed by the KDQOL 36 questionnaire is measured at day 30 (±7), 120 (±7), 240 (±7), 360 (±7), 480 (±14), and/or 600 (±14).

Also disclosed herein are methods of preventing or delaying the incidence or onset of T2D in a patient that is prediabetic (i.e., has a glycated hemoglobin ≥5.7% and <6.5%). In some embodiments, the patient is prediabetic with CKD. In other embodiments, the patient is prediabetic with HF. In some other embodiments, the patient is prediabetic with HFrEF. In some embodiments, the patient is prediabetic with no other comorbidity (e.g., CKD, HF, etc.). In some embodiments, the methods disclosed herein reduce the incidence or onset of T2D relative to placebo. In some embodiments, the methods disclosed herein reduce the incidence or onset of T2D relative to a patient taking a standard of care HF or CKD agent. In some embodiments, the reduction of the incidence or onset of T2D is measured by time to first report of a glycated hemoglobin measurement of ≥6.5%. In some embodiments, the methods disclosed herein result in a hazard ratio of less than one for reducing the incidence or onset of T2D relative to placebo. In some embodiments, the methods disclosed herein result in a hazard ratio of less than one for reducing the incidence or onset of T2D relative to a standard of care HF or CKD agent.

In some embodiments, the methods disclosed herein result in a hazard ratio for time to first composite endpoint of ≥50% sustained decline in eGFR, or ESRD and CV or renal death that is less than one in a patient relative to an administration regimen where the patient receives at least one standard of care CKD agent alone. In some methods, the method results in a hazard ratio for time to first composite endpoint of ≥50% sustained decline in eGFR, or ESRD and CV or renal death that is statistically nominally less than one in a patient relative to an administration regimen where the patient receives at least one standard of care CKD agent alone. In some embodiments, the method results in a hazard ratio for time to first composite endpoint of ≥50% sustained decline in eGFR, or ESRD and CV or renal death of approximately 0.61 in a patient relative to an administration regimen where the patient receives at least one standard of care CKD agent alone. In some methods, the method results in a 95% confidence interval for the hazard ratio for time to first composite endpoint of ≥50% sustained decline in eGFR, or ESRD and CV or renal death of approximately 0.51 to 0.72 in a patient relative to an administration regimen where the patient receives at least one standard of care CKD agent alone. In some embodiments, the methods numerically reduce the absolute risk of the composite endpoint of ≥50% sustained decline in eGFR, or ESRD and CV or renal death in a patient relative to an administration regimen where the patient receives at least one standard of care CKD agent alone. In some embodiments, the method results in a nominally significant risk reduction of the composite endpoint of ≥50% sustained decline in eGFR, or ESRD and CV or renal death in a patient relative to an administration regimen where the patient receives at least one standard of care CKD agent alone. In some embodiments, the method results in a numerical reduction in the composite endpoint events of ≥50% sustained decline in eGFR, or ESRD and CV or renal death in a patient relative to an administration regimen where the patient receives at least one standard of care CKD agent alone.

In some embodiments, the methods disclosed herein result in a hazard ratio for time to first composite endpoint of ≥50% sustained decline in eGFR, or ESRD and CV or renal death that is less than one in a patient with T2D relative to an administration regimen where the patient with T2D receives at least one standard of care CKD agent alone. In some methods, the method results in a hazard ratio for time to first composite endpoint of ≥50% sustained decline in eGFR, or ESRD and CV or renal death that is statistically nominally less than one in a patient with T2D relative to an administration regimen where the patient with T2D receives at least one standard of care CKD agent alone. In some embodiments, the method results in a hazard ratio for time to first composite endpoint of ≥50% sustained decline in eGFR, or ESRD and CV or renal death of approximately 0.64 in a patient with T2D relative to an administration regimen where the patient with T2D receives at least one standard of care CKD agent alone. In some methods, the method results in a 95% confidence interval for the hazard ratio for time to first composite endpoint of ≥50% sustained decline in eGFR, or ESRD and CV or renal death of approximately 0.52 to 0.79 in a patient with T2D relative to an administration regimen where the patient with T2D receives at least one standard of care CKD agent alone. In some embodiments, the methods numerically reduce the absolute risk of the composite endpoint of ≥50% sustained decline in eGFR, or ESRD and CV or renal death in a patient with T2D relative to an administration regimen where the patient with T2D receives at least one standard of care CKD agent alone. In some embodiments, the method results in a nominally significant risk reduction of the composite endpoint of ≥50% sustained decline in eGFR, or ESRD and CV or renal death in a patient with T2D relative to an administration regimen where the patient with T2D receives at least one standard of care CKD agent alone. In some embodiments, the method results in a numerical reduction in the composite endpoint events of ≥50% sustained decline in eGFR, or ESRD and CV or renal death in a patient with T2D relative to an administration regimen where the patient with T2D receives at least one standard of care CKD agent alone.

In some embodiments, the methods disclosed herein result in a hazard ratio for time to first composite endpoint of ≥50% sustained decline in eGFR, or ESRD and CV or renal death that is less than one in a patient without T2D relative to an administration regimen where the patient without T2D receives at least one standard of care CKD agent alone. In some methods, the method results in a hazard ratio for time to first composite endpoint of ≥50% sustained decline in eGFR, or ESRD and CV or renal death that is statistically nominally less than one in a patient without T2D relative to an administration regimen where the patient without T2D receives at least one standard of care CKD agent alone. In some embodiments, the method results in a hazard ratio for time to first composite endpoint of ≥50% sustained decline in eGFR, or ESRD and CV or renal death of approximately 0.50 in a patient without T2D relative to an administration regimen where the patient without T2D receives at least one standard of care CKD agent alone. In some methods, the method results in a 95% confidence interval for the hazard ratio for time to first composite endpoint of ≥50% sustained decline in eGFR, or ESRD and CV or renal death of approximately 0.35 to 0.72 in a patient without T2D relative to an administration regimen where the patient without T2D receives at least one standard of care CKD agent alone. In some embodiments, the methods numerically reduce the absolute risk of the composite endpoint of ≥50% sustained decline in eGFR, or ESRD and CV or renal death in a patient without T2D relative to an administration regimen where the patient without T2D receives at least one standard of care CKD agent alone. In some embodiments, the method results in a nominally significant risk reduction of the composite endpoint of ≥50% sustained decline in eGFR, or ESRD and CV or renal death in a patient without T2D relative to an administration regimen where the patient without T2D receives at least one standard of care CKD agent alone. In some embodiments, the method results in a numerical reduction in the composite endpoint events of ≥50% sustained decline in eGFR, or ESRD and CV or renal death in a patient without T2D relative to an administration regimen where the patient without T2D receives at least one standard of care CKD agent alone.

In some embodiments, the methods disclosed herein result in a hazard ratio for time to first composite endpoint of ≥50% sustained decline in eGFR, or ESRD and CV or renal death that is less than one in a patient with a UACR≤1000 mg/g relative to an administration regimen where the patient with a UACR≤1000 mg/g receives at least one standard of care CKD agent alone. In some methods, the method results in a hazard ratio for time to first composite endpoint of ≥50% sustained decline in eGFR, or ESRD and CV or renal death that is statistically nominally less than one in a patient with a UACR≤1000 mg/g relative to an administration regimen where the patient with a UACR≤1000 mg/g receives at least one standard of care CKD agent alone. In some embodiments, the method results in a hazard ratio for time to first composite endpoint of ≥50% sustained decline in eGFR, or ESRD and CV or renal death of approximately 0.54 in a patient with a UACR≤1000 mg/g relative to an administration regimen where the patient with a UACR≤1000 mg/g receives at least one standard of care CKD agent alone. In some methods, the method results in a 95% confidence interval for the hazard ratio for time to first composite endpoint of ≥50% sustained decline in eGFR, or ESRD and CV or renal death of approximately 0.37 to 0.77 in a patient with a UACR≤1000 mg/g relative to an administration regimen where the patient with a UACR≤1000 mg/g receives at least one standard of care CKD agent alone. In some embodiments, the methods numerically reduce the absolute risk of the composite endpoint of ≥50% sustained decline in eGFR, or ESRD and CV or renal death in a patient with a UACR≤1000 mg/g relative to an administration regimen where the patient with a UACR≤1000 mg/g receives at least one standard of care CKD agent alone. In some embodiments, the method results in a nominally significant risk reduction of the composite endpoint of ≥50% sustained decline in eGFR, or ESRD and CV or renal death in a patient with a UACR≤1000 mg/g relative to an administration regimen where the patient with a UACR≤1000 mg/g receives at least one standard of care CKD agent alone. In some embodiments, the method results in a numerical reduction in the composite endpoint events of ≥50% sustained decline in eGFR, or ESRD and CV or renal death in a patient with a UACR≤1000 mg/g relative to an administration regimen where the patient with a UACR≤1000 mg/g receives at least one standard of care CKD agent alone.

In some embodiments, the methods disclosed herein result in a hazard ratio for time to first composite endpoint of ≥50% sustained decline in eGFR, or ESRD and CV or renal death that is less than one in a patient with a UACR>1000 mg/g relative to an administration regimen where the patient with a UACR>1000 mg/g receives at least one standard of care CKD agent alone. In some methods, the method results in a hazard ratio for time to first composite endpoint of ≥50% sustained decline in eGFR, or ESRD and CV or renal death that is statistically nominally less than one in a patient with a UACR>1000 mg/g relative to an administration regimen where the patient with a UACR>1000 mg/g receives at least one standard of care CKD agent alone. In some embodiments, the method results in a hazard ratio for time to first composite endpoint of ≥50%سsustained decline in eGFR, or ESRD and CV or renal death of approximately 0.62 in a patient with a UACR>1000 mg/g relative to an administration regimen where the patient with a UACR>1000 mg/g receives at least one standard of care CKD agent alone. In some methods, the method results in a 95% confidence interval for the hazard ratio for time to first composite endpoint of ≥50% sustained decline in eGFR, or ESRD and CV or renal death of approximately 0.50 to 0.76 in a patient with a UACR>1000 mg/g relative to an administration regimen where the patient with a UACR>1000 mg/g receives at least one standard of care CKD agent alone. In some embodiments, the methods numerically reduce the absolute risk of the composite endpoint of ≥50% sustained decline in eGFR, or ESRD and CV or renal death in a patient with a UACR>1000 mg/g relative to an administration regimen where the patient with a UACR>1000 mg/g receives at least one standard of care CKD agent alone. In some embodiments, the method results in a nominally significant risk reduction of the composite endpoint of ≥50% sustained decline in eGFR, or ESRD and CV or renal death in a patient with a UACR>1000 mg/g relative to an administration regimen where the patient with a UACR>1000 mg/g receives at least one standard of care CKD agent alone. In some embodiments, the method results in a numerical reduction in the composite endpoint events of ≥50% sustained decline in eGFR, or ESRD and CV or renal death in a patient with a UACR>1000 mg/g relative to an administration regimen where the patient with a UACR>1000 mg/g receives at least one standard of care CKD agent alone.

In some embodiments, the methods disclosed herein result in a hazard ratio for time to first composite endpoint of ≥50% sustained decline in eGFR, or ESRD and CV or renal death that is less than one in a patient with a eGFR <45 mL/min/1.73 m$^2$ relative to an administration regimen where the patient with a eGFR <45 mL/min/1.73 m$^2$ receives at least one standard of care CKD agent alone. In some methods, the method results in a hazard ratio for time to first composite endpoint of ≥50% sustained decline in eGFR, or ESRD and CV or renal death that is statistically nominally less than one in a patient with a eGFR <45 mL/min/1.73 m$^2$ relative to an administration regimen where the patient with a eGFR <45 mL/min/1.73 m$^2$ receives at least one standard of care CKD agent alone. In some embodiments, the method results in a hazard ratio for time to first composite endpoint of ≥50% sustained decline in eGFR, or ESRD and CV or renal death of approximately 0.63 in a patient with a eGFR <45 mL/min/1.73 m$^2$ relative to an administration regimen where the patient with a eGFR <45 mL/min/1.73 m$^2$ receives at least one standard of care CKD agent alone. In some methods, the method results in a 95% confidence interval for the hazard ratio for time to first composite endpoint of ≥50% sustained decline in eGFR, or ESRD and CV or renal death of approximately 0.51 to 0.78 in a patient with a eGFR <45 mL/min/1.73 m$^2$ relative to an administration regimen where the patient with a eGFR <45 mL/min/1.73 m$^2$ receives at least one standard of care CKD agent alone. In some embodiments, the methods numerically reduce the absolute risk of the composite endpoint of ≥50% sustained decline in eGFR, or ESRD and CV or renal death in a patient with a eGFR <45 mL/min/1.73 m$^2$ relative to an administration regimen where the patient with a eGFR <45 mL/min/1.73 m$^2$ receives at least one standard of care CKD agent alone. In some embodiments, the method results in a nominally significant risk reduction of the composite endpoint of ≥50% sustained decline in eGFR, or ESRD and CV or renal death in a patient with a eGFR <45 mL/min/1.73 m$^2$ relative to an administration regimen where the patient with a eGFR <45 mL/min/1.73 m$^2$ receives at least one standard of care CKD agent alone. In some embodiments, the method results in a numerical reduction in the composite endpoint events of ≥50% sustained decline in eGFR, or ESRD and CV or renal death in a patient with a eGFR <45 mL/min/1.73 m$^2$ relative to an administration regimen where the patient with a eGFR <45 mL/min/1.73 m$^2$ receives at least one standard of care CKD agent alone.

In some embodiments, the methods disclosed herein result in a hazard ratio for time to first composite endpoint of ≥50% sustained decline in eGFR, or ESRD and CV or renal death that is less than one in a patient with a eGFR ≥45 mL/min/1.73 m$^2$ relative to an administration regimen where the patient with a eGFR ≥45 mL/min/1.73 m$^2$ receives at least one standard of care CKD agent alone. In some methods, the method results in a hazard ratio for time to first composite endpoint of ≥50% sustained decline in eGFR, or ESRD and CV or renal death that is statistically nominally less than one in a patient with a eGFR ≥45 mL/min/1.73 m$^2$ relative to an administration regimen where the patient with a eGFR ≥45 mL/min/1.73 m$^2$ receives at least one standard of care CKD agent alone. In some embodiments, the method results in a hazard ratio for time to first composite endpoint of ≥50% sustained decline in eGFR, or ESRD and CV or renal death of approximately 0.49 in a patient with a eGFR ≥45 mL/min/1.73 m$^2$ relative to an administration regimen where the patient with a eGFR ≥45 mL/min/1.73 m$^2$ receives at least one standard of care CKD agent alone. In some methods, the method results in a 95% confidence interval for the hazard ratio for time to first composite endpoint of ≥50% sustained decline in eGFR, or ESRD and CV or renal death of approximately 0.34 to 0.69 in a patient with a eGFR ≥45 mL/min/1.73 m$^2$ relative to an administration regimen where the patient with a eGFR ≥45 mL/min/1.73 m$^2$ receives at least one standard of care CKD agent alone. In some embodiments, the methods numerically reduce the absolute risk of the composite endpoint of ≥50% sustained decline in eGFR, or ESRD and CV or renal death in a patient with a eGFR ≥45 mL/min/1.73 m$^2$ relative to an administration regimen where the patient with a eGFR ≥45 mL/min/1.73 m² receives at least one standard of care CKD agent alone. In some embodiments, the method results in a nominally significant risk reduction of the composite endpoint of ≥50% sustained decline in eGFR, or ESRD and CV or renal death in a patient with a eGFR ≥45 mL/min/1.73 m² relative to an administration regimen where the patient with a eGFR ≥45 mL/min/1.73 m² receives at least one standard of care CKD agent alone. In some embodiments, the method results in a numerical reduction in the composite endpoint events of ≥50% sustained decline in eGFR, or ESRD and CV or renal death in a patient with a eGFR ≥45 mL/min/1.73 m² relative to an administration regimen where the patient with a eGFR ≥45 mL/min/1.73 m² receives at least one standard of care CKD agent alone.

In some embodiments, the methods disclosed herein result in a hazard ratio for time to ≥50% sustained decline in eGFR that is less than one in a patient relative to an administration regimen where the patient receives at least one standard of care CKD agent alone. In some methods, the method results in a hazard ratio for time to ≥50% sustained decline in eGFR that is statistically nominally less than one in a patient relative to an administration regimen where the patient receives at least one standard of care CKD agent alone. In some embodiments, the method results in a hazard ratio for time to ≥50% sustained decline in eGFR of approximately 0.53 in a patient relative to an administration regimen where the patient receives at least one standard of care CKD agent alone. In some methods, the method results in a 95% confidence interval for the hazard ratio for time to ≥50% sustained decline in eGFR of approximately 0.42 to 0.67 in a patient relative to an administration regimen where the patient receives at least one standard of care CKD agent alone. In some embodiments, the methods numerically reduce the absolute risk of ≥50% sustained decline in eGFR in a patient relative to an administration regimen where the patient receives at least one standard of care CKD agent alone. In some embodiments, the method results in a nominally significant risk reduction of ≥50% sustained decline in eGFR in a patient relative to an administration regimen where the patient receives at least one standard of care CKD agent alone. In some embodiments, the method results in a numerical reduction in the ≥50% sustained decline in eGFR in a patient relative to an administration regimen where the patient receives at least one standard of care CKD agent alone.

In some embodiments, the methods disclosed herein result in a hazard ratio for time to ESRD that is less than one in a patient relative to an administration regimen where the patient receives at least one standard of care CKD agent alone. In some methods, the method results in a hazard ratio for time to ESRD that is statistically nominally less than one in a patient relative to an administration regimen where the patient receives at least one standard of care CKD agent alone. In some embodiments, the method results in a hazard ratio for time ESRD of approximately 0.64 in a patient relative to an administration regimen where the patient receives at least one standard of care CKD agent alone. In some methods, the method results in a 95% confidence interval for the hazard ratio for time to ESRD of approximately 0.50 to 0.82 in a patient relative to an administration regimen where the patient receives at least one standard of care CKD agent alone. In some embodiments, the methods numerically reduce the absolute risk of ESRD in a patient relative to an administration regimen where the patient receives at least one standard of care CKD agent alone. In some embodiments, the method results in a nominally significant risk reduction of ESRD in a patient relative to an administration regimen where the patient receives at least one standard of care CKD agent alone. In some embodiments, the method results in a numerical reduction in ESRD in a patient relative to an administration regimen where the patient receives at least one standard of care CKD agent alone.

In some embodiments, the methods disclosed herein result in a hazard ratio for time to CV death that is less than one in a patient relative to an administration regimen where the patient receives at least one standard of care CKD agent alone. In some methods, the method results in a hazard ratio for time to CV death that is statistically nominally less than one in a patient relative to an administration regimen where the patient receives at least one standard of care CKD agent alone. In some embodiments, the method results in a hazard ratio for time to CV death of approximately 0.81 in a patient relative to an administration regimen where the patient receives at least one standard of care CKD agent alone. In some methods, the method results in a 95% confidence interval for the hazard ratio for time to CV death of approximately 0.58 to 1.12 in a patient relative to an administration regimen where the patient receives at least one standard of care CKD agent alone. In some embodiments, the methods numerically reduce the absolute risk of CV death in a patient relative to an administration regimen where the patient receives at least one standard of care CKD agent alone. In some embodiments, the method results in a nominally significant risk reduction of CV death in a patient relative to an administration regimen where the patient receives at least one standard of care CKD agent alone. In some embodiments, the method results in a numerical reduction in CV death in a patient relative to an administration regimen where the patient receives at least one standard of care CKD agent alone.

In some embodiments, the methods disclosed herein result in a hazard ratio for time to first composite endpoint of ≥50% sustained decline in eGFR, or ESRD and renal death that is less than one in a patient relative to an administration regimen where the patient receives at least one standard of care CKD agent alone. In some methods, the method results in a hazard ratio for time to first composite endpoint of ≥50% sustained decline in eGFR, or ESRD and renal death that is statistically nominally less than one in a patient relative to an administration regimen where the patient receives at least one standard of care CKD agent alone. In some embodiments, the method results in a hazard ratio for time to first composite endpoint of ≥50% sustained decline in eGFR, or ESRD and renal death of approximately 0.56 in a patient relative to an administration regimen where the patient receives at least one standard of care CKD agent alone. In some methods, the method results in a 95% confidence interval for the hazard ratio for time to first composite endpoint of ≥50% sustained decline in eGFR, or ESRD and renal death of approximately 0.45 to 0.68 in a patient relative to an administration regimen where the patient receives at least one standard of care CKD agent alone. In some embodiments, the methods numerically reduce the absolute risk of the composite endpoint of ≥50% sustained decline in eGFR, or ESRD and renal death in a patient relative to an administration regimen where the patient receives at least one standard of care CKD agent alone. In some embodiments, the method results in a nominally significant risk reduction of the composite endpoint of ≥50% sustained decline in eGFR, or ESRD and renal death in a patient relative to an administration regimen where the patient receives at least one standard of care CKD agent alone. In some embodiments, the method results in a numerical reduction in the composite endpoint events of ≥50% sustained decline in eGFR, or ESRD and renal death in a patient relative to an administration regimen where the patient receives at least one standard of care CKD agent alone.

In some embodiments, the methods disclosed herein result in a hazard ratio for time to first composite endpoint of ≥50% sustained decline in eGFR, or ESRD and renal death that is less than one in a patient with T2D relative to an administration regimen where the patient with T2D receives at least one standard of care CKD agent alone. In some methods, the method results in a hazard ratio for time to first composite endpoint of ≥50% sustained decline in eGFR, or ESRD and renal death that is statistically nominally less than one in a patient with T2D relative to an administration regimen where the patient with T2D receives at least one standard of care CKD agent alone. In some embodiments, the method results in a hazard ratio for time to first composite endpoint of ≥50% sustained decline in eGFR, or ESRD and renal death of approximately 0.57 in a patient with T2D relative to an administration regimen where the patient with T2D receives at least one standard of care CKD agent alone. In some methods, the method results in a 95% confidence interval for the hazard ratio for time to first composite endpoint of ≥50% sustained decline in eGFR, or ESRD and renal death of approximately 0.45 to 0.73 in a patient with T2D relative to an administration regimen where the patient with T2D receives at least one standard of care CKD agent alone. In some embodiments, the methods numerically reduce the absolute risk of the composite endpoint of ≥50% sustained decline in eGFR, or ESRD and renal death in a patient with T2D relative to an administration regimen where the patient with T2D receives at least one standard of care CKD agent alone. In some embodiments, the method results in a nominally significant risk reduction of the composite endpoint of ≥50% sustained decline in eGFR, or ESRD and renal death in a patient with T2D relative to an administration regimen where the patient with T2D receives at least one standard of care CKD agent alone. In some embodiments, the method results in a numerical reduction in the composite endpoint events of ≥50% sustained decline in eGFR, or ESRD and renal death in a patient with T2D relative to an administration regimen where the patient with T2D receives at least one standard of care CKD agent alone.

In some embodiments, the methods disclosed herein result in a hazard ratio for time to first composite endpoint of ≥50% sustained decline in eGFR, or ESRD and renal death that is less than one in a patient without T2D relative to an administration regimen where the patient without T2D receives at least one standard of care CKD agent alone. In some methods, the method results in a hazard ratio for time to first composite endpoint of ≥50% sustained decline in eGFR, or ESRD and renal death that is statistically nominally less than one in a patient without T2D relative to an administration regimen where the patient without T2D receives at least one standard of care CKD agent alone. In some embodiments, the method results in a hazard ratio for time to first composite endpoint of ≥50% sustained decline in eGFR, or ESRD and renal death of approximately 0.51 in a patient without T2D relative to an administration regimen where the patient without T2D receives at least one standard of care CKD agent alone. In some methods, the method results in a 95% confidence interval for the hazard ratio for time to first composite endpoint of ≥50% sustained decline in eGFR, or ESRD and renal death of approximately 0.34 to 0.75 in a patient without T2D relative to an administration regimen where the patient without T2D receives at least one standard of care CKD agent alone. In some embodiments, the methods numerically reduce the absolute risk of the composite endpoint of ≥50% sustained decline in eGFR, or ESRD and renal death in a patient without T2D relative to an administration regimen where the patient without T2D receives at least one standard of care CKD agent alone. In some embodiments, the method results in a nominally significant risk reduction of the composite endpoint of ≥50% sustained decline in eGFR, or ESRD and renal death in a patient without T2D relative to an administration regimen where the patient without T2D receives at least one standard of care CKD agent alone. In some embodiments, the method results in a numerical reduction in the composite endpoint events of ≥50% sustained decline in eGFR, or ESRD and renal death in a patient without T2D relative to an administration regimen where the patient without T2D receives at least one standard of care CKD agent alone.

In some embodiments, the methods disclosed herein result in a hazard ratio for time to first composite endpoint of ≥50% sustained decline in eGFR, or ESRD and renal death that is less than one in a patient with eGFR <30, relative to an administration regimen where the patient with eGFR <30 receives at least one standard of care CKD agent alone. In some methods, the method results in a hazard ratio for time to first composite endpoint of ≥50% sustained decline in eGFR, or ESRD and renal death that is statistically nominally less than one in a patient with eGFR <30 relative to an administration regimen where the patient with eGFR <30 receives at least one standard of care CKD agent alone. In some embodiments, the method results in a hazard ratio for time to first composite endpoint of ≥50% sustained decline in eGFR, or ESRD and renal death of approximately 0.73 in a patient with eGFR <30 relative to an administration regimen where the patient with eGFR <30 receives at least one standard of care CKD agent alone. In some methods, the method results in a 95% confidence interval for the hazard ratio for time to first composite endpoint of ≥50% sustained decline in eGFR, or ESRD and renal death of approximately 0.53 to 1.02 in a patient with eGFR <30 relative to an administration regimen where the patient with eGFR <30 receives at least one standard of care CKD agent alone. In some embodiments, the methods numerically reduce the absolute risk of the composite endpoint of ≥50% sustained decline in eGFR, or ESRD and renal death in a patient with eGFR <30 relative to an administration regimen where the patient with eGFR <30 receives at least one standard of care CKD agent alone. In some embodiments, the method results in a nominally significant risk reduction of the composite endpoint of ≥50% sustained decline in eGFR, or ESRD and renal death in a patient with eGFR <30 relative to an administration regimen where the patient with eGFR <30 receives at least one standard of care CKD agent alone. In some embodiments, the method results in a numerical reduction in the composite endpoint events of ≥50% sustained decline in eGFR, or ESRD and renal death in a patient with eGFR <30 relative to an administration regimen where the patient with eGFR <30 receives at least one standard of care CKD agent alone.

In some embodiments, the methods disclosed herein result in a hazard ratio for time to first composite endpoint of ≥50% sustained decline in eGFR, or ESRD and renal death that is less than one in a patient with eGFR ≥30, relative to an administration regimen where the patient with eGFR ≥30 receives at least one standard of care CKD agent alone. In some methods, the method results in a hazard ratio for time to first composite endpoint of ≥50% sustained decline in eGFR, or ESRD and renal death that is statistically nominally less than one in a patient with eGFR ≥30 relative to an administration regimen where the patient with eGFR ≥30 receives at least one standard of care CKD agent alone. In some embodiments, the method results in a hazard ratio for time to first composite endpoint of ≥50% sustained decline in eGFR, or ESRD and renal death of approximately 0.58 in a patient with eGFR ≥30 relative to an administration regimen where the patient with eGFR ≥30 receives at least one standard of care CKD agent alone. In some methods, the method results in a 95% confidence interval for the hazard ratio for time to first composite endpoint of ≥50% sustained decline in eGFR, or ESRD and renal death of approximately 0.47 to 0.71 in a patient with eGFR ≥30 relative to an administration regimen where the patient with eGFR ≥30 receives at least one standard of care CKD agent alone. In some embodiments, the methods numerically reduce the absolute risk of the composite endpoint of ≥50% sustained decline in eGFR, or ESRD and renal death in a patient with eGFR ≥30 relative to an administration regimen where the patient with eGFR ≥30 receives at least one standard of care CKD agent alone. In some embodiments, the method results in a nominally significant risk reduction of the composite endpoint of ≥50% sustained decline in eGFR, or ESRD and renal death in a patient with eGFR ≥30 relative to an administration regimen where the patient with eGFR ≥30 receives at least one standard of care CKD agent alone. In some embodiments, the method results in a numerical reduction in the composite endpoint events of ≥50% sustained decline in eGFR, or ESRD and renal death in a patient with eGFR ≥30 relative to an administration regimen where the patient with eGFR ≥30 receives at least one standard of care CKD agent alone.

In some embodiments, the methods disclosed herein result in a hazard ratio for time to first composite endpoint of CV death and hospitalization for heart failure that is less than one in a patient relative to an administration regimen where the patient receives at least one standard of care CKD agent alone. In some methods, the method results in a hazard ratio for time to first composite endpoint of CV death and hospitalization for heart failure that is statistically nominally less than one in a patient relative to an administration regimen where the patient receives at least one standard of care CKD agent alone. In some embodiments, the method results in a hazard ratio for time to first composite endpoint of CV death and hospitalization for heart failure of approximately 0.71 in a patient relative to an administration regimen where the patient receives at least one standard of care CKD agent alone. In some methods, the method results in a 95% confidence interval for the hazard ratio for time to first composite endpoint of CV death and hospitalization for heart failure of approximately 0.55 to 0.92 in a patient relative to an administration regimen where the patient receives at least one standard of care CKD agent alone. In some embodiments, the methods numerically reduce the absolute risk of the composite endpoint of CV death and hospitalization for heart failure in a patient relative to an administration regimen where the patient receives at least one standard of care CKD agent alone. In some embodiments, the method results in a nominally significant risk reduction of the composite endpoint of CV death and hospitalization for heart failure in a patient relative to an administration regimen where the patient receives at least one standard of care CKD agent alone. In some embodiments, the method results in a numerical reduction in the composite endpoint events CV death and hospitalization for heart failure in a patient relative to an administration regimen where the patient receives at least one standard of care CKD agent alone.

In some embodiments, the methods disclosed herein result in a hazard ratio for time to first composite endpoint of CV death and hospitalization for heart failure that is less than one in a patient with T2D relative to an administration regimen where the patient with T2D receives at least one standard of care CKD agent alone. In some methods, the method results in a hazard ratio for time to first composite endpoint of CV death and hospitalization for heart failure that is statistically nominally less than one in a patient with T2D relative to an administration regimen where the patient with T2D receives at least one standard of care CKD agent alone. In some embodiments, the method results in a hazard ratio for time to first composite endpoint of CV death and hospitalization for heart failure of approximately 0.70 in a patient with T2D relative to an administration regimen where the patient with T2D receives at least one standard of care CKD agent alone. In some methods, the method results in a 95% confidence interval for the hazard ratio for time to first composite endpoint of CV death and hospitalization for heart failure of approximately 0.53 to 0.92 in a patient with T2D relative to an administration regimen where the patient with T2D receives at least one standard of care CKD agent alone. In some embodiments, the methods numerically reduce the absolute risk of the composite endpoint of CV death and hospitalization for heart failure in a patient with T2D relative to an administration regimen where the patient with T2D receives at least one standard of care CKD agent alone. In some embodiments, the method results in a nominally significant risk reduction of the composite endpoint of CV death and hospitalization for heart failure in a patient with T2D relative to an administration regimen where the patient with T2D receives at least one standard of care CKD agent alone. In some embodiments, the method results in a numerical reduction in the composite endpoint events CV death and hospitalization for heart failure in a patient with T2D relative to an administration regimen where the patient with T2D receives at least one standard of care CKD agent alone.

In some embodiments, the methods disclosed herein result in a hazard ratio for time to first composite endpoint of CV death and hospitalization for heart failure that is less than one in a patient without T2D relative to an administration regimen where the patient without T2D receives at least one standard of care CKD agent alone. In some methods, the method results in a hazard ratio for time to first composite endpoint of CV death and hospitalization for heart failure that is statistically nominally less than one in a patient without T2D relative to an administration regimen where the patient without T2D receives at least one standard of care CKD agent alone. In some embodiments, the method results in a hazard ratio for time to first composite endpoint of CV death and hospitalization for heart failure of approximately 0.79 in a patient without T2D relative to an administration regimen where the patient without T2D receives at least one standard of care CKD agent alone. In some methods, the method results in a 95% confidence interval for the hazard ratio for time to first composite endpoint of CV death and hospitalization for heart failure of approximately 0.40 to 1.55 in a patient without T2D relative to an administration regimen where the patient without T2D receives at least one standard of care CKD agent alone. In some embodiments, the methods numerically reduce the absolute risk of the composite endpoint of CV death and hospitalization for heart failure in a patient without T2D relative to an administration regimen where the patient without T2D receives at least one standard of care CKD agent alone. In some embodiments, the method results in a nominally significant risk reduction of the composite endpoint of CV death and hospitalization for heart failure in a patient without T2D relative to an administration regimen where the patient without T2D receives at least one standard of care CKD agent alone. In some embodiments, the method results in a numerical reduction in the composite endpoint events CV death and hospitalization for heart failure in a patient without T2D relative to an administration regimen where the patient without T2D receives at least one standard of care CKD agent alone.

In some embodiments, the methods disclosed herein result in a hazard ratio for time to death from all causes that is less than one in a patient relative to an administration regimen where the patient receives at least one standard of care CKD agent alone. In some methods, the method results in a hazard ratio for time to death from all causes that is statistically nominally less than one in a patient relative to an administration regimen where the patient receives at least one standard of care CKD agent alone. In some embodiments, the method results in a hazard ratio for time to death from all causes of approximately 0.69 in a patient relative to an administration regimen where the patient receives at least one standard of care CKD agent alone. In some methods, the method results in a 95% confidence interval for the hazard ratio for time to death from all causes of approximately 0.53 to 0.88 in a patient relative to an administration regimen where the patient receives at least one standard of care CKD agent alone. In some embodiments, the methods numerically reduce the absolute risk of death from all causes in a patient relative to an administration regimen where the patient receives at least one standard of care CKD agent alone. In some embodiments, the method results in a nominally significant risk reduction of death from all causes in a patient relative to an administration regimen where the patient receives at least one standard of care CKD agent alone. In some embodiments, the method results in a numerical reduction in death from all causes in a patient relative to an administration regimen where the patient receives at least one standard of care CKD agent alone.

In some embodiments, the methods disclosed herein result in a hazard ratio for time to death from all causes that is less than one in a patient with T2D relative to an administration regimen where the patient with T2D receives at least one standard of care CKD agent alone. In some methods, the method results in a hazard ratio for time to death from all causes that is statistically nominally less than one in a patient with T2D relative to an administration regimen where the patient with T2D receives at least one standard of care CKD agent alone. In some embodiments, the method results in a hazard ratio for time to death from all causes of approximately 0.74 in a patient with T2D relative to an administration regimen where the patient with T2D receives at least one standard of care CKD agent alone. In some methods, the method results in a 95% confidence interval for the hazard ratio for time to death from all causes of approximately 0.56 to 0.98 in a patient with T2D relative to an administration regimen where the patient with T2D receives at least one standard of care CKD agent alone. In some embodiments, the methods numerically reduce the absolute risk of death from all causes in a patient with T2D relative to an administration regimen where the patient with T2D receives at least one standard of care CKD agent alone. In some embodiments, the method results in a nominally significant risk reduction of death from all causes in a patient with T2D relative to an administration regimen where the patient with T2D receives at least one standard of care CKD agent alone. In some embodiments, the method results in a numerical reduction in death from all causes in a patient with T2D relative to an administration regimen where the patient with T2D receives at least one standard of care CKD agent alone.

In some embodiments, the methods disclosed herein result in a hazard ratio for time to death from all causes that is less than one in a patient without T2D relative to an administration regimen where the patient without T2D receives at least one standard of care CKD agent alone. In some methods, the method results in a hazard ratio for time to death from all causes that is statistically nominally less than one in a patient without T2D relative to an administration regimen where the patient without T2D receives at least one standard of care CKD agent alone. In some embodiments, the method results in a hazard ratio for time to death from all causes of approximately 0.52 in a patient without T2D relative to an administration regimen where the patient without T2D receives at least one standard of care CKD agent alone. In some methods, the method results in a 95% confidence interval for the hazard ratio for time to death from all causes of approximately 0.29 to 0.93 in a patient without T2D relative to an administration regimen where the patient without T2D receives at least one standard of care CKD agent alone. In some embodiments, the methods numerically reduce the absolute risk of death from all causes in a patient without T2D relative to an administration regimen where the patient without T2D receives at least one standard of care CKD agent alone. In some embodiments, the method results in a nominally significant risk reduction of death from all causes in a patient without T2D relative to an administration regimen where the patient without T2D receives at least one standard of care CKD agent alone. In some embodiments, the method results in a numerical reduction in death from all causes in a patient without T2D relative to an administration regimen where the patient without T2D receives at least one standard of care CKD agent alone.

In some embodiments, the methods disclosed herein result in a hazard ratio for time to first composite endpoint of chronic dialysis, kidney transplantation, or renal death that is less than one in a patient relative to an administration regimen where the patient receives at least one standard of care CKD agent alone. In some methods, the method results in a hazard ratio for time to first composite endpoint of chronic dialysis, kidney transplantation, or renal death that is statistically nominally less than one in a patient relative to an administration regimen where the patient receives at least one standard of care CKD agent alone. In some embodiments, the method results in a hazard ratio for time to first composite endpoint of chronic dialysis, kidney transplantation, or renal death of approximately 0.66 in a patient relative to an administration regimen where the patient receives at least one standard of care CKD agent alone. In some methods, the method results in a 95% confidence interval for the hazard ratio for time to first composite endpoint of chronic dialysis, kidney transplantation, or renal death of approximately 0.49 to 0.90 in a patient relative to an administration regimen where the patient receives at least one standard of care CKD agent alone. In some embodiments, the methods numerically reduce the absolute risk of the composite endpoint of chronic dialysis, kidney transplantation, or renal death in a patient relative to an administration regimen where the patient receives at least one standard of care CKD agent alone. In some embodiments, the method results in a nominally significant risk reduction of the composite endpoint of chronic dialysis, kidney transplantation, or renal death in a patient relative to an administration regimen where the patient receives at least one standard of care CKD agent alone. In some embodiments, the method results in a numerical reduction in the composite endpoint events of chronic dialysis, kidney transplantation, or renal death in a patient relative to an administration regimen where the patient receives at least one standard of care CKD agent alone.

In some embodiments, the methods disclosed herein result in a hazard ratio for time to first hospitalization for HF that is less than one in a patient relative to an administration regimen where the patient receives at least one standard of care CKD agent alone. In some methods, the method results in a hazard ratio for time to first hospitalization for HF that is statistically nominally less than one in a patient relative to an administration regimen where the patient receives at least one standard of care CKD agent alone. In some embodiments, the method results in a hazard ratio for time to first hospitalization for HF of approximately 0.51 in a patient relative to an administration regimen where the patient receives at least one standard of care CKD agent alone. In some methods, the method results in a 95% confidence interval for the hazard ratio for time to first hospitalization for HF of approximately 0.34 to 0.76 in a patient relative to an administration regimen where the patient receives at least one standard of care CKD agent alone. In some embodiments, the methods numerically reduce the risk of time to first hospitalization for HF in a patient relative to an administration regimen where the patient receives at least one standard of care CKD agent alone. In some embodiments, the method results in a nominally significant risk reduction of the time to first hospitalization for HF in a patient relative to an administration regimen where the patient receives at least one standard of care CKD agent alone. In some embodiments, the method results in a numerical reduction in the risk of time to first hospitalization for HF in a patient relative to an administration regimen where the patient receives at least one standard of care CKD agent alone.

In some embodiments, the methods disclosed herein result in a hazard ratio for time to first composite endpoint of ≥50% sustained decline in eGFR, or ESRD and CV or renal death that is less than one in a patient with IgA nephropathy relative to an administration regimen where the patient with IgA nephropathy receives at least one standard of care CKD agent alone. In some methods, the method results in a hazard ratio for time to first composite endpoint of ≥50% sustained decline in eGFR, or ESRD and CV or renal death that is statistically nominally less than one in a patient with IgA nephropathy relative to an administration regimen where the patient with IgA nephropathy receives at least one standard of care CKD agent alone. In some embodiments, the method results in a hazard ratio for time to first composite endpoint of ≥50% sustained decline in eGFR, or ESRD and CV or renal death of approximately 0.29 in a patient with IgA nephropathy relative to an administration regimen where the patient with IgA nephropathy receives at least one standard of care CKD agent alone. In some methods, the method results in a 95% confidence interval for the hazard ratio for time to first composite endpoint of ≥50% sustained decline in eGFR, or ESRD and CV or renal death of approximately 0.12 to 0.73 in a patient with IgA nephropathy relative to an administration regimen where the patient with IgA nephropathy receives at least one standard of care CKD agent alone. In some embodiments, the methods numerically reduce the risk of time to first composite endpoint of ≥50% sustained decline in eGFR, or ESRD and CV or renal death in a patient with IgA nephropathy relative to an administration regimen where the patient with IgA nephropathy receives at least one standard of care CKD agent alone. In some embodiments, the method results in a nominally significant risk reduction of the time to first composite endpoint of ≥50% sustained decline in eGFR, or ESRD and CV or renal death in a patient with IgA nephropathy relative to an administration regimen where the patient with IgA nephropathy receives at least one standard of care CKD agent alone. In some embodiments, the method results in a numerical reduction in the risk of time to first composite endpoint of ≥50% sustained decline in eGFR, or ESRD and CV or renal death in a patient with IgA nephropathy relative to an administration regimen where the patient with IgA nephropathy receives at least one standard of care CKD agent alone.

Also disclosed herein is AZD9977, 2-{(3S)-7-Fluoro-4-[(3-oxo-3,4-dihydro-2H-1, 4-benzoxazin-6-yl)carbonyl]-3,4-dihydro-2H-1,4-benzoxazin-3-yl}-N-methylacetamide, disclosed in WO 2016/001631, and having the following structure:

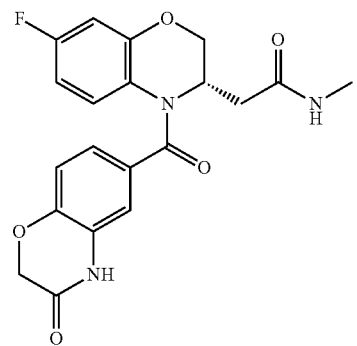 [SMILES: CNC(=O)C[C@H]1COc2cc(F)ccc2N1C(=O)c1ccc2c(c1)NC(=O)CO2]

In some embodiments, disclosed is a method of treating CKD comprising administering to a patient in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in the treatment of CKD in a patient, wherein said treatment comprises the separate, sequential or simultaneous administration of AZD9977 and an SGLT2 inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in the treatment of CKD in a patient, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In some embodiments, disclosed is a method of reducing the rate of progression of renal failure and/or renal death and/or CV death in patients with CKD comprising administering to a patient in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof. In at least one embodiment, renal failure may be defined, for example, as a ≥40% decline in eGFR or ESRD. In some embodiments, the patients with CKD may, for example, have an eGFR ranging from 15-89 ml/min/1.73 m². In other embodiments, the patients with CKD may, for example, have an eGFR ranging from 15-59 ml/min/1.73 m². In some embodiments, the patients with CKD may, for example, be at high risk of hyperkalemia (i.e., have T2D and/or have an eGFR ranging from 15-59 ml/min/1.73 m²).

In some embodiments, disclosed is AZD9977 or a pharmaceutically acceptable salt thereof for use in reducing the rate of progression of renal failure and/or renal death and/or CV death in patients with CKD, wherein said treatment comprises the separate, sequential or simultaneous administration of AZD9977 and an SGLT2 inhibitor to said patient. In some embodiments, the SGLT2 inhibitor is dapagliflozin or a pharmaceutically acceptable salt, solvate, mixed solvate, complex, or prodrug thereof. In at least one embodiment, renal failure may be defined, for example, as a ≥40% decline in eGFR or ESRD. In some embodiments, the patients with CKD may, for example, have an eGFR ranging from 15-89 ml/min/1.73 m². In other embodiments, the patients with CKD may, for example, have an eGFR ranging from 15-59 ml/min/1.73 m². In some embodiments, the patients with CKD may, for example, be at high risk of hyperkalemia (i.e., have T2D and/or have an eGFR ranging from 15-59 ml/min/1.73 m²).

In some embodiments, disclosed is an SGLT2 inhibitor for use in reducing the rate of progression of renal failure and/or renal death and/or CV death in patients with CKD, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof. In at least one embodiment, renal failure may be defined, for example, as a ≥40% decline in eGFR or ESRD. In some embodiments, the patients with CKD may, for example, have an eGFR ranging from 15-89 ml/min/1.73 m². In other embodiments, the patients with CKD may, for example, have an eGFR ranging from 15-59 ml/min/1.73 m². In some embodiments, the patients with CKD may, for example, be at high risk of hyperkalemia (i.e., have T2D and/or have an eGFR ranging from 15-59 ml/min/1.73 m²).

In some embodiments, disclosed is a method of reducing the risk of hyperkalemia in a patient with CKD comprising administering to a patient in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for reducing the risk of hyperkalemia in a patient with CKD in a patient, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for reducing the risk of hyperkalemia in a patient with CKD in a patient, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In some embodiments, disclosed is a method of treating HFrEF and CKD comprising administering to a patient in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in the treatment of HFrEF and CKD in a patient, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in the treatment of HFrEF and CKD in a patient, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In some embodiments, disclosed is a method of treating HFpEF and CKD comprising administering to a patient in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in the treatment of HFpEF and CKD in a patient, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in the treatment of HFpEF and CKD in a patient, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In some embodiments, disclosed is a method of treating HF and CKD comprising administering to a patient with an LVEF less than 55% and an eGFR ranging from about 30-60 ml/min/1.73 m2 in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in the treatment of HF and CKD in a patient with an LVEF less than 55% and an eGFR ranging from about 30-60 ml/min/1.73 m2, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in the treatment of HF and CKD in a patient with an LVEF less than 55% and an eGFR ranging from about 30-60 ml/min/1.73 m2, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In any of the above embodiments, the SGLT2 inhibitor may be, for example, dapagliflozin or a pharmaceutically acceptable salt, solvate, mixed solvate, complex, or prodrug thereof. In at least one embodiment, the SGLT2 inhibitor is dapagliflozin or a pharmaceutically acceptable salt, solvate, mixed solvate, complex, or prodrug thereof administered at 10 mg orally once per day. In any of the embodiments above, AZD9977 or a pharmaceutically acceptable salt thereof may be administered to a patient in an amount ranging from 15-150 mg orally once per day, for instance, 100 mg-150 mg orally once per day. In any of the embodiments above, AZD9977 or a pharmaceutically acceptable salt thereof may be administered to a patient in an amount ranging from 15-150 mg orally, twice per day, such as 60 mg, twice per day. In any of the embodiments above, AZD9977 or a pharmaceutically acceptable salt thereof may be administered in an amount ranging from 15-150 mg orally, once per week.

In any of the above embodiments, the patient has a left ventricular ejection fraction (LVEF) of less than or equal to 40%, such as less than or equal to 35%, 30%, or 25%, and in at least one embodiment, at least 20%. In some embodiments, the patient has an LVEF of greater than or equal to 40%, such as greater than or equal to 45%, 50%, or 55%, and in at least one embodiment, less than 55%. In some embodiments, the patient has an eGFR prior to administration of less than or equal to 60 ml/min/1.73 m2, such as less than or equal to 50 ml/min/1.73 m2, 45 ml/min/1.73 m2, 40 ml/min/1.73 m2, or 35 ml/min/1.73 m2. In some embodiments, the patient has an eGFR prior to administration of greater than or equal to 30 ml/min/1.73 m2, such as greater than or equal to 35 ml/min/1.73 m2, 40 ml/min/1.73 m2, 45 ml/min/1.73 m2, or 50 ml/min/1.73 m2. In some embodiments, the patient has T2D. In some embodiments, the patient does not have T2D. In some embodiments, hyperkalemia is understood to mean a potassium level of greater than 5.5 mmol/L. In some embodiments, hyperkalemia may be mild (serum potassium levels greater than 5.5 mmol/L) or moderate/severe (serum potassium levels greater than 6.0 mmol/L).

In some embodiments, the SGLT2 inhibitor is chosen from those disclosed in U.S. Pat. No. 6,515,177, WO/2003/099836, U.S. PG Pub. No. 2006/0194809, U.S. PG Pub. No. 2006/0063722 A1, WO/2002/083066, U.S. PG Pub. No. 2003/0064935, U.S. Pat. No. 6,774,112, U.S. PG Pub. No. 2005/0209166, U.S. PG Pub. No. 2006/0074031, U.S. PG Pub. No. 2006/0035841, U.S. PG Pub. No. 2006/0009400, U.S. PG Pub. No. 2006/0025349, U.S. PG Pub. No. 2006/0122126, U.S. PG Pub. No. 2006/0019948, U.S. PG Pub. No. 2006/0194809, U.S. Pat. Nos. 6,908,905, 6,815,428, 6,555,519, 6,683,056, EP 598359 A1, JP 035988, U.S. Pat. No. 5,731,292, EP 0850948 A1, U.S. Pat. No. 6,048,842, JP 09188625 A, JP 09124685 A, JP 09124684, EP 773226 A1, U.S. Pat. No. 5,767,094, JP 08027006 A, EP 684254 A1, JP 10245391 (Dainippon), U.S. PG Pub. No. 2005/0233982 (Boehringer Ingelheim Corp.), U.S. PG Pub. No. 2005/0119192 (Kissei Pharmaceutical Co.), WO/2006/035796 (Kissei Pharmaceutical Co.), JP 2006/117651 (Taisho Pharmaceutical Co.), JP 2004/4359630 (Yamanouchi Pharmaceutical Co.), WO/2006/080421 (Chugai Seiyaku Kabushiki Kaishi), U.S. PG Pub. No. 2005/0233988 (Tanabe Seiyaku Co.), WO/2005/012321 (Tanabe Seiyaku Co.), U.S. Pat. No. 7,015,201 (Ajinomoto Co.), WO 2006/058597 (Merck Patent GmbH), WO 2006/011469 (Chugai Seiyaku Kabushiki Kaisha), U.S. PG Pub. No. 2003/0195235 (Johnson & Johnson), and WO 2006/037537 (Boehringer Ingelheim).

In some embodiments, the SGLT2 inhibitor is chosen from those disclosed in Tsujihara, K. et al., Chem. Pharm. Bull., 44:1174-1180 (1996); Hongu, M. et al., Chem. Pharm. Bull., 46:22-33 (1998); Hongu, M. et al., Chem. Pharm. Bull., 46:1545-1555 (1998); and Oku, A. et al., Diabetes, 48:1794-1800 (1999).

In some embodiments, the SGLT2 inhibitor may be dapagliflozin (FARXIGA®), canagliflozin (INVOKANA®), empagliflozin (JARDIANCE®), ertugliflozin (STEGLATRO®), sotagliflozin, ipragliflozin, tofogliflozin, or luseogliflozin, or a pharmaceutically acceptable salt, solvate, mixed solvate, complex, or prodrug of any of the foregoing.

In some embodiments, the SGLT2 inhibitor is dapagliflozin, or a pharmaceutically acceptable salt, solvate, mixed solvate, complex, or prodrug thereof, such as described in U.S. Pat. Nos. 6,414,126 and 6,515,117, which are incorporated by reference in their entireties.

Dapagliflozin (Forxiga™/Farxiga™) is a highly selective and reversible inhibitor of SGLT2. Dapagliflozin's mechanism of action results in a direct and insulin independent elimination of glucose by the kidneys, resulting in reduced blood glucose levels in type 2 diabetes (T2D) patients. In addition, dapagliflozin has a mild diuretic and natriuretic effect. The persistent loss of glucose with associated calories in the urine, results in a consistent and maintained reduction of total body weight, predominantly a result of a reduction in fat mass including both visceral and subcutaneous adipose tissue. Moreover, dapagliflozin has also been shown to reduce BP and albuminuria, two prognostic risk factors for progression of CKD.

The chemical structure of dapagliflozin is:

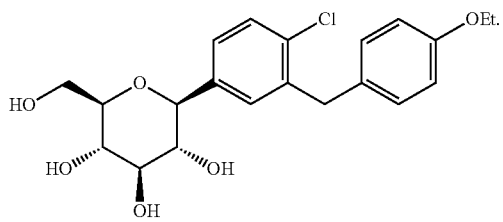

In some embodiments, dapagliflozin is in the form of a non-crystalline solid. In some embodiments, dapagliflozin is in the form of a crystalline solid. In some embodiments, dapagliflozin is in the form of a (S)-propylene glycol ((S)-PG) solvate, which has the structure:

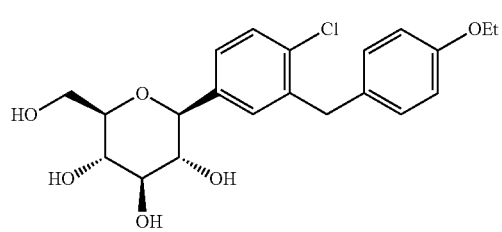 [SMILES: CCOc1ccc(Cc2cc([C@@H]3O[C@H](CO)[C@@H](O)[C@H](O)[C@H]3O)ccc2Cl)cc1]

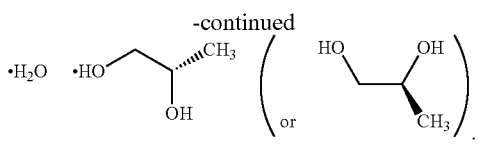

Methods for preparing a (S)-PG solvate of dapagliflozin, including a crystalline S-PG solvate, are provided in U.S. Pat. No. 7,919,598.

In some embodiments, the SGLT2 inhibitor, e.g., dapagliflozin, is administered with standard of care therapy. In some embodiments, the standard of care therapy comprises treatments to control co-morbidities and/or treatments for reducing the composite of CV death and heart failure events. In some embodiments, the standard of care therapy comprises one or more medications or medication classes, other than SGLT2 inhibitors, that are used to treat CKD.

The standard of care CKD agents, as described herein, may be used prior to and/or during administration of the SGLT2 inhibitor. In some embodiments, the standard of care CKD agents and the SGLT2 inhibitor are administered together, at the same or at different times.

Exemplary standard of care CKD agents include angiotensin-converting enzyme inhibitors (ACE-Is or ACE inhibitors) and angiotensin receptor blockers (ARBs). Standard of care CKD agents and their dosages are well-known to medical practitioners who examine and treat patients with CKD. Representative examples of ACE inhibitors include captopril, enalapril, and lisinopril. Representative examples of ARBs include valsartan, losartan, and irbesartan Exemplary standard of care HF agents include at least one standard of care HF agent, for example, at least two or at least three or more medications or medication classes, other than SGLT2 inhibitors, that are used to treat HF, for instance, HFrEF. The standard of care HF agents, as described herein, may be used prior to and/or during administration of the SGLT2 inhibitor, e.g., dapagliflozin. Standard of care HF medications and their dosages are well-known to cardiologists and other medical practitioners who examine and treat patients with HFrEF. Exemplary standard of care HF agents include: Angiotensin-converting enzyme (ACE) inhibitors; Angiotensin receptor blockers (ARB s); beta blockers; mineralocorticoid receptor agents like mineralocorticoid receptor antagonists (MRA), and neprilysin inhibitors.

Other agents that may also be considered "standard of care HF agents," include diuretics, and loop diuretics (e.g., furosemide, bumetanide, and torsemide), digoxin, heart pump medication, selective sinus node inhibitors, ivabradine (a sino-atrial (SA) node modulator), aldosterone antagonists, blood vessel dilators, calcium channel blockers (unless the patient has systolic heart failure), hydralazine/isosorbide dinitrate, or other HF medications within practice guidelines. See Yancy C. W. et al., "ACC/AHA/HFSA focused update of the 2013 ACCF/AHA guideline for the management of heart failure: A report of the American College of Cardiology/American Heart Association task force on clinical practice guidelines and the Heart Failure Society of America, *J Am Coll Cardiol.* 70(6):776-803 (2017).

Further disclosed herein are methods comprising administering to a patient in need thereof an effective amount of a SGLT2 inhibitor alone or in combination with at least one other therapeutic agent. In some embodiments, the other therapeutic agent is administered with the SGLT2 inhibitor in the same or in a different pharmaceutical composition, and at the same or at a different time.

In some embodiments, the other therapeutic agent is an antidiabetic agent, anti-obesity agent, anti-hyperlipidemic agent, anti-atherosclerotic agent, anti-hypertensive agent, anti-platelet agent, antithrombotic agent, mineralocorticoid antagonist, diuretic, and/or anticoagulant agent. For example, in at least one embodiment, the other therapeutic agent is an antidiabetic agent such as a biguanide and/or a DPP4 inhibitor. An exemplary biguanide is metformin or a pharmaceutically acceptable salt thereof. Exemplary DPP4 inhibitors include saxagliptin, linagliptin, sitagliptin, and pharmaceutically acceptable salts thereof.

In some embodiments, the antidiabetic agent is chosen from biguanides. In some embodiments, the biguanide is metformin or pharmaceutically acceptable salts thereof. In some embodiments, the biguanide is metformin HCl. In some embodiments, the biguanide is phenformin.

In some embodiments, the antidiabetic agent is chosen from sulfonylureas and pharmaceutically acceptable salts thereof. In some embodiments, the sulfonylurea is chosen from glyburide, glimepiride, glipizide, gliclazide, and chlorpropamide. In some embodiments, the sulfonylurea is glyburide. In some embodiments, the sulfonylurea is glipizide.

In some embodiments, the antidiabetic agent is chosen from glucosidase inhibitors and pharmaceutically acceptable salts thereof. In some embodiments, the glucosidase inhibitor is chosen from acarbose and miglitol.

In some embodiments, the antidiabetic agent is chosen from PPAR γ agonists. In some embodiments, the PPAR γ agonist is chosen from thiazolidinediones. In some embodiments, the thiazolidinedione is chosen from troglitazone (e.g., Warner-Lambert's REZULIN®, disclosed in U.S. Pat. No. 4,572,912), rosiglitazone (e.g., as manufactured by SKB), pioglitazone (e.g., as manufactured by Takeda), Mitsubishi's MCC-555 (disclosed in U.S. Pat. No. 5,594,016), Glaxo-Wellcome's GL-262570, englitazone (e.g., CP-68722 manufactured by Pfizer), darglitazone (e.g., CP-86325 manufactured by Pfizer), isaglitazone (e.g., as manufactured by MIT/J&J), JTT-501 (JPNT/P&U), L-895645 (Merck), R-119702 (Sankyo/WL), N,N-2344 (Dr. Reddy/NN), or YM-440 (Yamanouchi).

In some embodiments, the thiazolidinedione is chosen from pioglitazone and rosiglitazone. In some embodiments, the thiazolidinedione is pioglitazone. In some embodiments, the thiazolidinedione is rosiglitazone.

In some embodiments, the antidiabetic agent is chosen from PPAR α/γ dual agonists and pharmaceutically acceptable salts thereof. In some embodiments, the PPAR α/γ dual agonist is chosen from AR-HO39242 (Astra/Zeneca), GW-409544 (Glaxo-Wellcome), KRP297 (Kyorin Merck), those disclosed by Murakami et al., "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes, 47:1841-1847 (1998), and those disclosed in U.S. Pat. No. 6,414,002.

In some embodiments, the antidiabetic agent is chosen from aP2 inhibitors and pharmaceutically acceptable salts thereof. In some embodiments, the aP2 inhibitor is chosen from those disclosed in U.S. Pat. No. 6,548,529.

In some embodiments, the antidiabetic agent is chosen from DPP4 inhibitors and pharmaceutically acceptable salts thereof. In some embodiments, the DPP4 inhibitor is chosen from those disclosed in U.S. Pat. No. 6,395,767, WO 99/38501, WO 99/46272, WO 99/67279 (PROBIODRUG), WO 99/67278 (PROBIODRUG), WO 99/61431 (PROBIODRUG), NVP-DPP728A (1-[[[2-[(5-cyanopyridin-2-yl)

amino]ethyl]amino]acetyl]-2-cyano-(S)-pyrrolidine) (Novartis), those disclosed by Hughes et al., Biochemistry, 38 (36):11597-11603 (1999), TSL-225 (tryptophyl-1,2,3,4-tetrahydroisoquinoline-3-carboxylic acid (disclosed by Yamada et al., Bioorg. & Med. Chem. Lett., 8:1537-1540 (1998)), 2-cyanopyrrolidides, and 4-cyanopyrrolidides (as disclosed by Ashworth et al, Bioorg. & Med. Chem. Lett., 6 (22):1163-1166 and 2745-2748 (1996)).

In some embodiments, the DPP4 inhibitor is chosen from saxagliptin, vildagliptin, linagliptin, alogliptin, and sitagliptin. In some embodiments, the DPP4 inhibitor is chosen from saxagliptin and pharmaceutically acceptable salts thereof. In some embodiments, the DPP4 inhibitor is saxagliptin. In some embodiments, the DPP4 inhibitor is saxagliptin HCl.

In some embodiments, the antidiabetic agent is chosen from meglitinides and pharmaceutically acceptable salts thereof. In some embodiments, the meglitinide is chosen from repaglinide, nateglinide (Novartis), and KAD1229 (PF/Kissei). In some embodiments, the meglitinide is repaglinide.

In some embodiments, the antidiabetic agent is chosen from glucokinase activators, DGAT-1 inhibitors, and pharmaceutically acceptable salts thereof. In some embodiments, the glucokinase activator is chosen from those disclosed in WO 2008/005964. In some embodiments, the DGAT-1 inhibitor is chosen from those disclosed in U.S. PG Pub No. 2008/0090876A1.

In some embodiments, the antidiabetic agent is chosen from insulin, GLP-1 receptor agonists, and pharmaceutically acceptable salts thereof. In some embodiments, the antidiabetic agent is insulin.

In some embodiments, the at least one other therapeutic agent is chosen from anti-obesity agents and pharmaceutically acceptable salts thereof. In some embodiments, the anti-obesity agent is chosen from beta 3 adrenergic agonists, lipase inhibitors, serotonin (and dopamine) reuptake inhibitors, thyroid receptor beta modulator, MCH-1 receptor antagonists, agonists of the 5-HT2c receptor, anorectic agents, Neuropeptide Y (NPY) antagonists, Leptin analogs, MC4 receptor agonists, and antagonists of the cannabinoid receptor.

In some embodiments, the beta 3 adrenergic agonist is chosen from AJ9677 (Takeda/Dainippon), SB-418790, L750355 (Merck), CP331648 (Pfizer), and other known beta 3 agonists as disclosed in U.S. Pat. Nos. 5,541,204, 5,770,615, 5,491,134, 5,776,983 and 5,488,064. In some embodiments, the beta 3 adrenergic agonist is chosen from AJ9677, L750355, and CP331648.

In some embodiments, the at least one other therapeutic agent is chosen from anti-hyperlipidemic agents and pharmaceutically acceptable salts thereof. In some embodiments, the hyperlipidemic agent is chosen from HMG CoA reductase inhibitors. In some embodiments, the HMG-CoA reductase inhibitor is chosen from mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171, and rosuvastatin and related statin compounds disclosed in U.S. Pat. No. 5,753,675.

In some embodiments, the at least one other therapeutic agent is chosen from anti-hypertensive agents and pharmaceutically acceptable salts thereof. In some embodiments, the anti-hypertensive agent is chosen from beta adrenergic blockers, calcium channel blockers (L-type and/or T-type, diuretics, renin inhibitors, ACE inhibitors, AT-1 receptor antagonists, ET receptor antagonists such as disclosed in U.S. Pat. Nos. 5,612,359 and 6,043,265, Dual ET/AII antagonist such as disclosed in WO 00/01389, neutral endopeptidase (NEP) inhibitors, vasopepsidase inhibitors, and nitrates.

In some embodiments, the anti-hypertensive agent is chosen from bisoprolol, carvedilol, metaprolol succinate, diltiazem, verapamil, nifedipine, amlodipine, mibefradil, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone, torsemide, indapamide, metolazone, triamterene, eplerenone, captopril, zofenopril, fosinopril, enalapril, ceranopril, cilazopril, delapril, pentopril, quinapril, ramipril, lisinopril, perindopril, trandolapril, losartan, irbesartan, valsartan, candesartan, sitaxsentan, atrsentan, omapatrilat, gemopatrilat, hydralazine, isosorbide dinitrate, nitroglycerin, and nitroprusside.

In some embodiments, the at least one other therapeutic agent is chosen from anti-platelet agents and pharmaceutically acceptable salts thereof. In some embodiments, the anti-platelet agent is chosen from clopidogrel, ticlopidine, prasugrel, and aspirin.

In some embodiments, the at least one other therapeutic agent is chosen from antithrombotic agents, anticoagulant agents, and pharmaceutically acceptable salts thereof. In some embodiments, the antithrombotic agent and/or anticoagulant agent is chosen from thrombin inhibitors, platelet aggregation inhibitors, PAI-1 inhibitors, inhibitors of α-2-antiplasmin, thromboxane receptor antagonists, prostacyclin mimetics, and phosphodiesterase (PDE) inhibitors.

In some embodiments, the antithrombotic agent and/or anticoagulant agent is chosen from clopidogrel, ticlopidine, prasugrel (Eli Lilly), XR-330, T-686, anti-α-2-antiplasmin antibody, ifetroban, dipyridamole, cilostazol, aspirin, ifetroban, picotamide, and ketanserin.

In some embodiments, the SGLT2 inhibitor, e.g., dapagliflozin, is administered with at least one other therapeutic agent in the same or in a different composition, at the same or at a different time. In some embodiments, the at least one other therapeutic agent is administered before, after, or concurrently with the SGLT2 inhibitor, e.g., dapagliflozin.

In some embodiments, dapagliflozin is formulated as a fixed-dose combination pharmaceutical composition with another therapeutic agent, such as, e.g., another anti-diabetes drug. Dapagliflozin/metformin extended release (XIGDUO®)) and dapagliflozin/saxagliptin (QTERN®) and dapagliflozin/saxagliptin/metformin (QTERNMET®) are examples of combination pharmaceutical compositions comprising dapagliflozin.

In some embodiments, the weight ratio for the combination of the at least one compound chosen from SGLT2 inhibitors, e.g., dapagliflozin, and prodrugs thereof and the at least one other therapeutic agent is within the range of from about 0.01:1 to about 300:1. In some embodiments, the weight ratio for the combination of the at least one compound chosen from SGLT2 inhibitors, e.g., dapagliflozin, and prodrugs thereof and the at least one other therapeutic agent is within the range of from about 0.1:1 to about 200:1. In some embodiments, the weight ratio for the combination of the at least one compound chosen from SGLT2 inhibitors, e.g., dapagliflozin, and prodrugs thereof and the at least one other therapeutic agent is within the range of from about 0.2:1 to about 100:1.

In some embodiments, the patients being treated satisfy at least one of the following conditions:
(a) the patient does not have autosomal dominant or autosomal recessive polycystic kidney disease, lupus nephritis, or ANCA-associated vasculitis;
(b) the patient has not received cytotoxic therapy, immunosuppressive therapy, or other immunotherapy for primary or secondary renal disease within 6 months prior to treatment with the SGLT2 inhibitor;
(c) the patient does not have a history of organ transplantation;
(d) the patient does not have an intolerance to SGLT2 inhibitors;
(e) the patient does not have type 1 diabetes mellitus (T1D);
(f) the patient does not have New York Heart Association (NYHA) class IV Congestive Heart Failure at the time of treatment;
(g) the patient has not had myocardial infarction (MI), unstable angina, stroke, or transient ischemic attack (TIA) within 12 weeks prior to treatment with the SGLT2 inhibitor;
(h) the patient has not had coronary revascularization (percutaneous coronary intervention [PCI] or coronary artery bypass grafting [CABG]) or valvular repair/replacement within 12 weeks prior to treatment and is not planned to undergo any of these procedures;
(i) the patient does not have any condition outside the renal and CV disease area, with a limited life expectancy of less than 2 years;
(j) the patient does not have an active malignancy requiring treatment at the time of treatment;
(k) the patient does not have hepatic impairment (aspartate transaminase [AST]>3× the upper limit of normal [ULN], alanine transaminase [ALT]>3× the upper limit of normal [ULN], or total bilirubin >2×ULN) at time of treatment;
(l) the patient does not have a known blood-borne disease, chosen from Ebola, Lassa fever virus, Hepatitis A, B, C, D, or E viruses, and HIV type 1 or 2; and/or
(m) the patient is not a women of child-bearing potential who (1) has not been chemically or surgically sterilized or is not willing to use a medically accepted method of contraception, (2) has had a positive pregnancy test, or (3) who is breast-feeding.

In some embodiments, the patients are chosen when they satisfy one or more of the conditions (a) to (m) listed above. In some embodiments, the patients are chosen when they satisfy each of the conditions (a) to (m) listed above.

In some embodiments, the patient has HbA1c within the range of from about 6.0 to about 6.9%. In some embodiments, the patient has HbA1c within the range of from about 5.7 to about 6.5%.

The effectiveness of the compounds of the present disclosure in treating and/or preventing CKD and/or diseases, disorders, and/or conditions associated therewith can readily be determined by a person of ordinary skill in the relevant art. Determining and adjusting an appropriate dosing regimen (e.g., adjusting the amount of compound per dose and/or number of doses and frequency of dosing) can also readily be performed by a person of ordinary skill in the relevant art. One or any combination of diagnostic methods, including physical examination, assessment and monitoring of clinical symptoms, and performance of analytical tests and methods described herein, may be used for monitoring the health status of the patient.

An effective amount or therapeutically effective amount refers to an amount of at least one compound of the present disclosure or a pharmaceutical composition comprising at least one such compound of the present disclosure that, when administered to a patient, either as a single dose or as part of a series of doses, is effective to produce at least one therapeutic effect. The dose may depend upon the body mass, weight, and/or blood volume of the patient. Patients may generally be monitored for therapeutic effectiveness using assays suitable for the disease, disorder, and/or condition being treated or prevented. The level of a compound that is administered to a patient may be monitored by determining the level of the compound (or a metabolite of the compound) in a biological fluid, for example, in the blood, blood fraction (e.g., serum), and/or in the urine, and/or other biological sample from the patient. Any method practiced in the art to detect the compound, or metabolite thereof, may be used to measure the level of the compound during the course of a therapeutic regimen.

The dose of a compound described herein may depend upon the patient's condition, that is, stage of the disease, severity of symptoms caused by the disease, general health status, as well as age, gender, and weight, and other factors apparent to a person of ordinary skill in the medical art.

In some embodiments, the at least one compound chosen from SGLT2 inhibitors, e.g., dapagliflozin, and prodrugs thereof is administered at a dose equivalent of from about 1 to about 500 mg/day dapagliflozin. In some embodiments, the at least one compound chosen from SGLT2 inhibitors, e.g., dapagliflozin, and prodrugs thereof is administered at a dose equivalent of from about 2 to about 400 mg/day dapagliflozin. In some embodiments, the at least one compound chosen from SGLT2 inhibitors, e.g., dapagliflozin, and prodrugs thereof is administered at a dose equivalent of from about 0.5 to about 200 mg/day dapagliflozin. In some embodiments, the at least one compound chosen from SGLT2 inhibitors, e.g., dapagliflozin, and prodrugs thereof is administered at a dose equivalent of from about 1 to about 100 mg/day dapagliflozin. In some embodiments, the at least one compound chosen from SGLT2 inhibitors, e.g., dapagliflozin, and prodrugs thereof is administered at a dose equivalent of from about 1 to about 50 mg/day dapagliflozin. In some embodiments, the at least one compound chosen from SGLT2 inhibitors, e.g., dapagliflozin, and prodrugs thereof is administered at a dose equivalent of from about 1 to about 20 mg/day dapagliflozin. In some embodiments, the at least one compound chosen from SGLT2 inhibitors, e.g., dapagliflozin, and prodrugs thereof is administered at a dose equivalent of from about 2.5 to about 20 mg/day dapagliflozin. In some embodiments, the at least one compound chosen from SGLT2 inhibitors, e.g., dapagliflozin, and prodrugs thereof is administered at a dose equivalent of from about 2.5 to about 10 mg/day dapagliflozin. In some embodiments, the at least one compound chosen from SGLT2 inhibitors, e.g., dapagliflozin, prodrugs thereof is administered at a dose equivalent of about 10 mg/day dapagliflozin. In some embodiments, the at least one compound chosen from SGLT2 inhibitors, e.g., dapagliflozin, and prodrugs thereof is administered at a dose equivalent of about 5 mg/day dapagliflozin. In some embodiments, the at least one compound chosen from SGLT2 inhibitors, e.g., dapagliflozin, and prodrugs thereof is administered at a dose equivalent of about 2.5 mg/day dapagliflozin.

In some embodiments, the methods disclosed herein comprise administering to the patient orally an SGLT2 inhibitor, such as dapagliflozin or a pharmaceutically acceptable salt, solvate, mixed solvate, complex, or prodrug thereof, at a dose of 2.5 mg/day, 5.0 mg/day, or 10 mg/day. In at least one embodiment, the dose of dapagliflozin is 10 mg/day.

The terms "treating" or "treatment" or "to treat" refer to therapeutic measures that cure, slow down, lessen symptoms of, and/or halt progression of a diagnosed pathologic disease, disorder, or condition. Treatment need not result in a complete cure of the condition; partial inhibition or reduction of the condition being treated is encompassed by this term.

The term "about" as used herein refers to within 20%, such as within 10% and further such as within 5%, of a given value or range.

The term "or" is used herein to mean, and is used interchangeably with, the term "and/or," unless context clearly indicates otherwise.

The term "other therapeutic agent" as used herein refers to a therapeutic agent other than the SLGT2 inhibitors of the present disclosure, or prodrugs thereof.

The term "prodrug" as used herein includes, for example, esters and carbonates that may be converted, for example, under physiological conditions or by solvolysis, to dapagliflozin. Thus, the term prodrug includes metabolic precursors of dapagliflozin that are pharmaceutically acceptable. The term prodrug also includes covalently bonded carriers that release dapagliflozin in vivo when such prodrug is administered to a patient. Non-limiting examples of prodrug include esters and carbonates formed by reacting one or more hydroxyls of dapagliflozin with alkyl, alkoxy, or aryl substituted acylating agents employing procedures known to those skilled in the art to generate acetates, pivalates, methylcarbonates, benzoates, and the like. Various forms of prodrugs are known in the art. For examples of such prodrug derivatives, see: (1) Design of Prodrugs, edited by H. Bundgaard, (Elsevier, 1985) and Methods in Enzymology, Vol. 42, p. 309-396, edited by K. Widder, et al. (Academic Press, 1985); (2) A Textbook of Drug Design and Development, edited by Krogsgaard-Larsen and H. Bundgaard, Chapter 5 "Design and Application of Prodrugs", by H. Bundgaard p. 113-191 (1991); (3) H. Bundgaard, Advanced Drug Delivery Reviews, 8, 1-38 (1992); (4) H. Bundgaard, et al., Journal of Pharmaceutical Sciences, 77, 285 (1988); and (5) N. Kakeya, et al., Chem Pharm Bull, 32, 692 (1984).

The term "reaching end stage renal disease (ESRD)" as used herein refers to (i) having a sustained eGFR <15 mL/min/1.73 m$^2$, (ii) receiving chronic dialysis treatment, or (iii) receiving a renal transplant. ESRD may also be referred to as "end stage kidney disease" (ESKD) and may be used herein interchangeably.

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The examples provided do not in any way limit the disclosure.

EXAMPLES

Example 1: A Study to Evaluate the Effect of Dapagliflozin on Renal Outcomes and Cardiovascular Mortality in Patients with Chronic Kidney Disease (DAPA CKD)

Study Design

This was an international, multi-center, event-driven, randomized, double-blind, parallel group, placebo-controlled study, evaluating the effect of dapagliflozin 10 mg versus placebo, given once daily in addition to standard of care, to prevent the progression of chronic kidney disease (CKD) or cardiovascular (CV) death/renal death. The study followed the design set forth in FIG. 1.

The schedule of study visits and assessments is shown in Table 1 below.

| | | | Activity | | | | | |
|---|---|---|---|---|---|---|---|---|
| | | | | | | | Premature treatment discontinuation visit | Study closure visit |
| Enrolment | Randomisation | | Site visits | | | | | |
| | | | Visit number | | | | | |
| 1 | 2 | 3 | 4 | 5 | 6 | 7, 8, 9 etc. | PTDV | SCV |
| | | | | Day | | | | |
| −14 (±7) | 0 | 14 (±3) | 60 (±7) | 120 (±7) | 240 (±14) | 360 (±14) and every 4$^{th}$ month) | | ≤6 weeks from SED |

| | | | | | | | | |
|---|---|---|---|---|---|---|---|---|
| Sign Informed Consent Form (ICF) | X | | | | | | | |
| Inclusion/exclusion criteria | X | X | | | | | | |
| Enrolment in IxRS | X | | | | | | | |
| Randomisation in IxRS | | X | | | | | | |
| Demography | X | | | | | | | |
| Medical/surgical history | | | | | | | | |
| Vital signs (BP, pulse and body weight) | X | X | X | X | X | X | X | X | X |
| Height | X | | | | | | | |
| Local laboratory assessment $^a$ | X $^a$ | | | | | | | |
| Central laboratory assessment $^b$ | X | X | X | X | X | X | X | X | X |
| Spot UACR, central laboratory sampling | X | X | X | X | X | X | X | X | X |
| Pregnancy testing | X | X | | | | | | |

-continued

| | Activity | | | | | | | | |
|---|---|---|---|---|---|---|---|---|---|
| | Enrolment | Randomisation | Site visits | | | | | Premature treatment discontinuation visit | Study closure visit |
| | Visit number | | | | | | | | |
| | 1 | 2 | 3 | 4 | 5 | 6 | 7, 8,9 etc. | PTDV | SCV |
| | Day | | | | | | | | |
| | −14 (±7) | 0 | 14 (±3) | 60 (±7) | 120 (±7) | 240 (±14) | 360 (±14) and every 4$^{th}$ month) | | ≤6 weeks from SED |
| Sample for biomarker research, if applicable [c] | | X | | | | | X [c] | | |
| Sample for genetic research, if applicable [c] | | X | | | | | | | |
| PK sampling (pre-dose) | | | | | | | X [d] | | |
| Potential endpoints, SAEs DAEs etc, AEs of interest [e] | X [e] | X | X | X | X | X | X | X | X |
| KDQOL ™-36 questionnaire | | X | | | | | X [f] | X | X |
| EQ-5D-5L questionnaire | | X | | | X | X | X [f] | X | X |
| General physical examination | | X | | | | | | X | X |
| Targeted physical examination | | | X | X | X | X | X | | |
| Electrocardiogram (ECG) | | X | | | | | | | |
| Concomitant medication | | X | X | X | X | X | X | X | X |
| Dispense (including kit verification in IxRS)/Collect IP | | X | | X | X | X | X | X | X |
| IP compliance reminder | | X | X | X | X | X | X | | |

[a] Local laboratory assessment was optional to assess eligibility (according to local routine) of eGFR and/or albuminuria.
[b] Central laboratory assessments included alkaline phosphatase (ALP), ALT, AST, bilirubin, blood urea nitrogen (BUN), creatinine (including eGFR assessment), haematocrit, haemoglobin (Hb), HbA1c, phosphate, potassium, and sodium.
[c] Blood and urine samples for future biomarker and/or genetic research were optional. Biomarker samples were collected at visit 2 and 7, and genetic samples were collected at visit 2. PK samples were collected at visit 7.
[d] SAEs were collected from the time of informed consent throughout the study until and including the patient's last visit. Study endpoints, DAEs, AEs leading to dose reduction and temporary interruptions, and other AEs of interest were collected from randomisation throughout the study until and including the patient's last visit.
[e] The PRO questionnaires were completed as specified until visit 7 and thereafter every 12 months, and at PTDV and study closure visit (SCV).

Patient Reported Outcomes (PROs):

PROs is an umbrella term referring to all outcomes and symptoms that are directly reported by the patient. The following PROs were administered in the study: KDQOL™-36 and EQ-5D-5L (see Appendix B and Appendix C). Patients were asked to complete the EQ-5D-5L and the KDQOL™-36 at the visits as specified in Table 1.

The Kidney Disease Quality of Life-36 (KDQOL™-36):

The KDQOL™-36 is an abbreviated form of the KDQOL, which is a self-reported questionnaire that combines generic and disease-specific components for assessing the health-related quality of life of patients with CKD, (see Appendix B.)

EuroQol Five-Dimensional Five-Level Questionnaire (EQ-5D-5L):

The EQ-5D-5L is a self-reported questionnaire that is used to derive a standardized measure of health status, also referred to as a utility score. EQ-5D-5L utility scores are widely accepted by reimbursement authorities and will be used to support health economic evaluations (see Appendix C.)

Patient Population:

The study population chosen for this study included a broad population of patients with impaired kidney function. The target population had CKD (defined as eGFR ≥25 and ≤75 mL/min/1.73 m$^2$) with albuminuria (defined as urine albumin creatinine ratio [UACR]≥200 and ≤5000 mg/g) with or without type 2 diabetes (T2D). However, patients with known polycystic kidney disease, glomerulonephritis with flares (lupus or anti-neutrophil cytoplasmic antibodies (ANCA) associated vasculitis) or ongoing active renal inflammation were excluded.

Patients with T2D at randomization in this study continued their T2D treatment. Patients were eligible for adjustments in their anti-diabetes treatment at the discretion of their diabetes health care provider.

Concomitant treatment (i.e., treatment in combination with the investigational product ("IP") with open label SGLT2 inhibitors e.g., dapagliflozin, empagliflozin, canagliflozin, ertugliflozin, tofogliflozin, and luseogliflozin, and fixed dose combinations containing these drugs was prohibited.

Final patient enrollment data of the DAPA CKD Phase 3 clinical trial is depicted in FIGS. 2-5.

Patients included in the study satisfied the following criteria:
  Female or male aged ≥18 years at the time of consent.
  eGFR ≥25 and ≤75 mL/min/1.73 m$^2$ (CKD-EPI Formula) at visit 1.
  Evidence of increased albuminuria 3 months or more before visit 1 and UACR ≥200 and ≤5000 mg/g at visit 1.
  Stable, and for the patient maximum tolerated labelled daily dose, treatment with ACE-I or ARB for at least 4 weeks before visit 1, if not medically contraindicated.

Patients were excluded from the study if any of the following exclusion criteria were fulfilled:

Autosomal dominant or autosomal recessive polycystic kidney disease, lupus nephritis, or ANCA-associated vasculitis.

Received cytotoxic therapy, immunosuppressive therapy, or other immunotherapy for primary or secondary renal disease within 6 months prior to enrolment.

History of organ transplantation.

Received therapy with an SGLT2 inhibitor within 8 weeks prior to enrolment or previous intolerance of an SGLT2 inhibitor.

Type 1 diabetes mellitus (T1D).

New York Heart Association (NYHA) class IV Congestive Heart Failure at the time of enrolment (see Appendix A).

MI, unstable angina, stroke, or transient ischemic attack (TIA) within 12 weeks prior to enrolment.

Coronary revascularization (percutaneous coronary intervention [PCI] or coronary artery bypass grafting [CABG]) or valvular repair/replacement within 12 weeks prior to enrolment or had planned to undergo any of these procedures after randomization.

Any condition outside the renal and CV disease area, such as but not limited to malignancy, with a limited life expectancy of less than 2 years.

Active malignancy requiring treatment at the time of visit 1 (with the exception of successfully treated basal cell or treated squamous cell carcinoma).

Hepatic impairment (aspartate transaminase [AST]>3× the upper limit of normal [ULN], alanine transaminase [ALT]>3× the upper limit of normal [ULN], or total bilirubin >2× ULN at time of enrolment). An isolated increase in bilirubin in patients with known Gilbert's syndrome was not a reason for exclusion.

Known blood-borne diseases such as Ebola, Lassa fever virus, Hepatitis A, B, C, D, or E viruses, and/or HIV types 1 or 2.

Women of child-bearing potential (i.e., those who were not chemically or surgically sterilized or who were not post-menopausal) who were not willing to use a medically accepted method of contraception from the time of signing the informed consent throughout the study and 4 weeks thereafter, OR women who had a positive pregnancy test at enrolment or randomization OR women who were breast-feeding.

Involvement in the planning and/or conduct of the study.

Previous randomization in the present study.

Participation in another clinical study with an investigational product during the last month prior to enrolment.

Inability of the patient, in the opinion of the investigator, to understand and/or comply with investigational product, procedures, and/or follow-up OR any conditions that, in the opinion of the investigator, may have rendered the patient unable to complete the study. Patients who could not complete the patient reported outcome (PRO) assessments could still participate in the study.

Primary Outcome Measure and Rationale:

The primary outcome measure of the study was to determine if dapagliflozin is superior to placebo in reducing the incidence of the primary composite endpoint of ≥50% sustained decline in eGFR, reaching ESRD, CV death, or renal death when added to current background therapy in patients with eGFR ≥25 and ≤75 mL/min/1.73 m$^2$ and albuminuria (UACR ≥200 and ≤5000 mg/g).

Endpoints Related to eGFR Decline:

eGFR baseline was defined as the mean central laboratory value from visit 1 and visit 2.

The primary outcome measure was based on the requirements as outlined in the European Medicines Agency (EMA)'s draft guideline, which states that a composite endpoint of ≥50% sustained decline in eGFR, end stage renal disease (ESRD), and renal death (death due to ESRD when dialysis is not given) are acceptable outcome measures (EMA 2016). This endpoint has also been used in a number of previous outcome studies.

CV mortality was added as a component of the composite endpoint since CV mortality in the population being studied is high and the risk for CV death correlates with the risk of developing ESRD.

For the purpose of the efficacy analysis, deaths were sub-classified into CV and non-CV as well as renal primary cause (death due to ESRD when dialysis is not given).

Secondary Outcome Measure and Rationale:

The secondary outcome measures included (1) determining whether dapagliflozin, compared with placebo, results in a reduction of the incidence of the composite endpoints of worsening of renal function; (2) determining whether dapagliflozin, compared with placebo, results in a reduction of the incidence of the composite endpoint of CV death or hospitalization for heart failure; and (3) determining whether dapagliflozin, compared with placebo, results in a reduction of the incidence of all-cause mortality (i.e., mortality due to any/all causes).

Heart failure was assessed as a secondary endpoint because it is particularly common in patients with CKD. All-cause mortality was assessed as a secondary endpoint to evaluate the effect of dapagliflozin on non-CV (including infection (e.g., sepsis) and malignancies), as well as CV, mortality, and hence overall mortality.

A further outcome included determining whether dapagliflozin, compared with placebo, results in a reduction of the incidence of the composite endpoints of chronic dialysis, kidney transplantation, or renal death.

Duration of Treatment:

This study was event-driven and lasted 40 months. The study was stopped early (60% of planned events) due to overwhelming efficacy.

Investigational Product (IP), Dosage, and Mode of Administration:

Patients were randomized 1:1 to either dapagliflozin 10 mg or placebo. In addition to the 10 mg dose, the 5 mg dose of dapagliflozin could be used in the study when clinically indicated. However, if the dose had been decreased to 5 mg, the dose was increased back to dapagliflozin 10 mg or matching placebo as soon as, in the opinion of the investigator, the patient's condition was stable.

Statistical Methods:

The primary objective of the study was to determine the superiority of dapagliflozin versus placebo in reducing the incidence of the primary composite endpoint (i.e., as compared to patients receiving at least one standard of care CKD agent alone).

All patients who had been randomized to study treatment were included in the full analysis set (FAS) irrespective of their protocol adherence and continued participation in the study. The primary variable was the time to first event included in the primary composite endpoint. The primary analysis was based on the intention to treat (ITT) principle using the FAS. In the analysis of the primary composite endpoint, dapagliflozin versus placebo was compared using a Cox proportional hazards model with a factor for treatment group, stratified by randomization stratification factors (T2D, UACR), and adjusting for eGFR.

An interim analysis was performed when 75% of the pre-determined number of primary endpoints were confirmed, using a Haybittle-Peto rule. The interim analysis assessed superiority of dapagliflozin to placebo.

Figure 8:
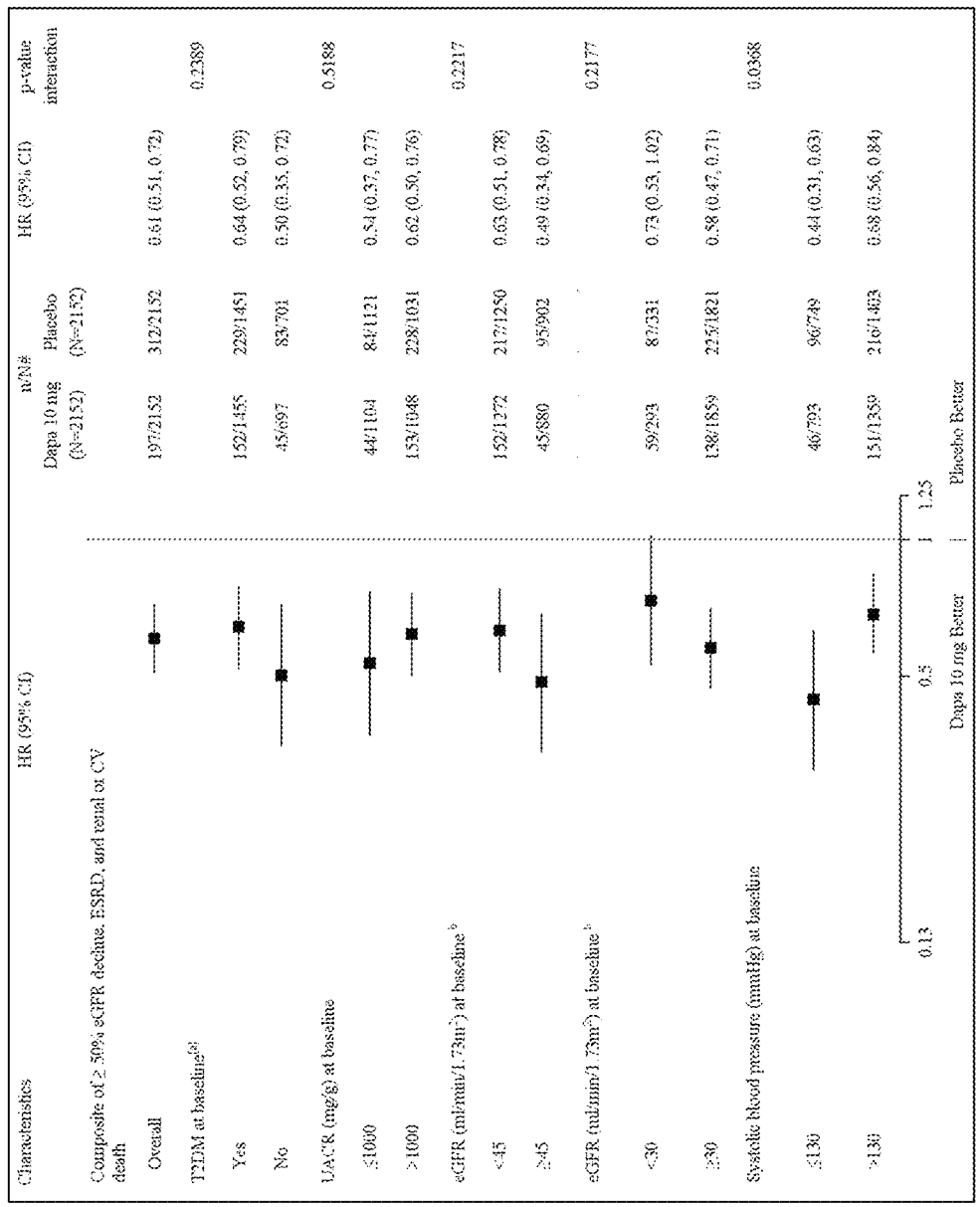
FIG. 8 depicts the primary composite outcome according to prespecified subgroups, from the DAPA CKD phase 3 clinical trial (T2DM status, UACR status, eGFR status, systolic blood pressure status).
Figure 9:
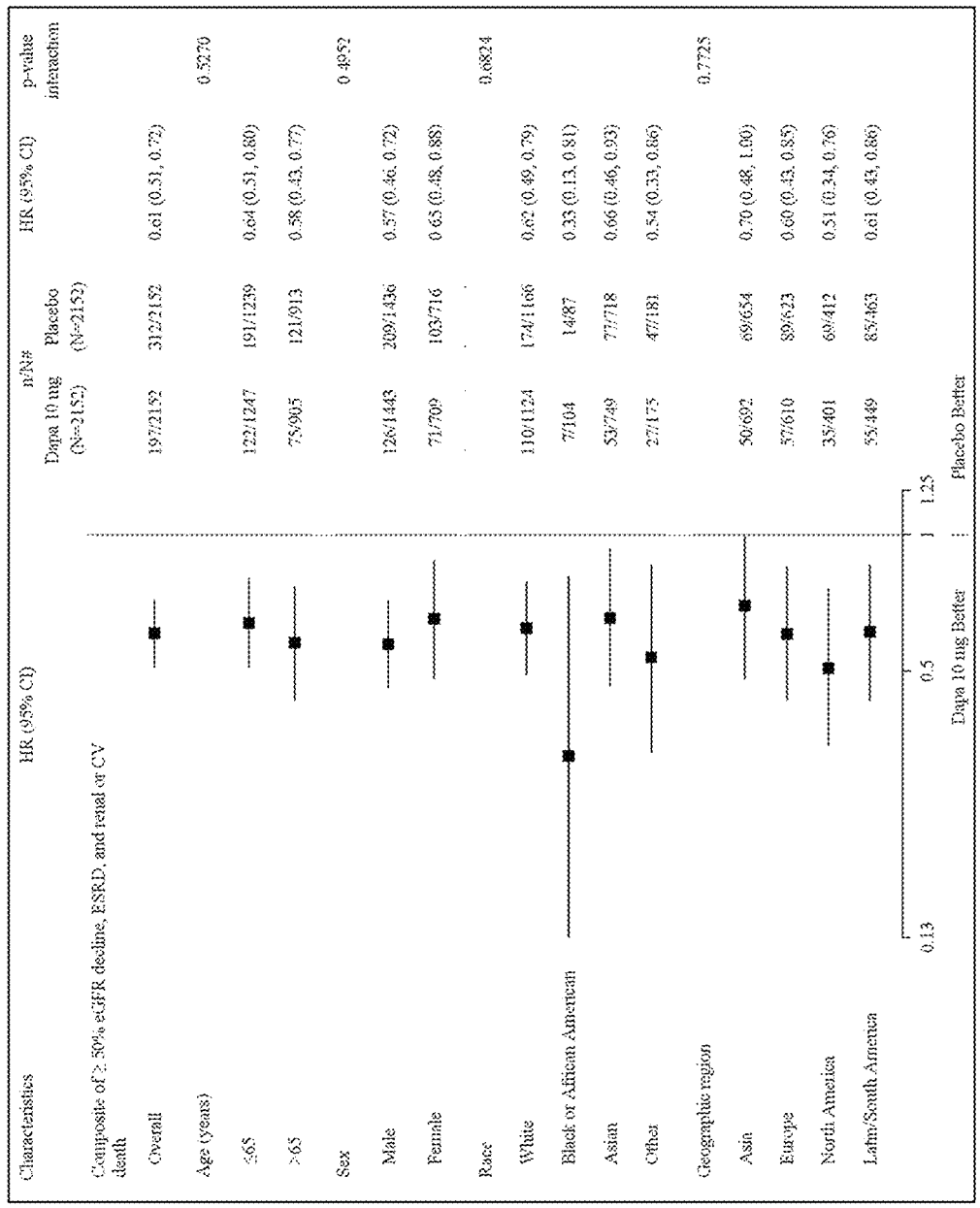
FIG. 9 depicts the primary composite outcome according to prespecified subgroups, from the DAPA CKD phase 3 clinical trial (age, sex, race, geographic region).

A closed testing procedure including a pre-specified hierarchical ordering of the primary and secondary endpoints was utilized. No multiplicity control was placed on the exploratory endpoints Safety Assessments Definitions of serious adverse event (SAE): An SAE was defined as an AE occurring during any study phase (i.e., run-in, treatment, washout, and follow-up), that fulfils one or more of the following criteria:
- Results in death
- Is immediately life-threatening
- Requires in-patient hospitalization or prolongation of existing hospitalization
- Results in persistent or significant disability/incapacity or substantial disruption of the ability to conduct normal life functions
- Is a congenital abnormality or birth defect
- Is an important medical event that may jeopardize the patient or may require medical intervention to prevent one of the outcomes listed above Study Outcomes Final results for the primary endpoint measure are shown in FIGS. 6-10 and FIG. 13. The primary objective was met, treatment with dapagliflozin resulted in a clinically meaningful and statistically significant reduction of the composite ≥50% sustained eGFR decline, ESRD, and renal or CV death. All components contributed to the observed treatment effect. Treatment benefit consistent across all patient subgroups including: Diabetes status, UACR, and eGFR (FIG. 8). Treatment benefit consistent across all patient subgroups including: age, sex, race, and geographic region (FIG. 9).

Figure 12:
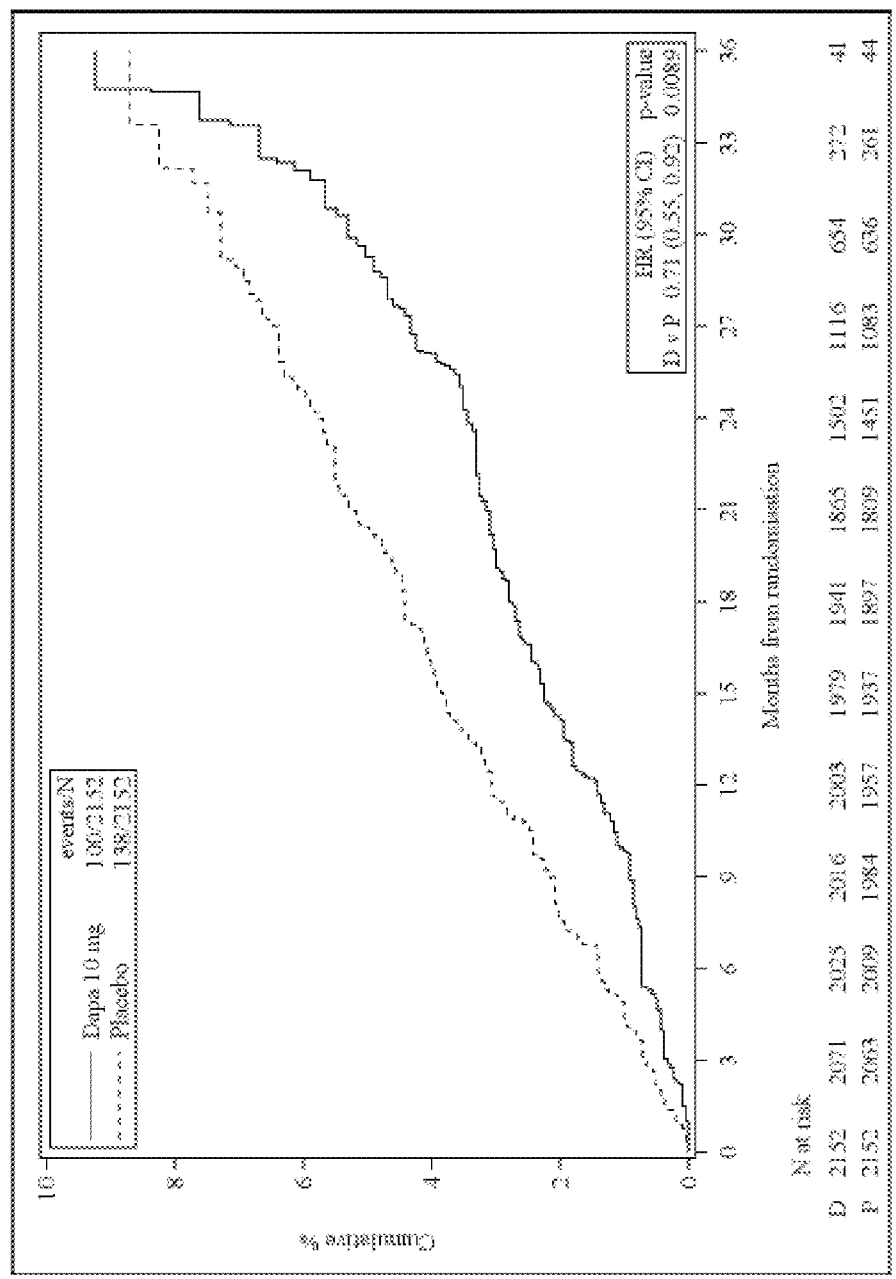
FIG. 12 is a graph depicting the incidence of the secondary endpoint of the early treatment effect of dapagliflozin on hospitalisation for HF and CV death estimated with the use of the Kaplan-Meier method and hazard ratios and 95% confidence intervals were estimated with the use of Cox regression models.
Figure 14:
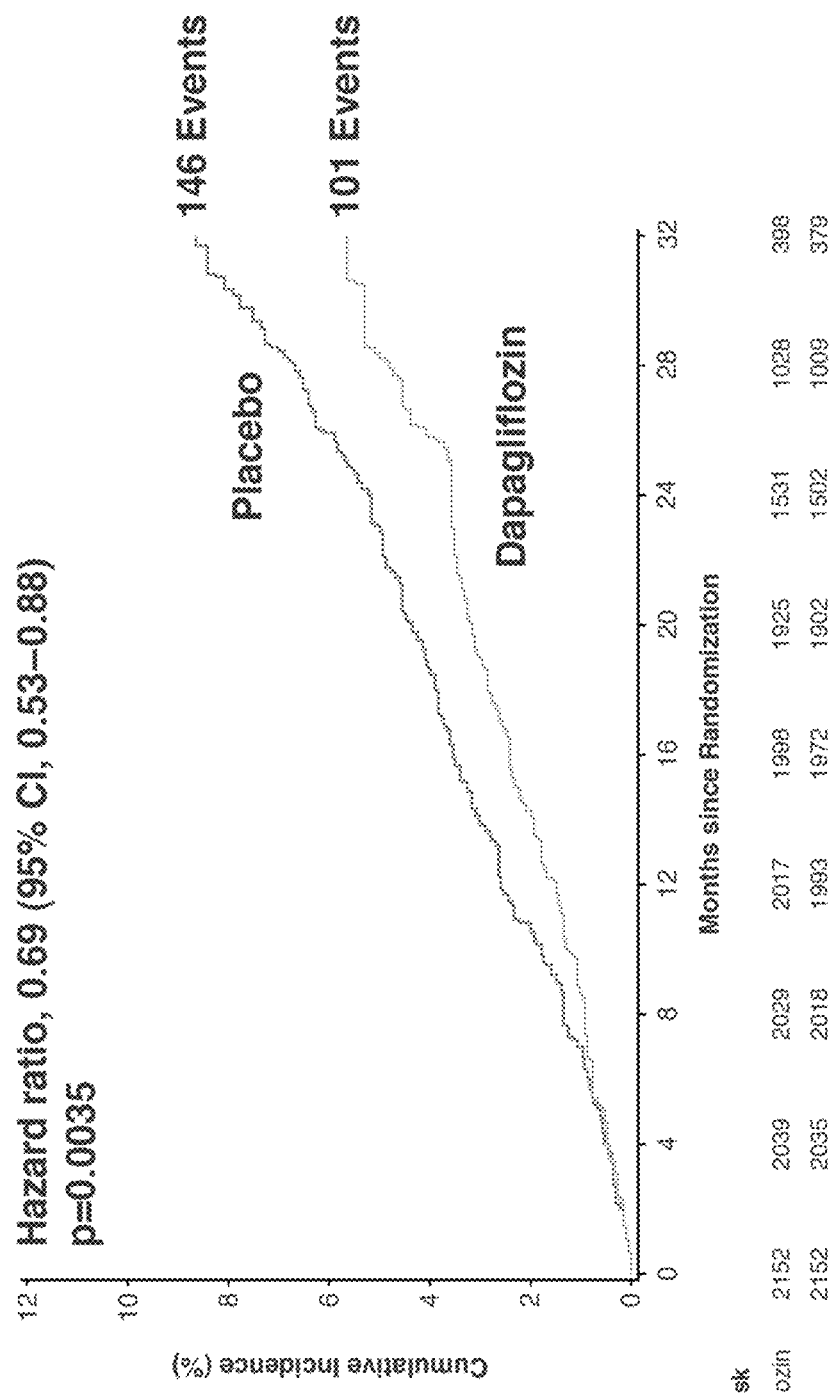
FIG. 14 is a graph depicting the effect of dapagliflozin on all-cause mortality estimated with the use of the Kaplan-Meier method and hazard ratios and 95% confidence intervals were estimated with the use of Cox regression models.

Final results for the secondary endpoints are shown in FIGS. 10-13. The significant treatment effect on the renal-only secondary endpoint (composite of ≥50% sustained decline in eGFR, ESRD & renal death) confirms positive renal treatment effect (FIG. 10). Statistically significant reduction of the secondary endpoint of composite of CV death and hospitalisation for HF is shown in FIGS. 11-12. Both components contributed to the treatment effect. Dapagliflozin was superior to placebo in reducing death from any cause (FIGS. 13-14).

A ≥50% sustained decline in eGFR, ESRD, and CV or renal death (the primary end point) occurred in 197 patients (9.2%) in the dapagliflozin group and 312 patients (14.5%) in the placebo group (hazard ratio, 0.61; 95% confidence interval [CI], 0.51 to 0.72; P<0.0001 (FIG. 6). Other specific data points for each of the primary and secondary endpoints are illustrated in FIGS. 6-13.

Figure 15:
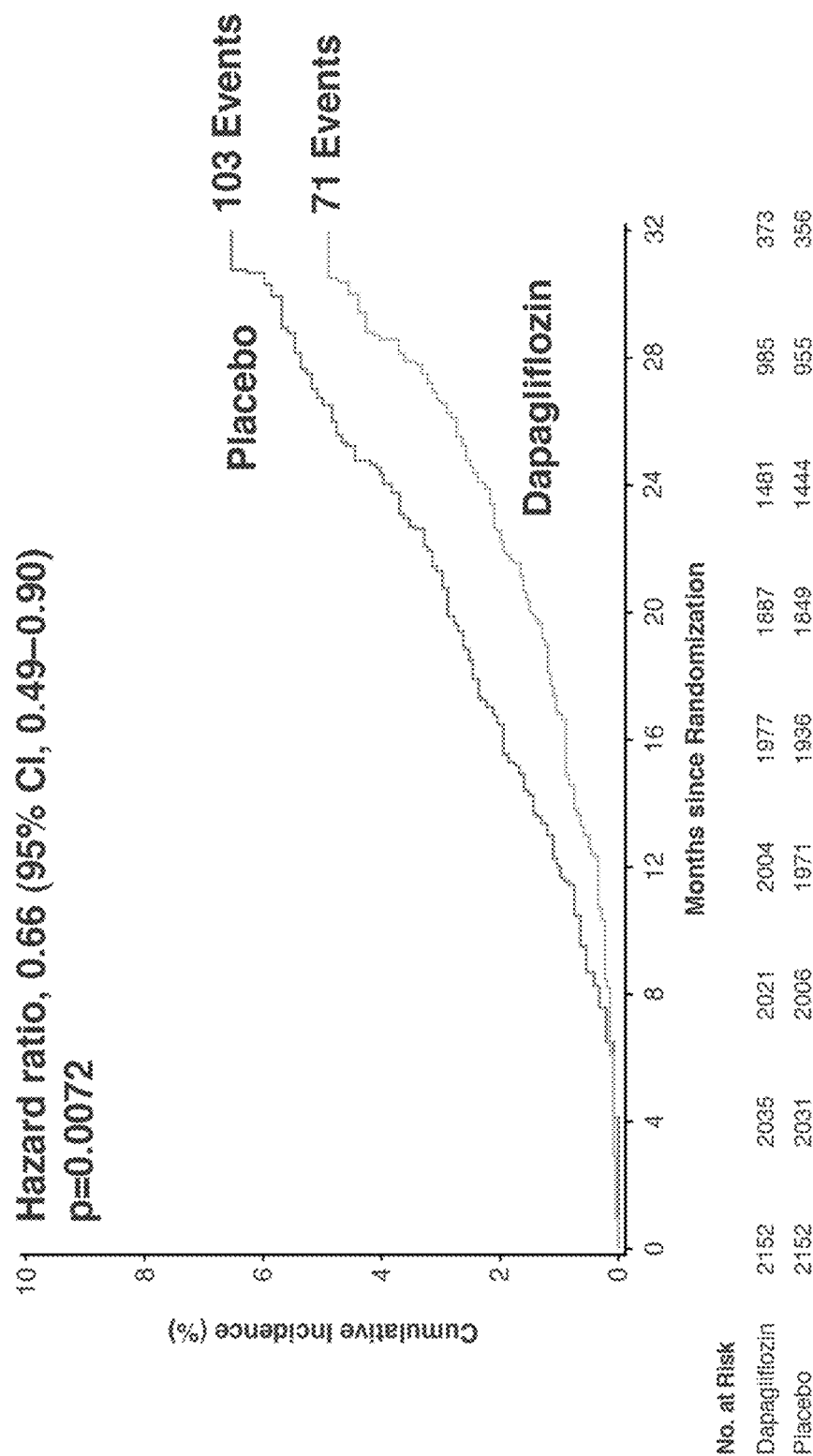
FIG. 15 is a graph depicting the effect of dapagliflozin on the endpoint of dapagliflozin on chronic dialysis, kidney transplantation or renal death estimated with the use of the Kaplan-Meier method and hazard ratios and 95% confidence intervals were estimated with the use of Cox regression models.
Figure 17:
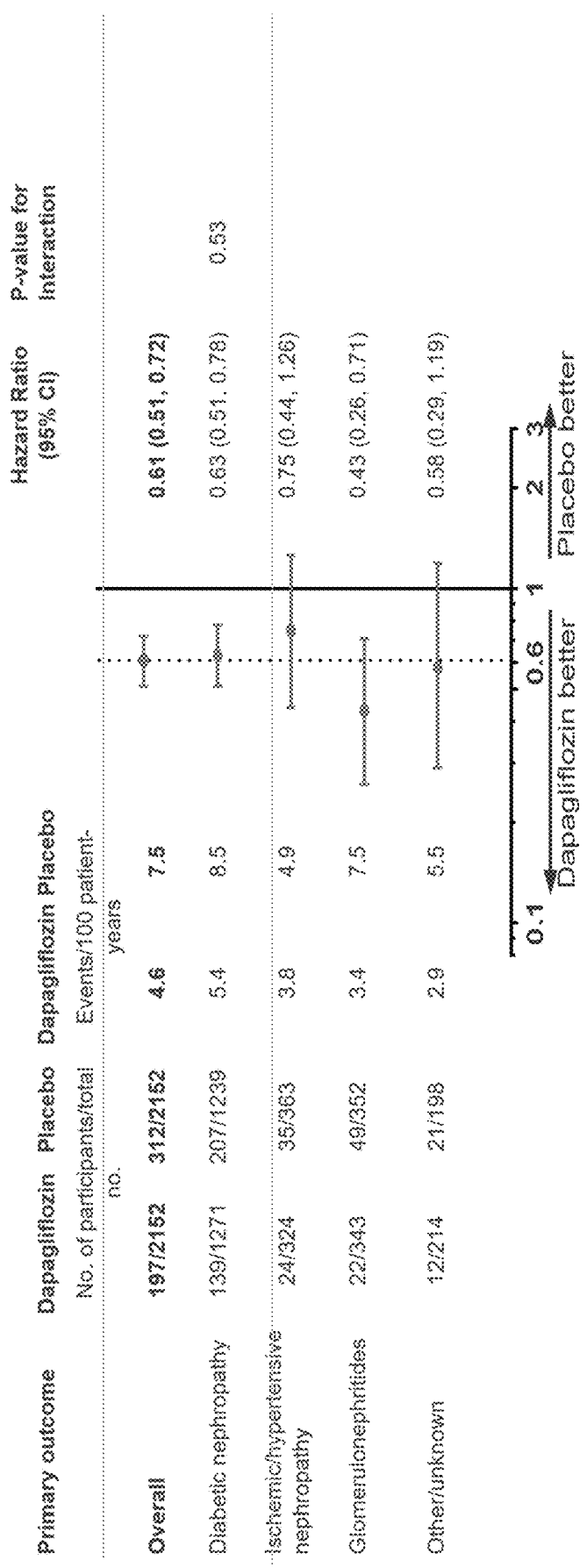
FIG. 17 summarizes the DAPA CKD phase 3 clinical trial primary endpoint (composite of sustained ≥50% eGFR decline, ESKD, or renal or cardiovascular death) stratified by underlying cause of kidney disease (diabetic nephropathy, ischemic/hypertensive nephropathy, glomerulonephritis, and unknown etiology) (as compared to placebo group or patients receiving at least one standard of care CKD agent alone)
Figure 18:
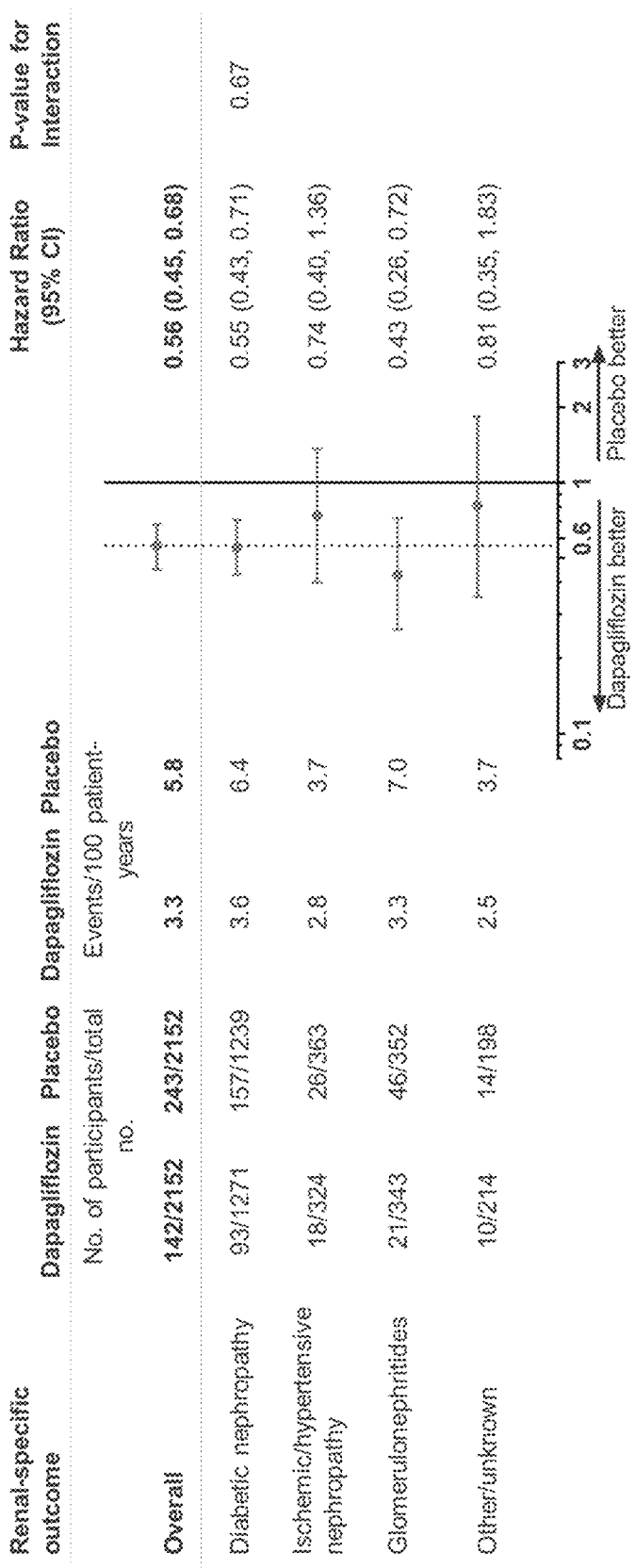
FIG. 18 summarizes the DAPA CKD phase 3 clinical trial secondary renal endpoint (composite of sustained ≥50% eGFR decline, ESKD, or renal death) stratified by underlying cause of kidney disease (diabetic nephropathy, ischemic/hypertensive nephropathy, glomerulonephritis, and unknown etiology) (as compared to placebo group or patients receiving at least one standard of care CKD agent alone)
Figure 19:
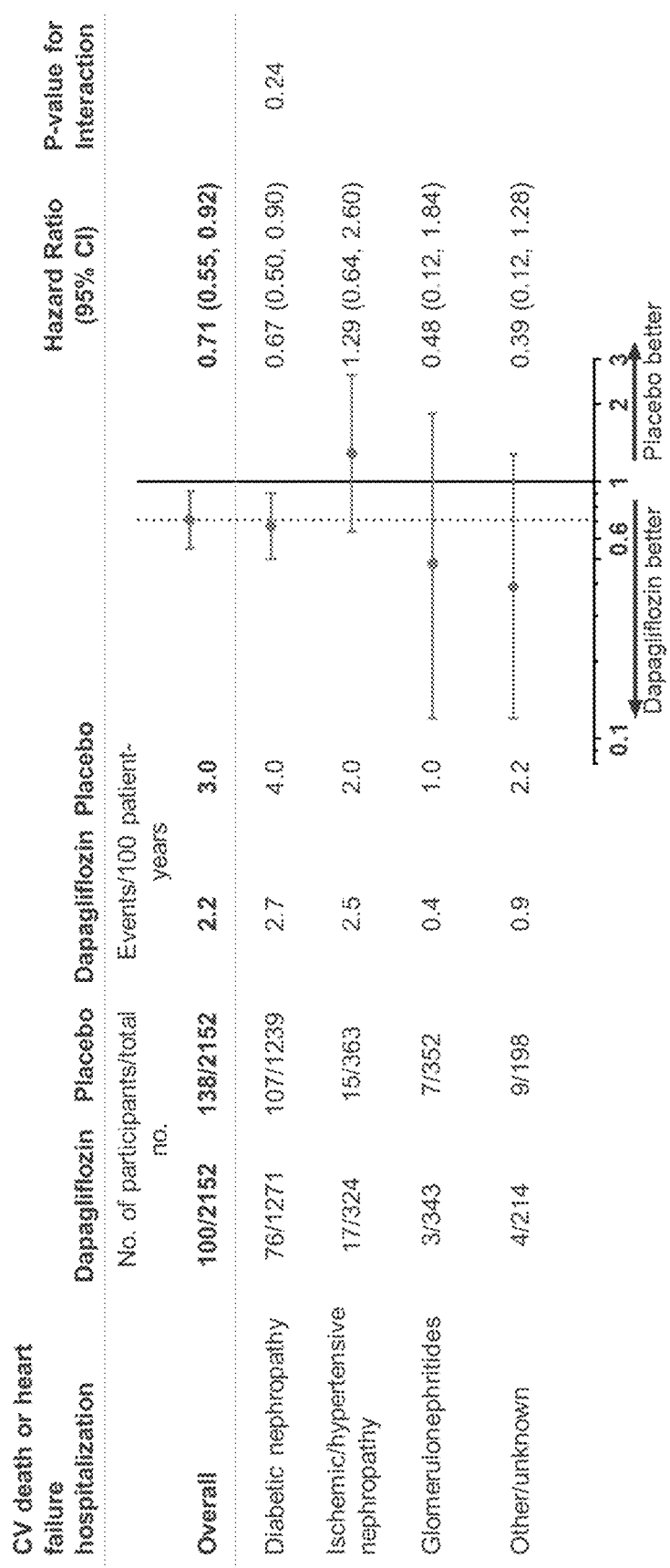
FIG. 19 summarizes the DAPA CKD phase 3 clinical trial secondary endpoint (cardiovascular death or hospitalization for heart failure) stratified by underlying cause of kidney disease (diabetic nephropathy, ischemic/hypertensive nephropathy, glomerulonephritis, and unknown etiology) (as compared to placebo group or patients receiving at least one standard of care CKD agent alone)
Figure 20:
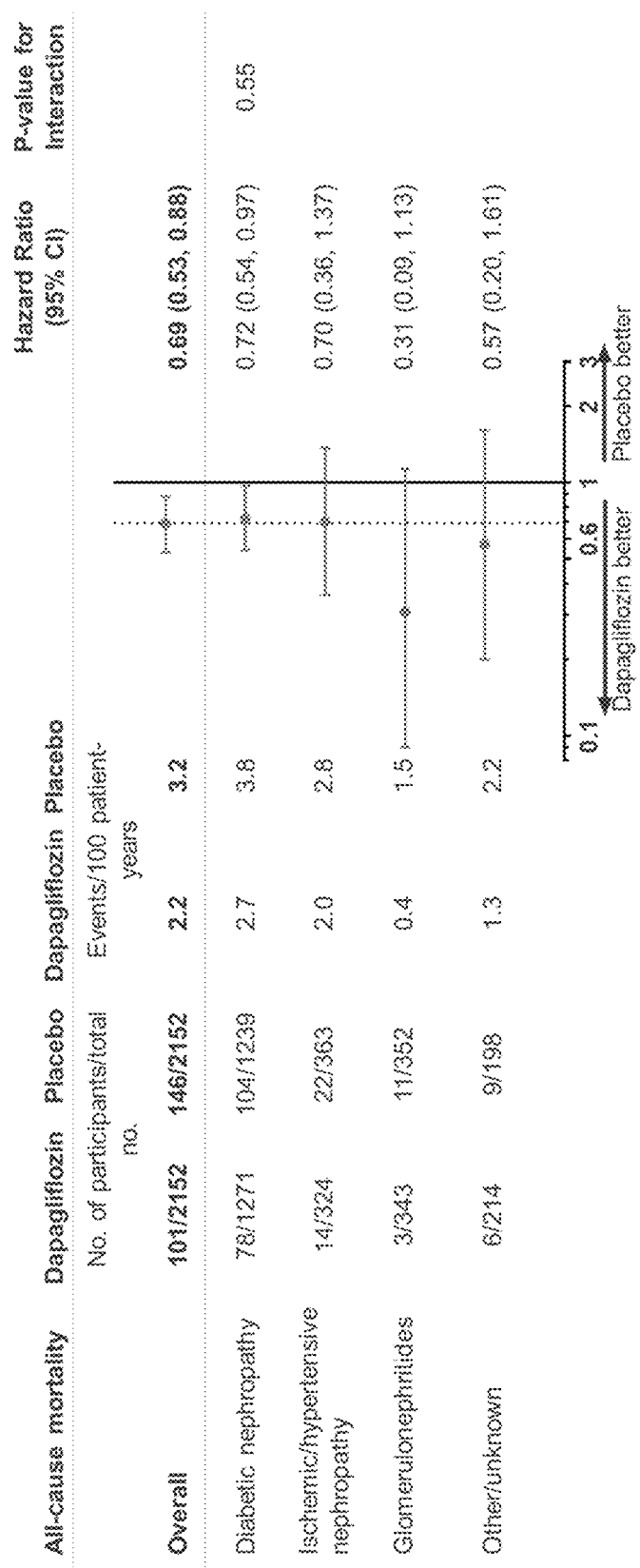
FIG. 20 summarizes the DAPA CKD phase 3 clinical trial secondary endpoint (all cause mortality) stratified by underlying cause of kidney disease (diabetic nephropathy, ischemic/hypertensive nephropathy, glomerulonephritis, and unknown etiology) (as compared to placebo group or patients receiving at least one standard of care CKD agent alone)

Statistically significant reduction of the endpoint of composite of chronic dialysis, kidney transplantation or renal death is shown in FIG. 15.

Figure 21:
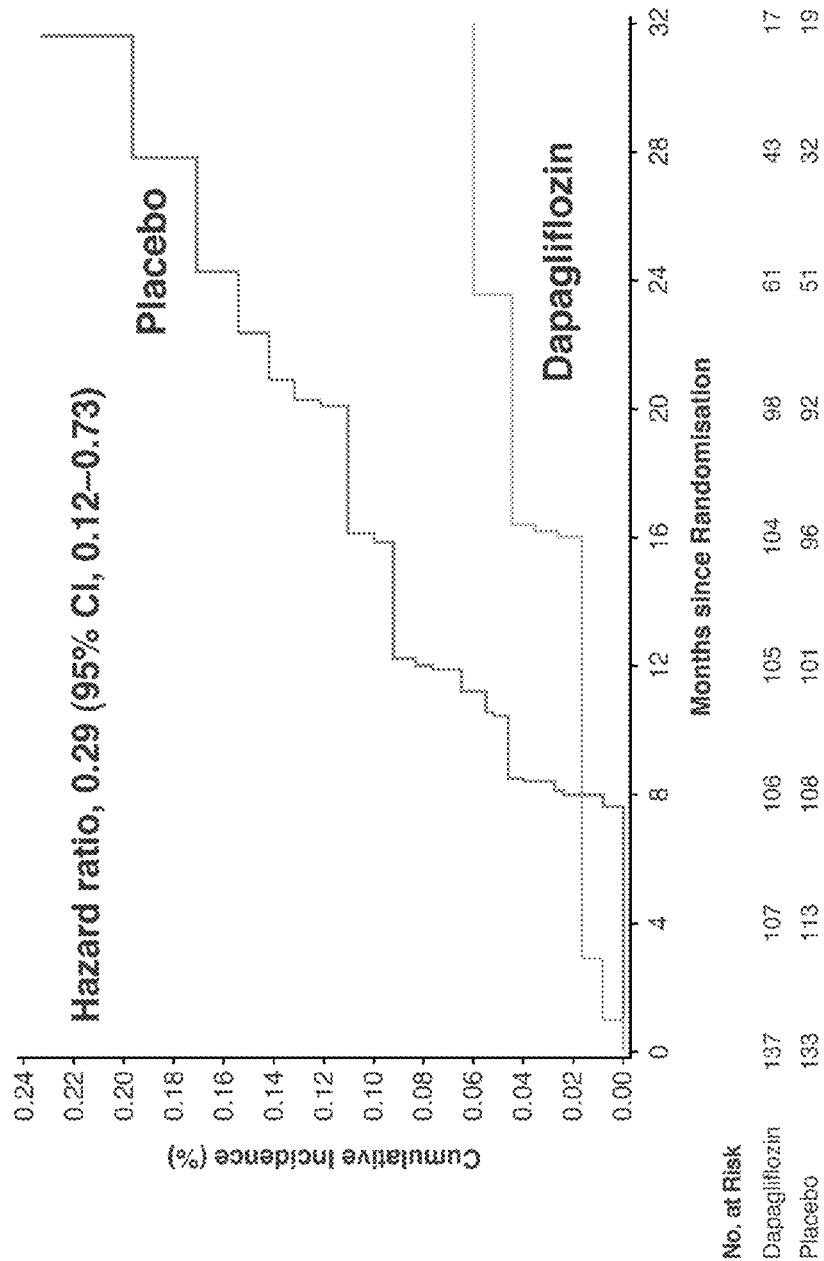
FIG. 21 summarizes the DAPA CKD phase 3 clinical trial primary endpoint (composite of sustained ≥50% eGFR decline, ESKD, or renal or cardiovascular death) in patients with IgA nephropathy as compared to placebo group or patients receiving at least one standard of care CKD agent alone.
Figure 22:
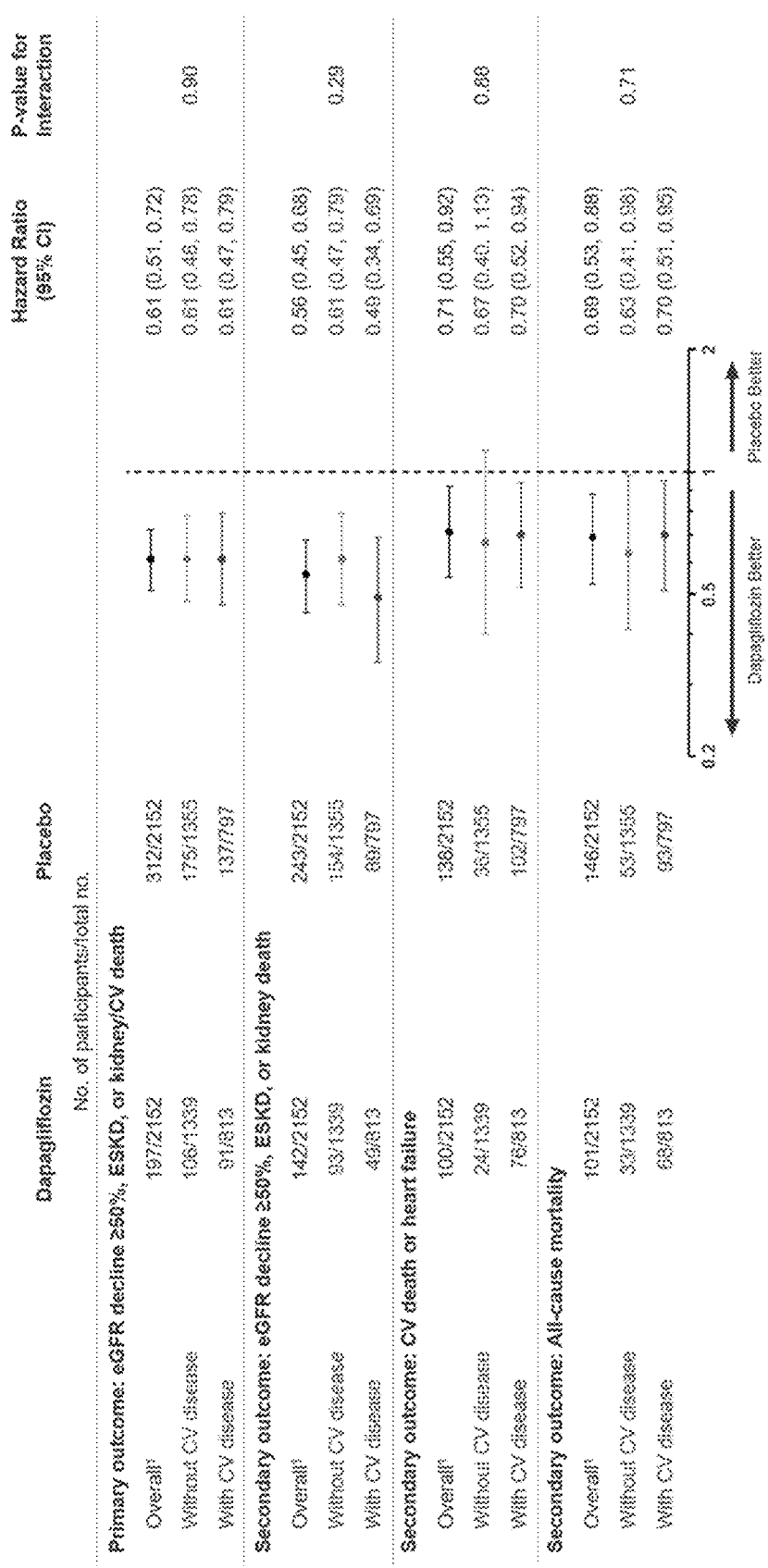
FIG. 22 summarizes the DAPA CKD phase 3 clinical trial primary endpoint (composite of sustained ≥50% eGFR decline, ESKD, or renal or cardiovascular death) and secondary endpoints (secondary renal endpoint (composite of sustained ≥50% eGFR decline, ESKD, or renal death), secondary endpoint (cardiovascular death or hospitalization for heart failure), and all-cause mortality) stratified by patients with or without underlying cardiovascular disease as compared to placebo group or patients receiving at least one standard of care CKD agent alone.
Figure 23:
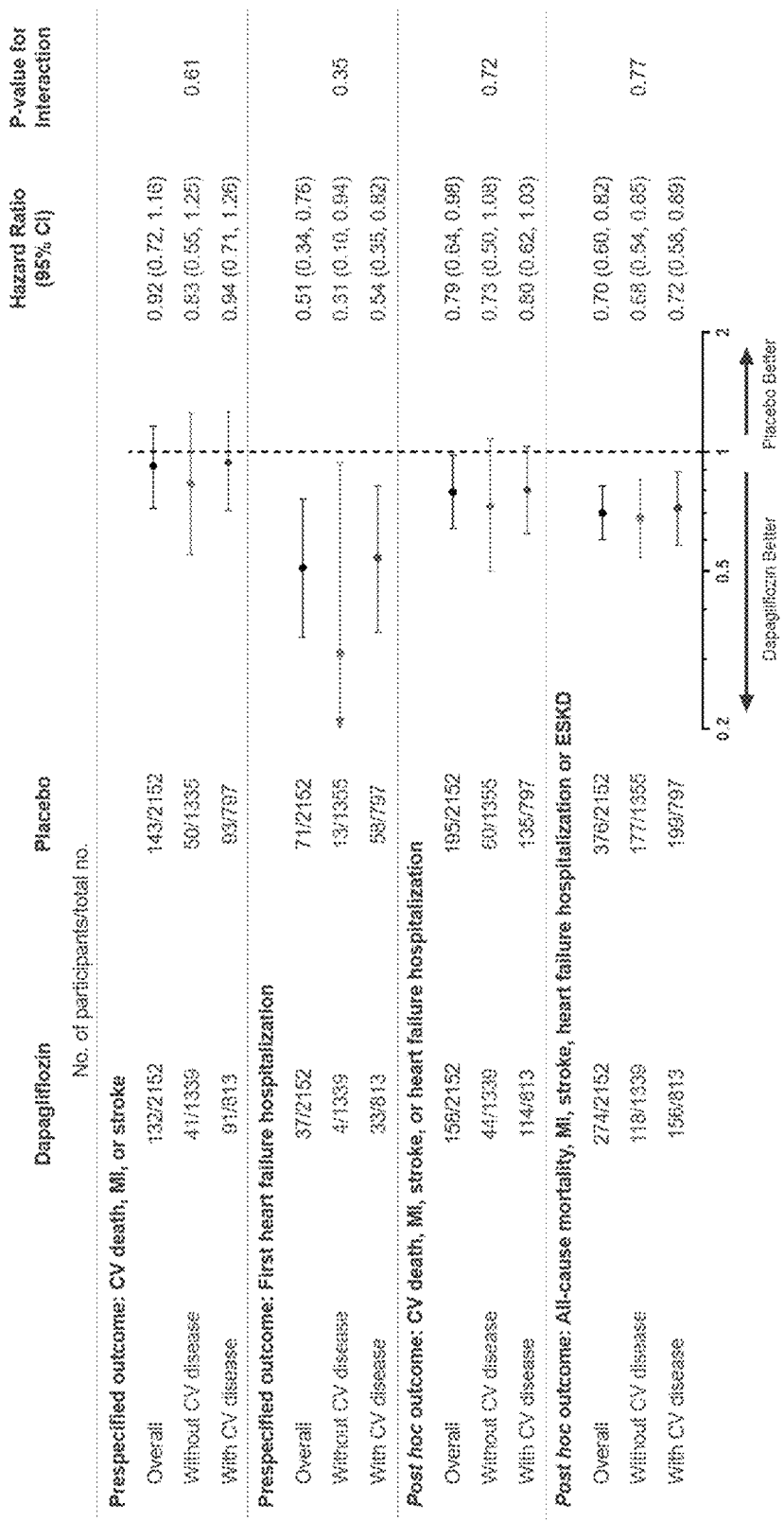
FIG. 23 summarizes the DAPA CKD phase 3 clinical trial prespecified and post hoc exploratory outcomes stratified by patients with or without underlying cardiovascular disease as compared to placebo group or patients receiving at least one standard of care CKD agent alone.
Figure 24:
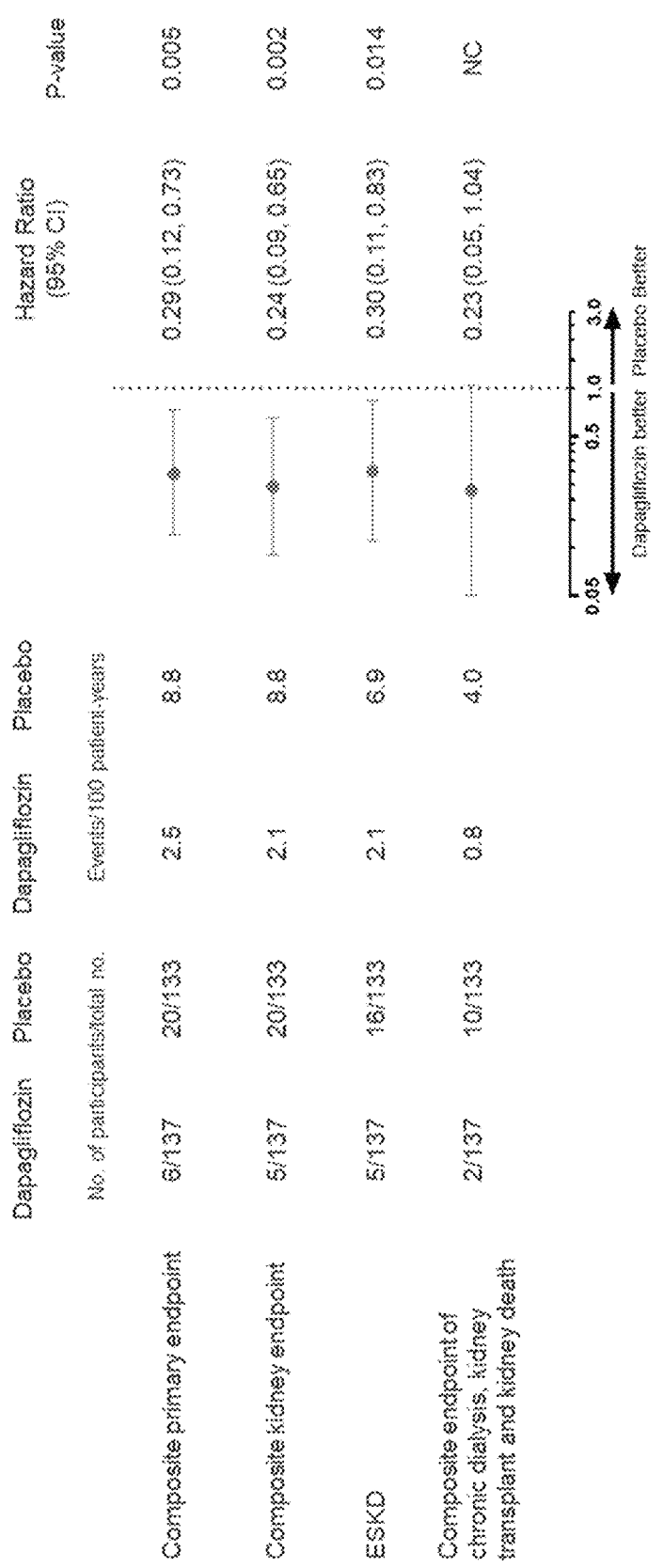
FIG. 24 summarizes the DAPA CKD phase 3 clinical trial primary and secondary endpoints in patients with IgA nephropathy as compared to placebo group or patients receiving at least one standard of care CKD agent alone.

The primary and second end points were also stratified by patients with underlying cause of kidney disease (diabetic nephropathy, ischemic/hypertensive nephropathy, glomerulonephritis, and unknown etiology) (FIGS. 17-20) or stratified by patients with underlying cardiovascular disease (FIG. 22). Further prespecified and post hoc exploratory outcomes were also stratified by patients with underlying cardiovascular disease (FIG. 23). The primary endpoint (FIG. 21) and secondary endpoints (FIG. 24) was also assessed in patients with underlying IgA nephropathy.

The safety outcomes are illustrated in Table 2 below (AE=adverse event). Deaths, SAEs (serious adverse events) and DAEs (discontinuations due to adverse event) were fewer in the dapagliflozin group. AEs leading to dose interruption were balanced between treatment groups. AEs leading to dose reduction were few but more common in the dapagliflozin group. Overall, fewer patients reported SAEs in the dapagliflozin group. The numbers of patients with SAEs was generally balanced between treatment groups across SOCs.

TABLE 2

Safety Outcomes

| | Number (%) of subjects | |
| --- | --- | --- |
| | Dapa 10 mg (N = 2149) | Placebo (N = 2149) |
| Any AE with outcome = death | 106 (4.9) | 159 (7.4) |
| Any SAE (including events with outcome = death) | 633 (29.5) | 729 (33.9) |
| Any AE leading to discontinuation of IP | 118 (5.5) | 123 (5.7) |
| Any AE leading to dose interruption | 272 (12.7) | 268 (12.5) |
| Any AE leading to dose reduction | 39 (1.8) | 31 (1.4) |
| Any definite or probable diabetic ketoacidosis | 0 | 2 (0.1) |
| Any major hypoglycemic event | 14 (0.7) | 28 (1.3) |
| Any event of symptoms of volume depletion | 120 (5.6) | 84 (3.9) |
| Any fracture* | 85 (4.0) | 69 (3.2) |
| Any renal AE | 144 (6.7) | 169 (7.9) |
| Any amputation* | 35 (1.6) | 39 (1.8) |
| Subjects with any SAE | 594 (27.6) | 674 (31.4) |
| Infections and infestations | 171 (8.0) | 180 (8.4) |
| Cardiac disorders | 128 (6.0) | 182 (8.5) |
| Renal and urinary disorders | 107 (5.0) | 143 (6.7) |
| Nervous system disorders | 82 (3.8) | 82 (3.8) |
| Gastrointestinal disorders | 58 (2.7) | 49 (2.3) |
| Injury, poisoning and procedural complications | 56 (2.6) | 52 (2.4) |
| Neoplasms benign, malignant and unspecified (incl cysts and polyps) | 55 (2.6) | 61 (2.8) |
| Vascular disorders | 49 (2.3) | 54 (2.5) |
| Metabolism and nutrition disorders | 44 (2.0) | 75 (3.5) |
| Respiratory, thoracic and mediastinal disorders | 35 (1.6) | 51 (2.4) |
| General disorders and administration site conditions | 25 (1.2) | 31 (1.4) |
| Musculoskeletal and connective tissue disorders | 23 (1.1) | 27 (1.3) |

*AEs for Fractures and amputations are presented for patients on-and off-treatment periods. All other safety variables are presented for the on-treatment period The overall safety profile was generally consistent in patients with T2DM and without diabetes (Table 3 below). No diabetic ketoacidosis or major hypoglycaemia were reported in patients without diabetes. In general, patients with T2DM reported more AEs in all categories compared to patients without diabetes, irrespective of treatment.

TABLE 3

Safety Outcomes in patients with T2DM and without T2DM

| AE Category | T2DM Number (%) of subjects | | No diabetes Number (%) of subjects | |
|---|---|---|---|---|
| | Dapa 10 mg (N = 1453) | Placebo (N = 1450) | Dapa 10 mg (N = 696) | Placebo (N = 699) |
| Any AE with outcome = death* | 89 (6.1) | 126 (8.7) | 17 (2.4) | 33 (4.7) |
| Any SAE (including events with outcome = death)* | 483 (33.2) | 562 (38.8) | 150 (21.6) | 167 (23.9) |
| Any AE leading to discontinuation of IP | 82 (5.6) | 94 (6.5) | 36 (5.2) | 29 (4.1) |
| Any AE leading to dose interruption | 212 (14.6) | 217 (15.0) | 60 (8.6) | 51 (7.3) |
| Any AE leading to dose reduction | 26 (1.8) | 19 (1.3) | 13 (1.9) | 12 (1.7) |
| Any definite or probable diabetic ketoacidosis | 0 | 2 (0.1) | 0 | 0 |
| Any major hypoglycemic event | 14 (1.0) | 28 (1.9) | 0 | 0 |
| Any event of symptoms of volume depletion | 86 (5.9) | 65 (4.5) | 34 (4.9) | 19 (2.7) |
| Any fracture* | 65 (4.5) | 51 (3.5) | 20 (2.9) | 18 (2.6) |
| Any renal AE | 113 (7.8) | 131 (9.0) | 31 (4.5) | 38 (5.4) |
| Any amputation* | 35 (2.4) | 38 (2.6) | 0 | 1 (0.1) |

*AEs or SAEs with an outcome for death and fractures and amputations are presented for patients on-and off-treatment periods. All other safety variables are presented for the on-treatment period Incidence of T2D in Prediabetic Patients A subgroup of 1,398 patients with CKD and prediabetes (HbA1c≥5.7% and <6.5% at baseline) and no prior history of diabetes enrolled in the DAPA-CKD trial were randomized to dapagliflozin 10 mg once daily or placebo. Onset of newly diagnosed T2D (confirmed HbA1c ≥6.5%) was determined through periodic HbA1c testing and comparison between treatment groups assessed through Cox proportional hazards model.

Over median follow-up of 2.4 years, T2D developed in 33/701 (4.7%) in the placebo group and 21/697 (3.0%) in the dapagliflozin group, corresponding to event rates of 2.4/100-patient years and 1.5/100-patient years. Dapagliflozin led to a 38% reduction in T2D incidence (hazard ratio [HR] [95% CI] 0.62 [0.36, 1.08]). There was no heterogeneity in the effect of dapagliflozin on T2D prevention based on most key prespecified subgroups, including age, glycemic status, blood pressure, estimated glomerular filtration rate, albuminuria, race and region, but the effect was more pronounced in females (p interaction 0.03). More than 90% of the participants who developed T2D had prediabetes at baseline (HbA1c≥5.7%-6.4%).

Figure 25:
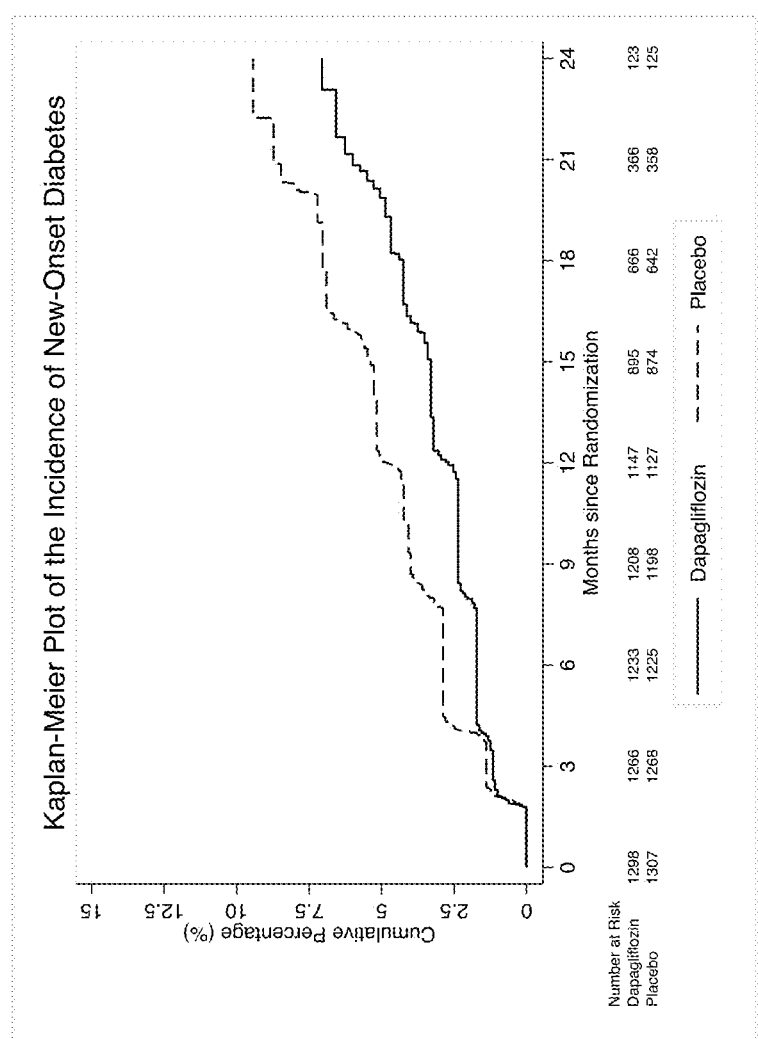
FIG. 25 describes incidence of new onset T2D (HbA1c≥6.5%) measured at 2 consecutive study visits post-randomization or investigator reported new T2D vs placebo patients in the DAPA HF phase 3 clinical trial with previously undiagnosed diabetes, i.e., HbA1c≥6.5%.

In the DAPA-HF trial (heart failure with reduced ejection fraction), of the 2605 non-T2D patients enrolled at baseline (approximately 55% of total patients), 157 developed T2D in trial, 150 (95.5%) of whom had prediabetes (HbA1c≥5.7%-6.4%) (136 [86.6%] using the more restrictive 6.0-6.4% criterion). Those with incident T2D had a higher mean baseline A1c (6.2±0.3 vs 5.7±0.4%; p<0.001), greater BMI (28.5±5.9 vs 27.1±5.7 kg/m$^2$; p=0.003), and lower eGFR (61.5±17.4 vs 68.2±19.3 ml/min/1.73 m$^2$; p<0.001) than those who remained non-diabetic. Dapa reduced new-onset diabetes by 32%: placebo 93/1307 (7.1%) vs. dapa 64/1298 (4.9%); HR 0.68 (95% CI, 0.50-0.94; p=0.019) (Cox.) (FIG. 25)

A meta-analysis of DAPA-CKD and DAPA-HF demonstrated that dapagliflozin reduced new-onset diabetes (HR 0.67 [0.51-0.87]; p=0.003), without heterogeneity between studies (p interaction 0.78).

Appendix A

New York Heart Association (NYHA) Functional Classification

NYHA Functional Classification:

| Class | Patient symptoms |
|---|---|
| I | No limitation of physical activity. Ordinary physical activity does not cause undue fatigue, palpitation, dyspnoea (shortness of breath). |
| II | Slight limitation of physical activity. Comfortable at rest. Ordinary physical activity results in fatigue, palpitation, dyspnoea (shortness of breath). |
| III | Marked limitation of physical activity. Comfortable at rest. Less than ordinary activity causes fatigue, palpitation, or dyspnoea. |
| IV | Unable to carry on any physical activity without discomfort. Symptoms of heart failure at rest. If any physical activity is undertaken, discomfort increases. |

Appendix B
Patient Reported Outcome (PRO) questionnaire: Kidney Disease Quality of Life-36 (KDQOL™-36)

Your Health

This survey includes a wide variety of questions about your health and your life. We are interested in how you feel about each of these issues.

1. In general, would you say your health is: [Mark an ☒ in the one box that best describes your answer.]

| Excellent | Very good | Good | Fair | Poor |
|---|---|---|---|---|
| ☐₁ | ☐₂ | ☐₃ | ☐₄ | ☐₅ |

The following items are about activities you might do during a typical day. Does your health now limit you in these activities? If so, how much? [Mark an ☒ in a box on each line.]

|  | Yes, limited a lot | Yes, limited a little | No, not limited at all |
|---|---|---|---|
| 2. Moderate activities, such as moving a table, pushing a vacuum cleaner, bowling, or playing golf | ☐₁ | ☐₂ | ☐₃ |
| 3. Climbing several flights of stairs | ☐₁ | ☐₂ | ☐₃ |

During the past 4 weeks, have you had any of the following problems with your work or other regular daily activities as a result of your physical health?

|  | Yes ▼ | No ▼ |
|---|---|---|
| 4. Accomplished less than you would like | ☐ | ☐ |
| 5. Were limited in the kind of work or other activities | ☐ | ☐ |

During the past 4 weeks, have you had any of the following problems with your work or other regular daily activities as a result of any emotional problems (such as feeling depressed or anxious)?

|  | Yes ▼ | No ▼ |
|---|---|---|
| 6. Accomplished less than you would like | ☐ | ☐ |
| 7. Didn't do work or other activities as carefully as usual | ☐ | ☐ |

8. During the past 4 weeks, how much did pain interfere with your normal work (including both work outside the home and housework)?

| Not at all ▼ | A little bit ▼ | Moderately ▼ | Quite a bit ▼ | Extremely ▼ |
|---|---|---|---|---|
| ☐ | ☐ | ☐ | ☐ | ☐ |

These questions are about how you feel and how things have been with you during the past 4 weeks. For each question, please give the one answer that comes closest to the way you have been feeling.

How much of the time during the past 4 weeks...

|  | All of the time | Most of the time | A good bit of the time | Some of the time | A little of the time | None of the time |
|---|---|---|---|---|---|---|
| 9. Have you felt calm and peaceful? | ☐₁ | ☐₂ | ☐₃ | ☐₄ | ☐₅ | ☐₆ |
| 10. Did you have a lot of energy? | ☐₁ | ☐₂ | ☐₃ | ☐₄ | ☐₅ | ☐₆ |
| 11. Have you felt downhearted and blue? | ☐₁ | ☐₂ | ☐₃ | ☐₄ | ☐₅ | ☐₆ |

12. During the past 4 weeks, how much of the time has your physical health or emotional problems interfered with your social activities (like visiting with friends, relatives, etc.)?

| All of the time | Most of the time | Some of the time | A little of the time | None of the time |
|---|---|---|---|---|
| ☐₁ | ☐₂ | ☐₃ | ☐₄ | ☐₅ |

Your Kidney Disease

How true or false is each of the following statements for you?

|  | Definitely true | Mostly true | Don't know | Mostly false | Definitely false |
|---|---|---|---|---|---|
| 13. My kidney disease interferes too much with my life | ☐₁ | ☐₂ | ☐₃ | ☐₄ | ☐₅ |
| 14. Too much of my time is spent dealing with my kidney disease | ☐₁ | ☐₂ | ☐₃ | ☐₄ | ☐₅ |
| 15. I feel frustrated dealing with my kidney disease | ☐₁ | ☐₂ | ☐₃ | ☐₄ | ☐₅ |
| 16. I feel like a burden on my family | ☐₁ | ☐₂ | ☐₃ | ☐₄ | ☐₅ |

During the past 4 weeks, to what extent were you bothered by each of the following?

|  | Not bothered | Somewhat bothered | Moderately bothered | Very much bothered | Extremely bothered |
|---|---|---|---|---|---|
| 17. Soreness in your muscles? | ☐₁ | ☐₂ | ☐₃ | ☐₄ | ☐₅ |
| 18. Chest pain? | ☐₁ | ☐₂ | ☐₃ | ☐₄ | ☐₅ |
| 19. Cramps? | ☐₁ | ☐₂ | ☐₃ | ☐₄ | ☐₅ |
| 20. Itchy skin? | ☐₁ | ☐₂ | ☐₃ | ☐₄ | ☐₅ |
| 21. Dry skin? | ☐₁ | ☐₂ | ☐₃ | ☐₄ | ☐₅ |
| 22. Shortness of breath? | ☐₁ | ☐₂ | ☐₃ | ☐₄ | ☐₅ |
| 23. Faintness or dizziness? | ☐₁ | ☐₂ | ☐₃ | ☐₄ | ☐₅ |
| 24. Lack of appetite? | ☐₁ | ☐₂ | ☐₃ | ☐₄ | ☐₅ |
| 25. Washed out or drained? | ☐₁ | ☐₂ | ☐₃ | ☐₄ | ☐₅ |
| 26. Numbness in hands or feet? | ☐₁ | ☐₂ | ☐₃ | ☐₄ | ☐₅ |
| 27. Nausea or upset stomach? | ☐₁ | ☐₂ | ☐₃ | ☐₄ | ☐₅ |
| 28ª. (Hemodialysis patient only) Problems with your access site? | ☐₁ | ☐₂ | ☐₃ | ☐₄ | ☐₅ |
| 28ᵇ. (Peritoneal dialysis patient only) Problems with your catheter site? | ☐₁ | ☐₂ | ☐₃ | ☐₄ | ☐₅ |

Effects of Kidney Disease on Your Daily Life

Some people are bothered by the effects of kidney disease on their daily life, while others are not. How much does kidney disease bother you in each of the following areas?

|  | Not at all bothered | Somewhat bothered | Moderately bothered | Very much bothered | Extremely bothered |
|---|---|---|---|---|---|
| 29. Fluid restriction? | ☐₁ | ☐₂ | ☐₃ | ☐₄ | ☐₅ |
| 30. Dietary restriction? | ☐₁ | ☐₂ | ☐₃ | ☐₄ | ☐₅ |
| 31. Your ability to work around the house? | ☐₁ | ☐₂ | ☐₃ | ☐₄ | ☐₅ |
| 32. Your ability to travel? | ☐₁ | ☐₂ | ☐₃ | ☐₄ | ☐₅ |
| 33. Being dependent on doctors and other medical staff? | ☐₁ | ☐₂ | ☐₃ | ☐₄ | ☐₅ |
| 34. Stress or worries caused by kidney disease? | ☐₁ | ☐₂ | ☐₃ | ☐₄ | ☐₅ |
| 35. Your sex life? | ☐₁ | ☐₂ | ☐₃ | ☐₄ | ☐₅ |
| 36. Your personal appearance? | ☐₁ | ☐₂ | ☐₃ | ☐₄ | ☐₅ |

Appendix C
Patient Reported Outcome (PRO) questionnaire: Euroqol Five-Dimensional Five-Level Questionnaire (Eq-5d-5l Under each heading, please tick the ONE box that best describes your health TODAY.

MOBILITY
I have no problems in walking about ☐
I have slight problems in walking about ☐
I have moderate problems in walking about ☐
I have severe problems in walking about ☐
I am unable to walk about ☐

SELF-CARE
I have no problems washing or dressing myself ☐
I have slight problems washing or dressing myself ☐
I have moderate problems washing or dressing myself ☐
I have severe problems washing or dressing myself ☐
I am unable to wash or dress myself ☐

USUAL ACTIVITIES *(e.g. work, study, housework, family or leisure activities)*
I have no problems doing my usual activities ☐
I have slight problems doing my usual activities ☐
I have moderate problems doing my usual activities ☐
I have severe problems doing my usual activities ☐
I am unable to do my usual activities ☐

PAIN / DISCOMFORT
I have no pain or discomfort ☐
I have slight pain or discomfort ☐
I have moderate pain or discomfort ☐
I have severe pain or discomfort ☐
I have extreme pain or discomfort ☐

ANXIETY / DEPRESSION
I am not anxious or depressed ☐
I am slightly anxious or depressed ☐
I am moderately anxious or depressed ☐
I am severely anxious or depressed ☐
I am extremely anxious or depressed ☐

- We would like to know how good or bad your health is TODAY.
- This scale is numbered from 0 to 100.
- 100 means the best health you can imagine.
  0 means the worst health you can imagine.
- Mark an X on the scale to indicate how your health is TODAY.
- Now, please write the number you marked on the scale in the box below.
YOUR HEALTH TODAY = ☐
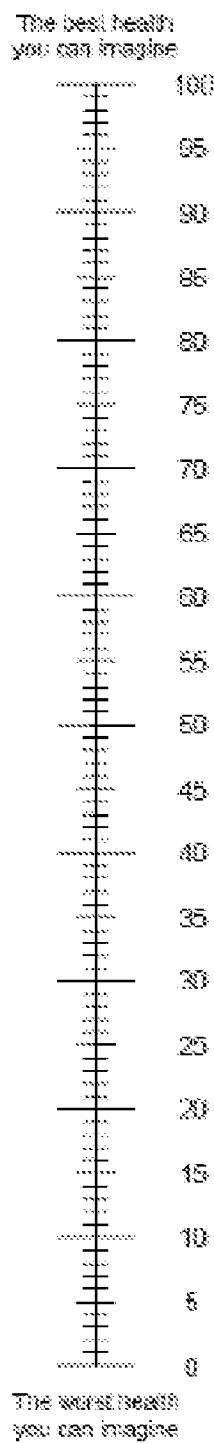

The invention claimed is:

1. A method for treating a patient with chronic kidney disease at risk of progression, the method comprising:
   administering dapagliflozin once daily to the patient at a dose and duration sufficient to reduce the patient's risk of sustained estimated glomerular filtration rate (eGFR) decline, end-stage kidney disease (ESKD), cardiovascular (CV) death, and hospitalization for heart failure;
   wherein the patient does not have type II diabetes; and
   wherein the duration is at least four months.

2. The method of claim 1, wherein the sustained decline in eGFR is ≥50%.

3. The method of claim 1, wherein the end-stage kidney disease (ESKD) comprises sustained eGFR <15 mL/min/1.73 m², initiation of chronic dialysis treatment and/or renal transplant.

4. The method of claim 1, wherein prior to the administration, the patient had (i) an eGFR ≥25 and ≤75 mL/min/1.73 m²; and/or (ii) a urine albumin creatinine ratio (UACR) ≥200 and ≤5000 mg/g.

5. The method of claim 1, wherein (i) prior to the administration, the patient was receiving an angiotensin-converting enzyme inhibitor (ACEi) or an angiotensin receptor blocker (ARB); and/or (ii) during the administration, the patient is also administered an ACEi or an ARB.

6. The method of claim 5, wherein the angiotensin-converting enzyme inhibitor (ACEi) is chosen from captopril, enalapril, and lisinopril.

7. The method of claim 5, wherein the angiotensin receptor blocker (ARB) is chosen from valsartan, losartan, and irbesartan.

8. A method for treating a patient with chronic kidney disease at risk of progression, the method comprising:
   administering dapagliflozin once daily to the patient at a dose and duration sufficient to reduce a risk of an incidence of a composite endpoint;
   wherein the patient does not have type II diabetes;
   wherein the composite endpoint is ~50% sustained decline in estimated glomerular filtration rate (eGFR), progression to end-stage kidney disease (ESKD), and CV or renal death; and
   wherein the duration is at least four months.

9. The method of claim 8, wherein the end-stage kidney disease (ESKD) comprises sustained eGFR <15 mL/min/1.73 m², initiation of chronic dialysis treatment and/or renal transplant.

10. The method of claim 8, wherein prior to the administration, the patient had (i) an eGFR ≥25 and ≤75 mL/min/1.73 m²; and/or (ii) a urine albumin creatinine ratio (UACR) ≥200 and ≤5000 mg/g.

11. The method of claim 8, wherein (i) prior to the administration, the patient was receiving an angiotensin-converting enzyme inhibitor (ACEi) or an angiotensin receptor blocker (ARB); and/or (ii) during the administration, the patient is also administered an ACEi or an ARB.

12. The method of claim 11, wherein the angiotensin-converting enzyme inhibitor (ACEi) is chosen from captopril, enalapril, and lisinopril.

13. The method of claim 11, wherein the angiotensin receptor blocker (ARB) is chosen from valsartan, losartan, and irbesartan.

14. The method of claim 8, wherein the method satisfies at least one of the following conditions:

a) the method results in a hazard ratio for time to first event in the composite endpoint that is less than one relative to an administration regimen where the patient receives no dapagliflozin;

b) the method results in a hazard ratio for time to first event in the composite endpoint that is statistically nominally less than one relative to an administration regimen where the patient receives no dapagliflozin;

c) the method results in a hazard ratio for time to first event in the composite endpoint of approximately 0.61 relative to an administration regimen where the patient receives no dapagliflozin;

d) the method results in a 95% confidence interval for the hazard ratio for time to first event in the composite endpoint of approximately 0.51 to 0.72 relative to an administration regimen where the patient receives no dapagliflozin;

e) the method numerically reduces the absolute risk of the composite endpoint relative to an administration regimen where the patient receives no dapagliflozin;

f) the method results in a nominally significant risk reduction of the composite endpoint relative to an administration regimen where the patient receives no dapagliflozin;

g) the method results in a numerical reduction in the composite endpoint relative to an administration regimen where the patient receives no dapagliflozin;

h) the method results in a hazard ratio for time to first event in a composite endpoint of CV death and hospitalization for heart failure of approximately 0.71 relative to an administration regimen where the patient receives no dapagliflozin; and/or i) the method results in a hazard ratio for time to death from all causes of approximately 0.69 relative to an administration regimen where the patient receives no dapagliflozin.

15. The method of claim 1, wherein the method further comprises administering to the patient a pharmaceutical composition comprising a therapeutically effective amount of AZD9977 or a pharmaceutically acceptable salt thereof.

16. The method of claim 15, wherein the patient is at high risk for hyperkalemia.

17. The method of claim 15, wherein the therapeutically effective amount of AZD9977 or a pharmaceutically acceptable salt thereof is 15-150 mg daily.

18. The method of claim 15, wherein the therapeutically effective amount of dapagliflozin is 10 mg orally once per day.

19. The method of claim 8, wherein the method further comprises administering to the patient a pharmaceutical composition comprising a therapeutically effective amount of AZD9977 or a pharmaceutically acceptable salt thereof.

20. The method of claim 19, wherein the patient is at high risk for hyperkalemia.

21. The method of claim 19, wherein the therapeutically effective amount of AZD9977 or a pharmaceutically acceptable salt thereof is 15-150 mg daily.

22. The method of claim 19, wherein the amount of dapagliflozin is 10 mg orally once per day.

23. The method of claim 1, wherein the patient is not on chronic dialysis.

24. The method of claim 8, wherein the patient is not on chronic dialysis.

* * * * *

UNITED STATES PATENT AND TRADEMARK OFFICE
CERTIFICATE OF CORRECTION

| | | |
|---|---|---|
| PATENT NO. | : 12,213,988 B2 | Page 1 of 1 |
| APPLICATION NO. | : 17/347230 | |
| DATED | : February 4, 2025 | |
| INVENTOR(S) | : Anna Maria Langkilde et al. | |

It is certified that error appears in the above-identified patent and that said Letters Patent is hereby corrected as shown below:

On the Title Page

Item (12) "Langkilde" should read --Langkilde et al.--.

Item (72) should be changed from "Inventor: Anna Maria Langkilde, Södertälje (SE)" to --Inventors: Anna Maria Langkilde, Södertälje (SE) and Philip Ambery, Södertälje (SE)--.

Signed and Sealed this
Twenty-second Day of July, 2025

Coke Morgan Stewart
*Acting Director of the United States Patent and Trademark Office*